(12) United States Patent
Vieira et al.

(10) Patent No.: US 11,607,402 B2
(45) Date of Patent: Mar. 21, 2023

(54) INHIBITION OF DIPEPTIDE REPEAT PROTEINS

(71) Applicant: ALS Therapy Development Institute, Cambridge, MA (US)

(72) Inventors: Fernando G. Vieira, Newton, MA (US); Alan Premasiri, Boston, MA (US); Anna Gill, Reading, MA (US)

(73) Assignee: ALS Therapy Development Institute, Cambridge, MA (US)

( * ) Notice: Subject to any disclaimer, the term of this patent is extended or adjusted under 35 U.S.C. 154(b) by 151 days.

(21) Appl. No.: 16/895,875

(22) Filed: Jun. 8, 2020

(65) Prior Publication Data

US 2020/0405689 A1 Dec. 31, 2020

Related U.S. Application Data

(60) Provisional application No. 63/028,753, filed on May 22, 2020, provisional application No. 62/868,267, filed on Jun. 28, 2019.

(51) Int. Cl.
| | | |
|---|---|---|
| *A61K 31/40* | (2006.01) | |
| *A61K 31/4155* | (2006.01) | |
| *A61K 31/4545* | (2006.01) | |
| *A61K 31/428* | (2006.01) | |
| *A61K 45/06* | (2006.01) | |

(52) U.S. Cl.
CPC .......... *A61K 31/40* (2013.01); *A61K 31/4155* (2013.01); *A61K 31/4545* (2013.01); *A61K 31/428* (2013.01); *A61K 45/06* (2013.01)

(58) Field of Classification Search
CPC .............................. A61K 31/40; A61K 31/428
See application file for complete search history.

(56) References Cited

U.S. PATENT DOCUMENTS

| | | |
|---|---|---|
| 8,722,877 B2 | 5/2014 | Chesworth et al. |
| 8,906,900 B2 | 12/2014 | Duncan et al. |
| 8,940,726 B2 | 1/2015 | Duncan et al. |
| 8,952,026 B2 | 2/2015 | Mitchell et al. |
| 8,993,555 B2 | 3/2015 | Duncan et al. |
| 9,023,883 B2 | 5/2015 | Kuntz et al. |
| 9,029,343 B2 | 5/2015 | Chesworth et al. |
| 9,045,455 B2 | 6/2015 | Mitchell et al. |
| 9,120,757 B2 | 9/2015 | Chesworth et al. |
| 9,133,189 B2 | 9/2015 | Chesworth et al. |
| 9,221,794 B2 | 12/2015 | Duncan et al. |
| 9,346,761 B2 | 5/2016 | Chesworth et al. |
| 9,346,802 B2 | 5/2016 | Chesworth et al. |
| 9,365,555 B2 | 6/2016 | Duncan et al. |
| 9,394,258 B2 | 7/2016 | Chesworth et al. |
| 9,447,079 B2 | 9/2016 | Mitchell et al. |
| 9,688,665 B2 | 6/2017 | Knutson et al. |
| 9,718,816 B2 | 8/2017 | Chesworth et al. |
| 2016/0031839 A1 | 2/2016 | Chesworth et al. |
| 2016/0137609 A1 | 5/2016 | Chesworth et al. |
| 2017/0198006 A1 | 7/2017 | Duncan et al. |
| 2017/0210751 A1 | 7/2017 | Duncan et al. |
| 2017/0280720 A1 | 10/2017 | Chesworth et al. |
| 2017/0283400 A1 | 10/2017 | Mitchell et al. |
| 2017/0283440 A1 | 10/2017 | Chesworth et al. |
| 2017/0291905 A1 | 10/2017 | Chesworth et al. |
| 2017/0298073 A1 | 10/2017 | Olhava et al. |
| 2017/0305922 A1 | 10/2017 | Chesworth et al. |
| 2019/0054070 A1 | 2/2019 | Alkon |
| 2019/0077795 A1 | 3/2019 | Mitchell et al. |
| 2019/0083482 A1 | 3/2019 | Duncan et al. |
| 2019/0218194 A1 | 7/2019 | Chesworth et al. |
| 2022/0142974 A1 | 5/2022 | Vieira et al. |

FOREIGN PATENT DOCUMENTS

| | | |
|---|---|---|
| EP | 2970131 B1 | 11/2017 |
| WO | 2016044576 A1 | 3/2016 |
| WO | 2016044641 A2 | 3/2016 |

OTHER PUBLICATIONS

International Preliminary Report on Patentability, PCT/US2020/036643, dated Dec. 28, 2021, 9 pages.
Barmada S."Linking RNA Dysfunction and Neurodegeneration in Amyotrophic Lateral Sclerosis," Neurotherapeutics, vol. 12(2):340-351 (2015).
Freibaum, B. et al., "The Role of Dipeptide Repeats in C9ORF72-Related ALS-FTD," Frontiers in Molecular Nueroscience, vol. 10: 9 pages (2017).
International Search Report and Written Opinion, PCT/US2020/036643, dated Oct. 19, 2020, 18 pages.
Kelsey R. "Arginine dimethylation is increased in patients with ALS and can predict disease progression" Nature Reviews. Neurology, vol. 15(5):p. 246 (2019).
Li, X. et al., "A patent review of arginine methyltransferase inhibitors (2010-2018)",Expert Opinion on Therapeutic Patents, vol. 29(2):97-114(2019).
Premasiri, A. et al., "Type I PRMT Inhibition Protects Against C9ORF72 Arginine-Rich Dipeptide Repeat Toxicity," Frontier in Pharmacology, vol. 11: 21 pages (2020).
U.S. Appl. No. 17/584,522, filed Jan. 26, 2022, Fernando G. Vieira.

*Primary Examiner* — Kamal A Saeed
(74) *Attorney, Agent, or Firm* — Nelson Mullins Riley & Scarborough LLP; Jeanne M. DiGiorgio, Esq.

(57) ABSTRACT

Methods are disclosed for treating neurodegenerative disorders, such as ALS and FTD by using an effective amount of a type I protein arginine methyltransferase (Type I PRMT) inhibitor to decrease cellular toxicity caused by dipeptide repeat proteins (DRPs).

6 Claims, 34 Drawing Sheets
Specification includes a Sequence Listing.

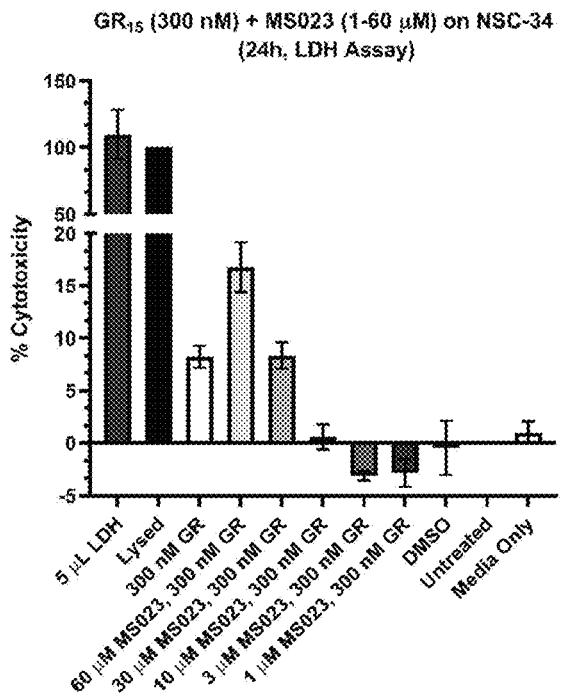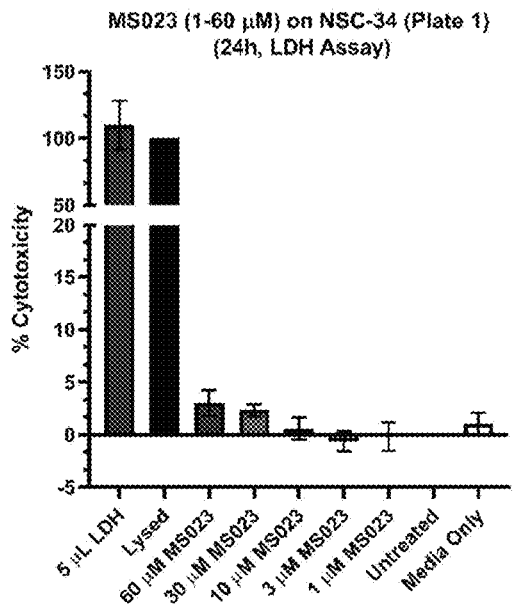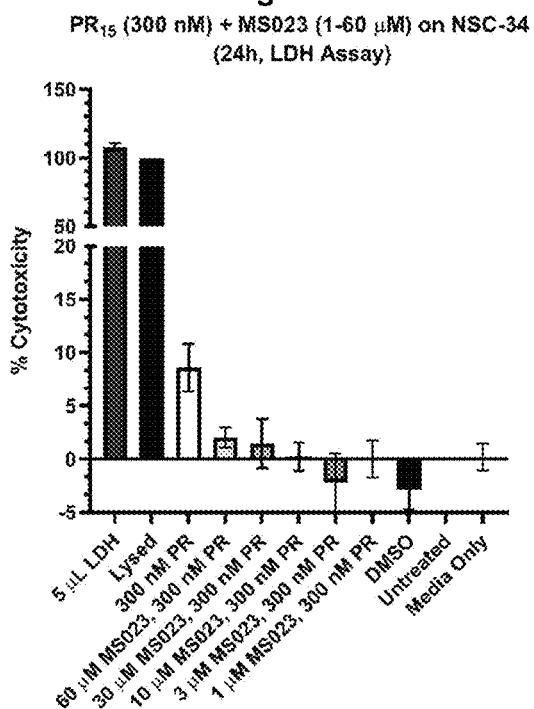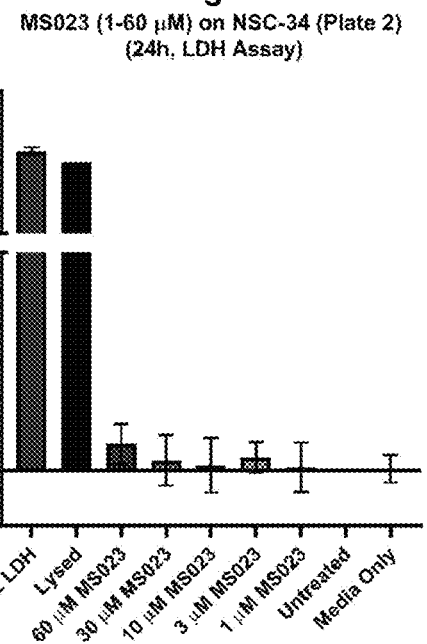

Fig. 10A
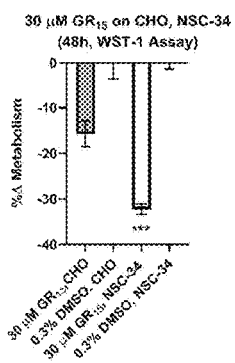
Fig. 10B
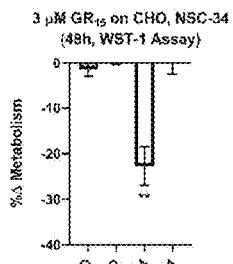
Fig. 10C
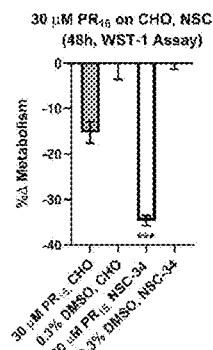
Fig. 10D
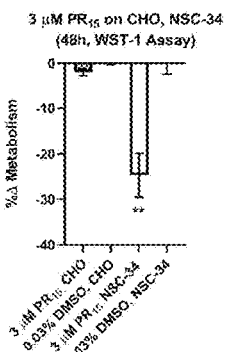
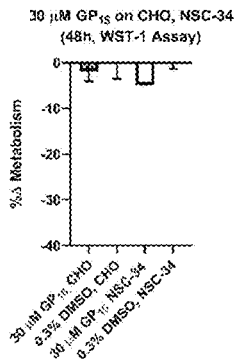
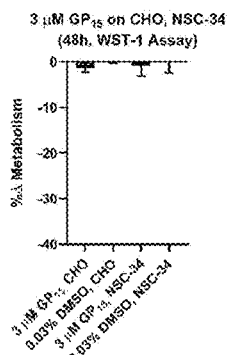
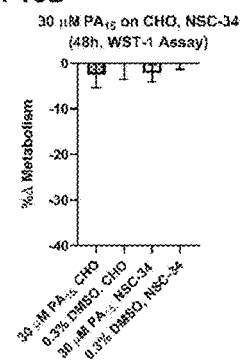
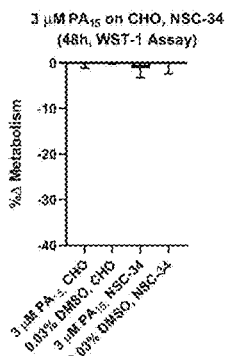

| Small Molecule | IC50 (µM) | EC50 (µM) | | | | Chemical Structure |
|---|---|---|---|---|---|---|
| | | 3 µM GR15 Challenge | | 3 µM PR15 Challenge | | |
| | | WST-1 | LDH | WST-1 | LDH | |
| MS023 | 0.545 | 0.08 | 0.012 | 0.132 | ~0.029 | 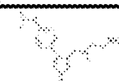 |
| MS049 | 1.082 | ~2.103 | ~1.765 | ~1.99 | ~1.616 | 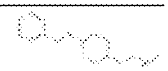 |
| EPZ020411 | 1.529 | 12.01 | 1.41 | >1 | ~2.939 | 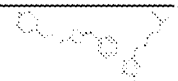 |
| GSK715 | 0.08 | ~0.6724 | ~0.768 | 0.478 | ~0.269 | 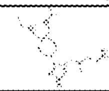 |
| GSK591* | 1.914 | - | - | - | - | 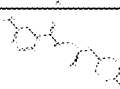 |
| MS094** | - | - | - | - | - | 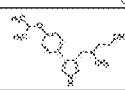 |
*Inhibits Symmetrical Dimetylation
**Inert analog of MS023
Fig. 33

INHIBITION OF DIPEPTIDE REPEAT PROTEINS

RELATED APPLICATIONS

This application claims priority to U.S. Provisional Application No. 62/868,267, filed on Jun. 28, 2019, and U.S. Provisional Application No. 63/028,753, filed on May 22, 2020. The contents of both applications are hereby incorporated by reference.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Feb. 28, 2022, is named ALSE_014_Sequence_Listing and is 1765 bytes in size.

BACKGROUND

The present invention relates to the treatment of neurological disorders, such as Amyotrophic Lateral Sclerosis (ALS) and Frontotemporal Dementia (FTD).

ALS is a progressive neurological disorder characterized by muscle fiber atrophy resulting from the degeneration of motor neurons in the spinal column and brain. FTD is the second most common form of early-onset dementia (after Alzheimer's disease) in people under the age of 65.

It has been reported recently that the expansion of a hexanucleotide (GGGGCC) repeat in the gene chromosome 9 open reading frame 72 (C9ORF72) is a possible contributing factor to the onset of both ALS and FTD. See, Jovicic et al. "Modifiers of C9orf72 DRP toxicity implicate nucleocytoplasmic transport impairments in c9FTD/ALS," *Nat Neurosci.* 2015 Sep. 18(9) 1226-1229. RNA transcribed from a mutated C9ORF72 gene that contains expanded GGGGCC repeats is translated through a non-ATG initiated mechanism. This drives the formation and intracellular accumulation of dipeptide repeat proteins (DRPs). DRPs translated from all six reading frames in either the sense or antisense direction of the hexanucleotide repeat result in the expression of five DRPs: glycine-alanine (GA), glycine-arginine (GR), proline-alanine (PA), proline-arginine (PR) and glycine-proline (GP). (GP, in particular, can be generated from both the sense and antisense reading frames.) However, the mechanisms of action and the contributions of each DRP to neurodegeneration remain unclear.

It is an object of the present invention to provide new approaches for treating neurodegenerative diseases by inhibiting or decreasing the cellular toxicity caused by DRPs.

SUMMARY

Methods are disclosed for decreasing cellular toxicity caused by DRPs. It has been discovered that two types of DRPs, glycine-arginine (GR) and proline-arginine (PR), are particularly detrimental to cellular viability and can cause cellular dysfunction or lead to cell death, especially in neuronal cells, if unchecked. Not being bound by any theory, in some aspects, the toxic effects caused by DRPs is driven by asymmetric methylation of the arginine substrates within the dipeptide repeats, rather than by aberrant methylation of endogenous proteins.

In one aspect of the invention, methods are disclosed that include administering an effective amount of a type I protein arginine methyltransferase (Type I PRMT) inhibitor to decrease toxicity of DRPs in cells, e.g., to abrogate toxicity produced by asymmetric methylation of the arginine substrates within the dipeptide repeats. Useful Type I PRMT inhibitors include agents that can inhibit at least one of PRMT1, PRMT3, PRMT4, PRMT6, and/or PRMT8. Examples of Type I PRMT inhibitors include, but are not limited to, MS023, MS049, EPZ020411, GSK715 (also referred to as GSK3368715 or EPZ019997), and/or TP 064 (described in more detail below).

Type I PRMT inhibitors are particularly useful in decreasing cellular toxicity caused by DRPs that include the amino acid arginine (R), e.g., poly-glycine-arginine (GR) and/or poly-proline-arginine (PR) dipeptide repeats. The invention can be especially useful in protecting neuronal cells, e.g., sensory neurons, motor neurons, and/or interneurons, from DRP toxicity.

In particular, the methods can be useful in treating neurodegenerative diseases when such diseases are associated with the expression of DRPs in a subject's neuronal cells. For example, the methods can be used in the treatment of C9ORF72-linked ALS or C9ORF72-linked FTD.

In yet another aspect, the methods of treating further includes administration of a second therapeutic agent, e.g., riluzole and/or edaravone. Alternatively, the second therapeutic is an antibody, or antigen binding portion thereof, e.g., an antibody that blocks the interaction of human CD40 and CD40L.

Other features and advantages of the instant disclosure will be apparent from the following detailed description and examples, which should not be construed as limiting. The contents of all references, GenBank entries, patents and published patent applications cited throughout this application are expressly incorporated herein by reference.

BRIEF DESCRIPTION OF THE DRAWINGS

FIGS. 4A-4D are graphs comparing the activity of MS023 (1-60 PM) to abrogate cytotoxicity produced by $GR_{15}$ (SEQ ID NO: 1) (300 nM) (FIGS. 4A and 4B) and $PR_{15}$ (SEQ ID NO: 2) (300 nM) (FIGS. 4C and 4D) measured by LDH assay.

FIGS. 10A-10D are graphs comparing of DRP-induced dysmetabolism phenotypes in neuronal and non-neuronal cell types measured by WST-1 assay using Chinese Hamster Ovary (CHO) and Mouse Neuroblastoma-Spinal Cord Hybrid (NSC-34) cells and both arginine-rich: $GR_{15}$, (SEQ ID NO: 1) $PR_{15}$, (SEQ ID NO: 2) (FIGS. 10A and 10B) and non-arginine-rich: $GP_{15}$ (SEQ ID NO: 3), $PA_{15}$ (SEQ ID NO: 4) (FIGS. 10C and 10D), DRPs (at 30 and 3 μM doses).

FIG. 33 is a table summarizing the IC50s for inhibition of dimethylation activity and EC50s for abrogation of toxicity caused by $GR_{15}$ (SEQ ID NO: 1) or $PR_{15}$ (SEQ ID NO: 2) challenge, and chemical structures for each compound tested.

DETAILED DESCRIPTION

Figure 1A:
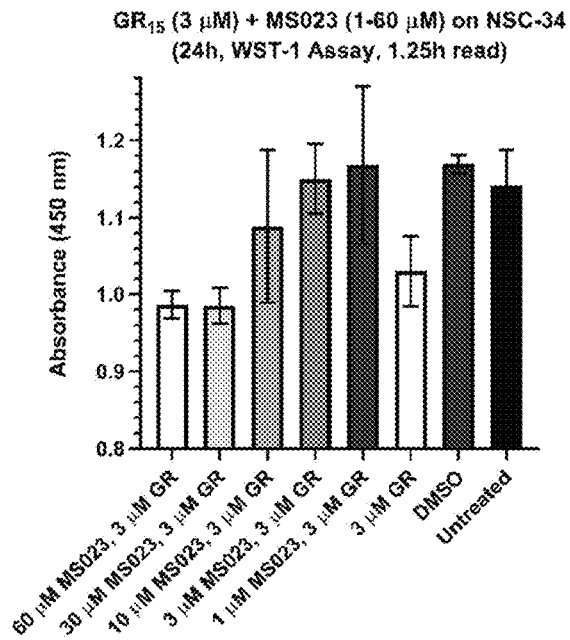
FIGS. 1A-1D are graphs comparing the activity of MS023 (FIGS. 1A and 1B) and GSK591 (FIGS. 1C and 1D) to abrogate dysmetabolism induced by 3 µM $GR_{15}$ (SEQ ID NO: 1) in NSC-34 motor-neuron-like cells measured by WST-1 assay.
Figure 1B:
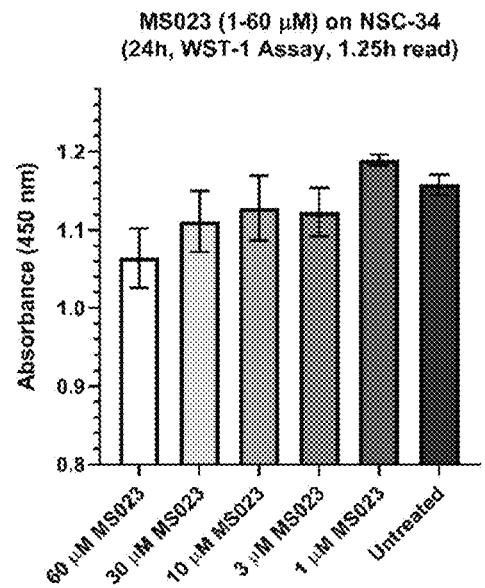
Figure 1C:
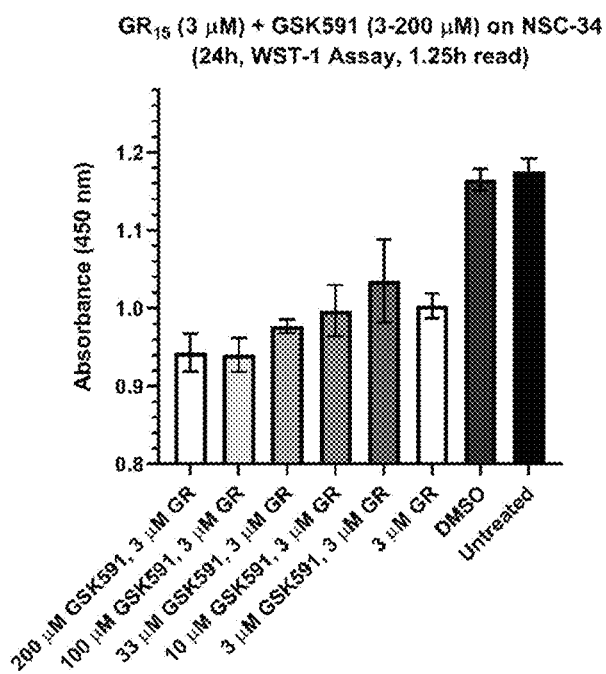
Figure 1D:
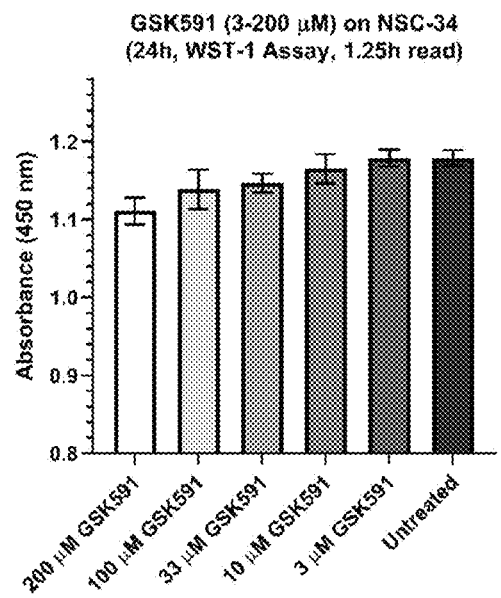
Figure 2A:
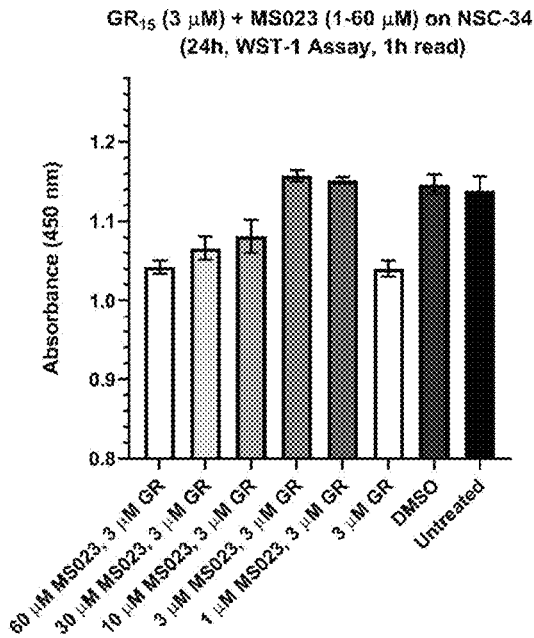
FIGS. 2A-2D are graphs comparing the activity of MS023 to abrogate dysmetabolism induced by 3 µM $GR_{15}$ (SEQ ID NO: 1)(FIGS. 2A and 2B) or 3 µM $PR_{15}$ (SEQ ID NO: 2)(FIGS. 2C and 2D) in NSC-34 motor-neuron-like cells measured by WST-1 assay.
Figure 2B:
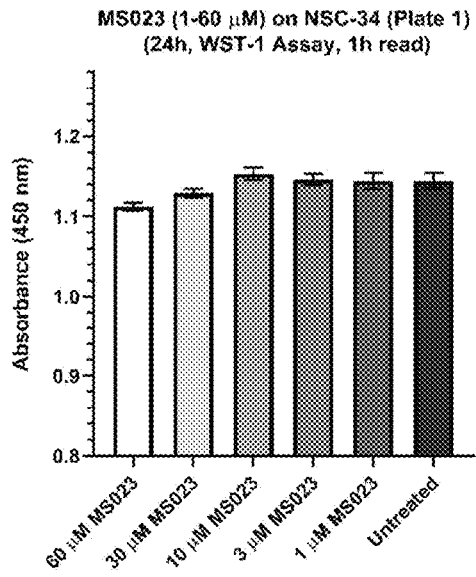
Figure 2C:
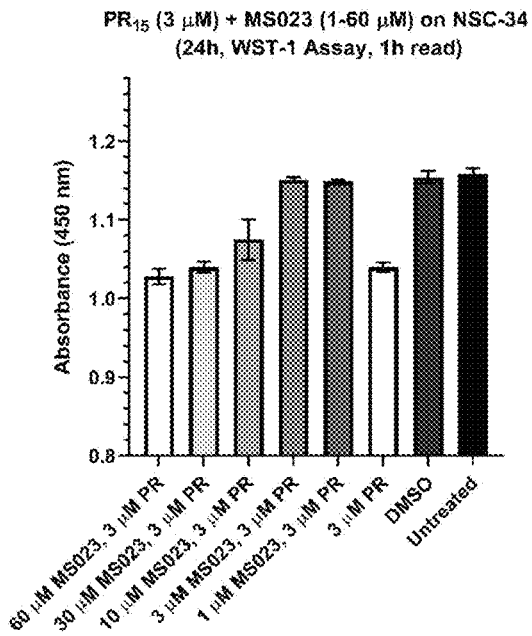
Figure 2D:
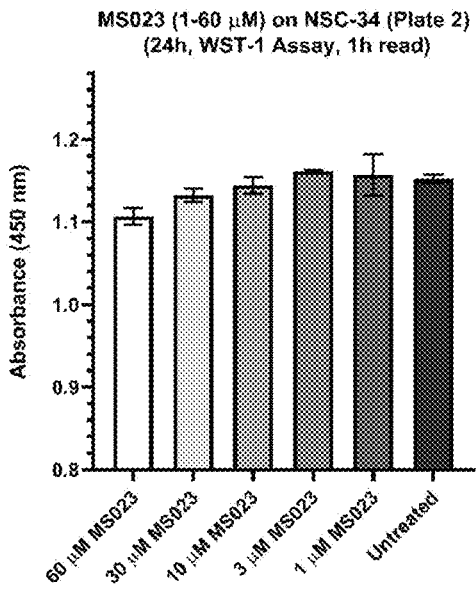
Figure 3A:
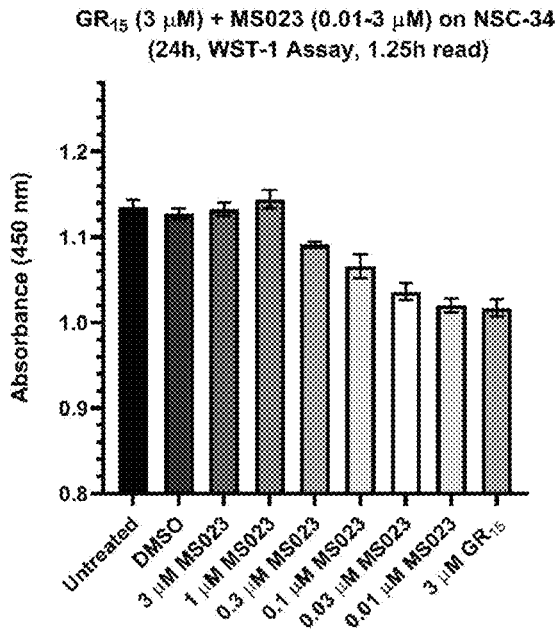
FIGS. 3A-3D are graphs comparing the effect of lower dose ranges of DRPs (0.01-3 µM) on the activity of MS023 to abrogate dysmetabolism induced by 3 µM doses of $GR_{15}$ (SEQ ID NO: 1)(FIGS. 3A and 3B) or $PR_{15}$ (SEQ ID NO: 2)(FIGS. 3C and 3D) measured by WST-1 assay.
Figure 3B:
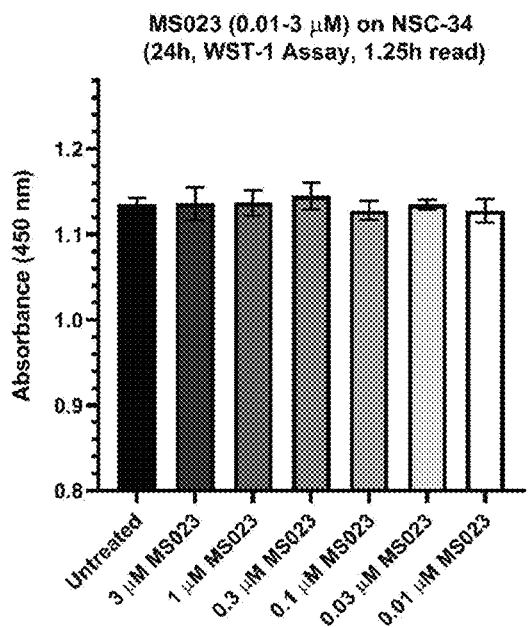
Figure 3C:
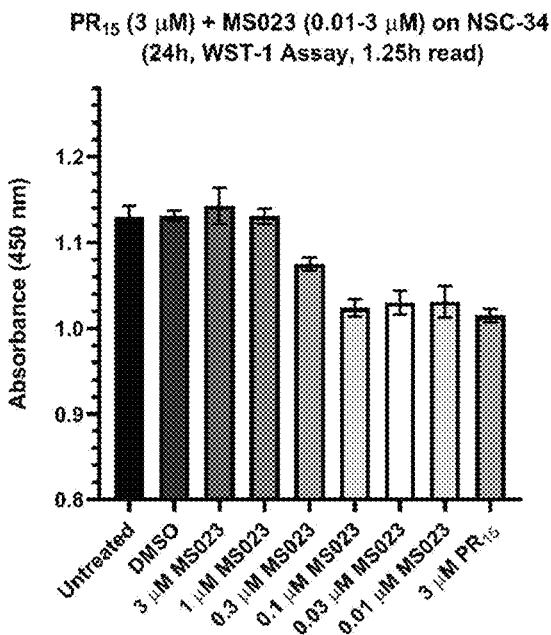
Figure 3D:
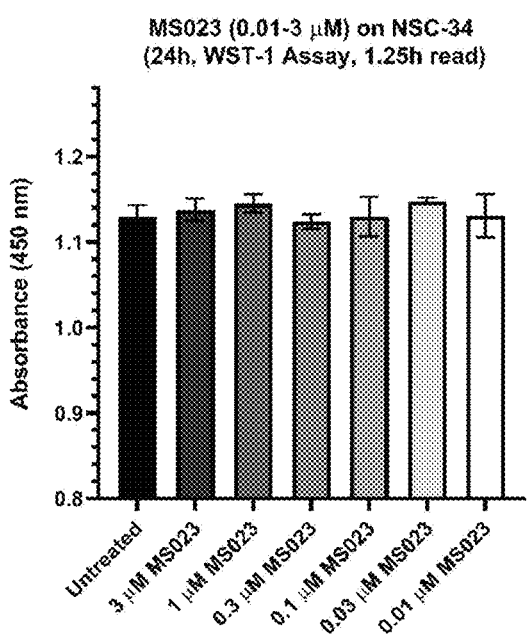
Figure 5A:
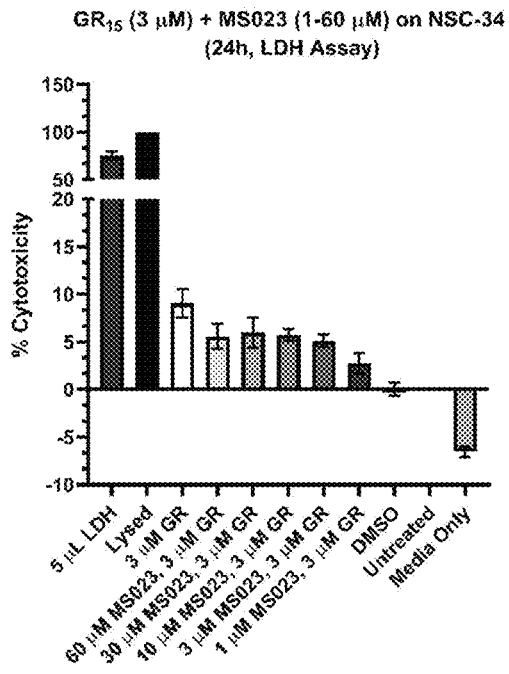
FIGS. 5A-5D are graphs comparing the activity of MS023 (1-60 PM) to abrogate cytotoxicity produced by $GR_{15}$ (SEQ ID NO: 1) (3 µM) (FIGS. 5A and 5B) and $PR_{15}$ (SEQ ID NO: 2) (3 µM) (FIGS. 5C and 5D) measured by LDH assay.
Figure 5B:
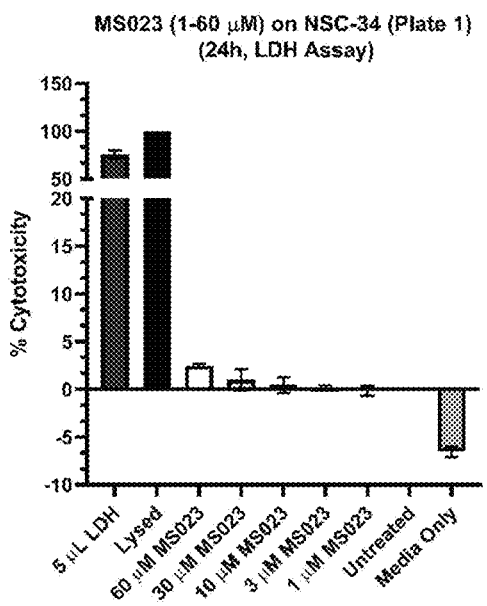
Figure 5C:
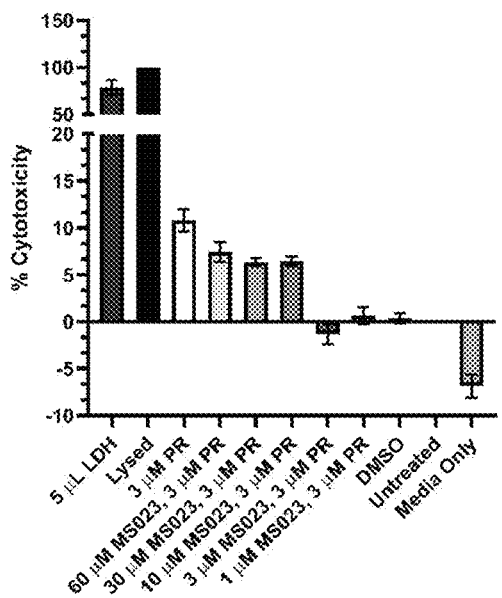
Figure 5D:
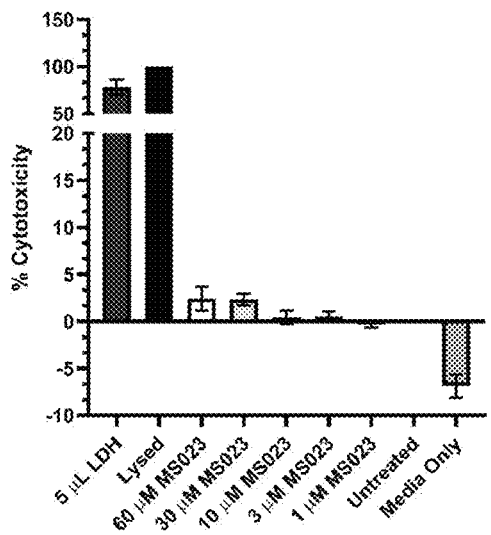
Figure 6A:
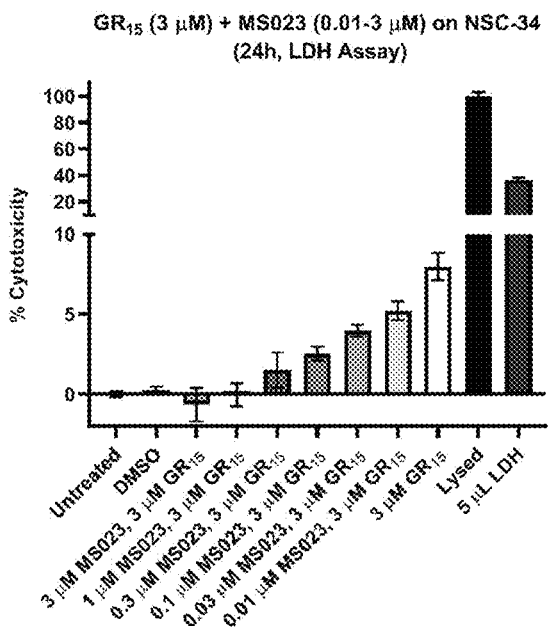
FIGS. 6A-6D are graphs comparing the activity of MS023 (0.01-3 PM) to abrogate cytotoxicity produced by $GR_{15}$ (SEQ ID NO: 1) (3 µM) (FIGS. 6A and 6B) and $PR_{15}$ (SEQ ID NO: 2) (3 µM) (FIGS. 6C and 6D) measured by LDH assay.
Figure 6B:
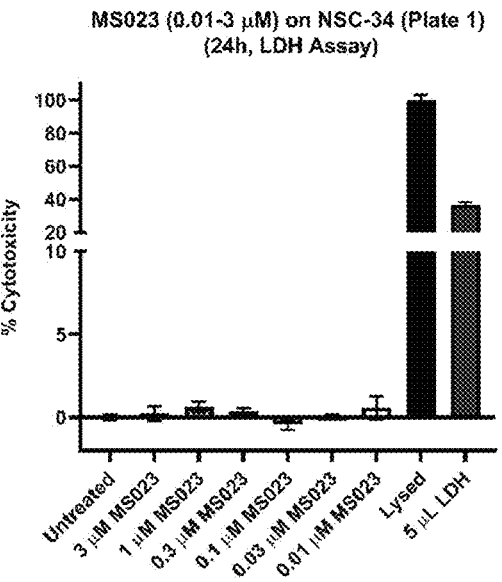
Figure 6C:
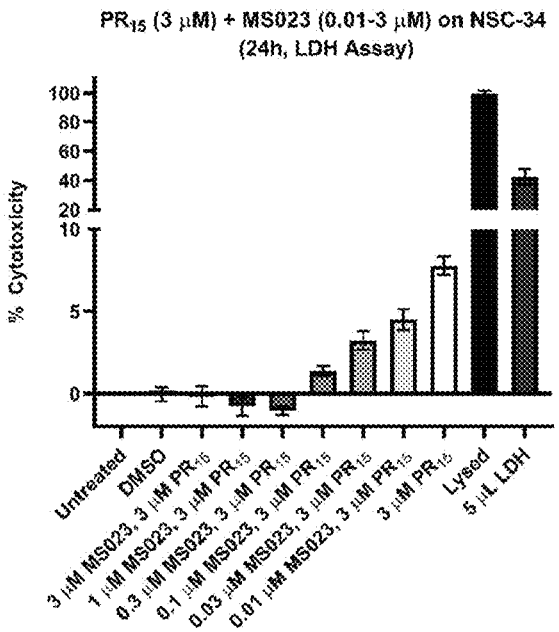
Figure 6D:
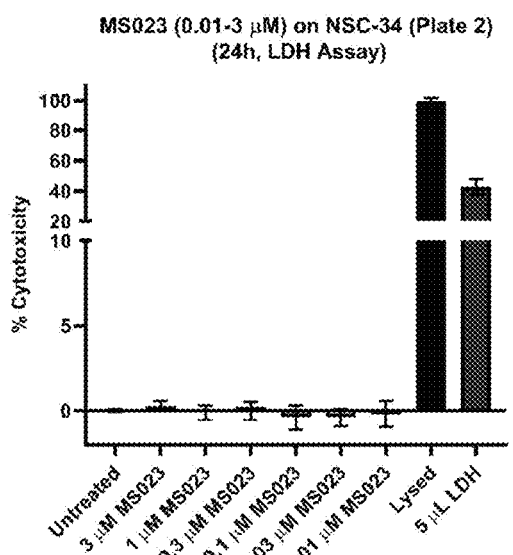
Figure 7A:
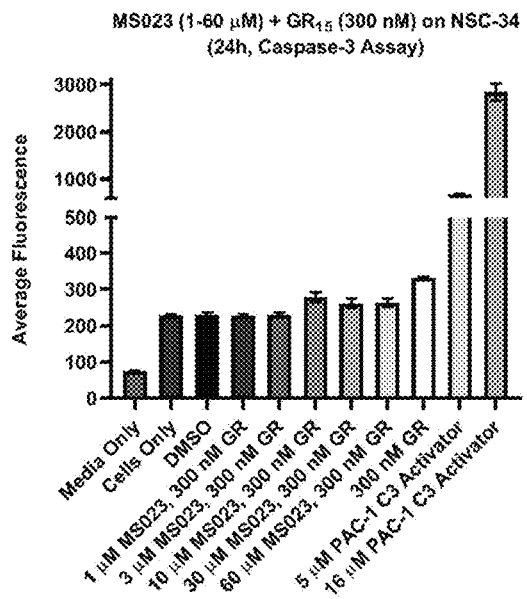
FIGS. 7A-7D are graphs comparing the activity of MS023 (1-60 μM) to abrogate apoptotic activity induced by $GR_{15}$ (SEQ ID NO: 1) (300 nM) (FIGS. 7A and 7B) and $PR_{15}$ (SEQ ID NO: 2) (300 nM) (FIGS. 7C and 7D) measured by Caspase-3 assay.
Figure 7B:
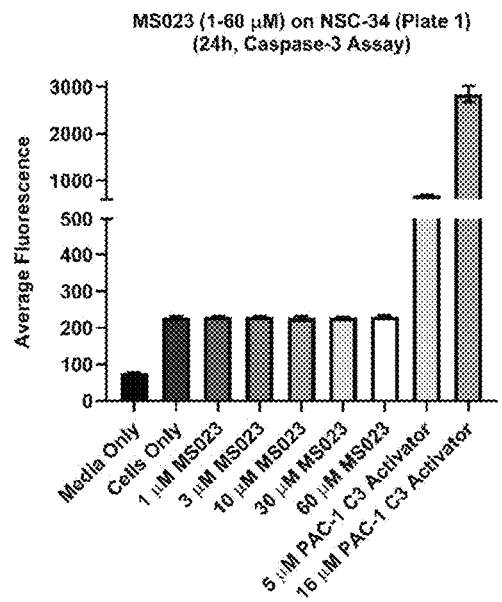
Figure 7C:
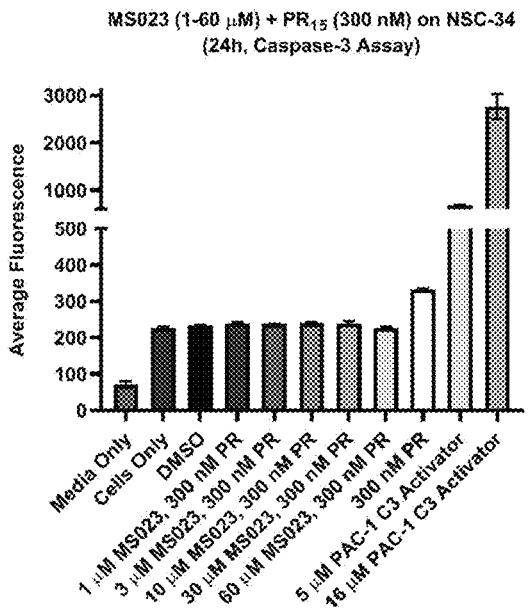
Figure 7D:
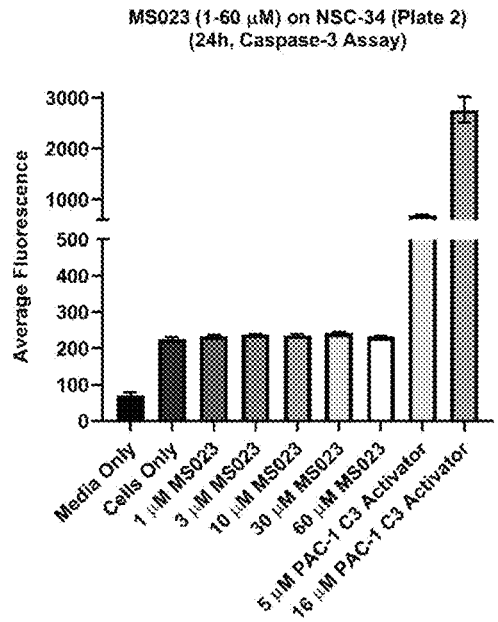
Figure 8A:
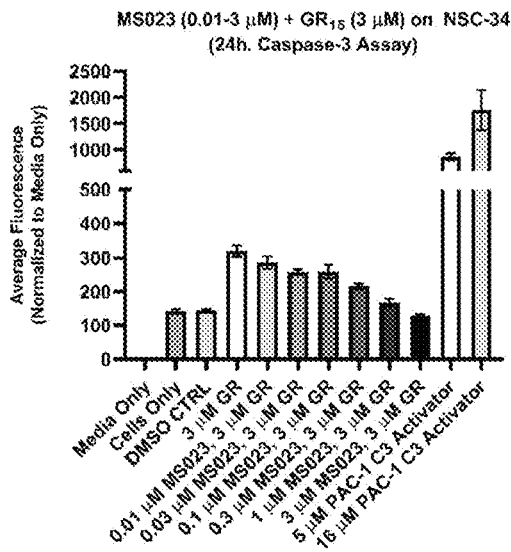
FIGS. 8A-8D are graphs comparing the activity of MS023 (0.01-3 PM) to abrogate apoptotic activity induced by $GR_{15}$ (SEQ ID NO: 1) (3 μM) (FIGS. 8A and 8B) and $PR_{15}$ (SEQ ID NO: 2) (3 μM) (FIGS. 8C and 8D) measured by Caspase-3 assay.
Figure 8B:
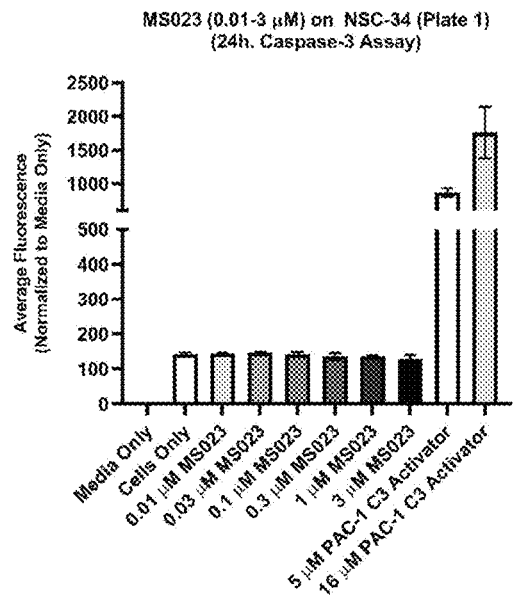
Figure 8C:
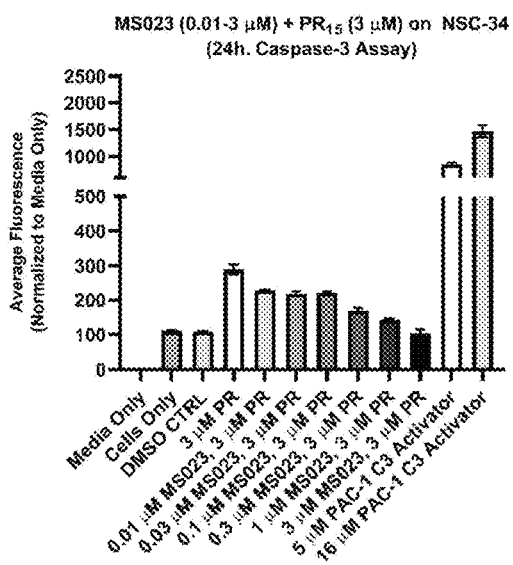
Figure 8D:
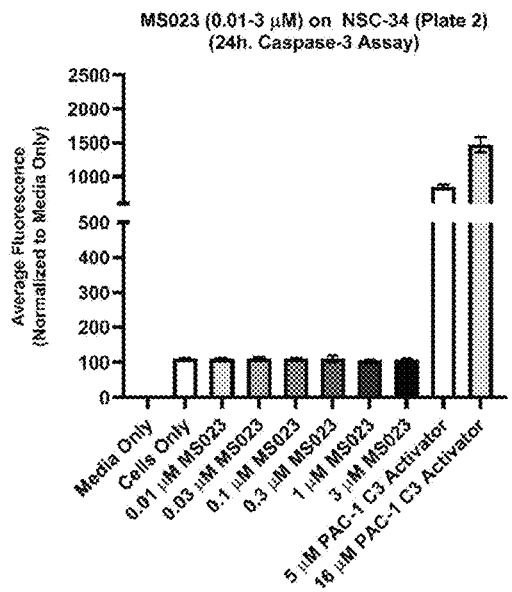
Figure 9A:
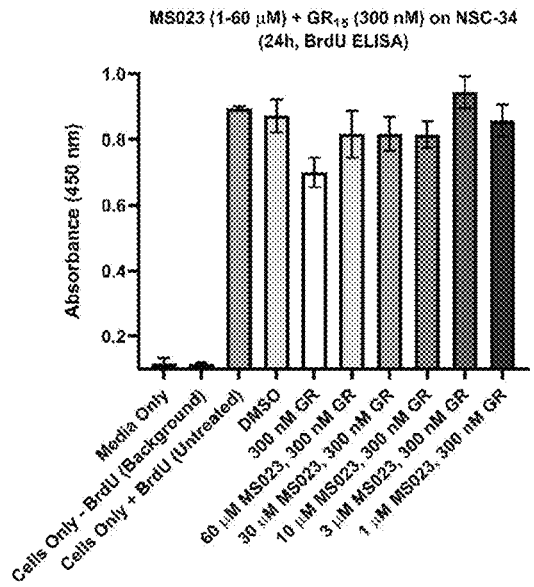
FIGS. 9A-9D are graphs comparing the activity of MS023 (1-60 μM) to abrogate proliferation inhibition induced by $GR_{15}$ (SEQ ID NO: 1) (300 nM) (FIGS. 9A and 9B) and $PR_{15}$ (SEQ ID NO: 2) (300 nM) (FIGS. 9C and 9D) measured by BrdU ELISA.
Figure 9B:
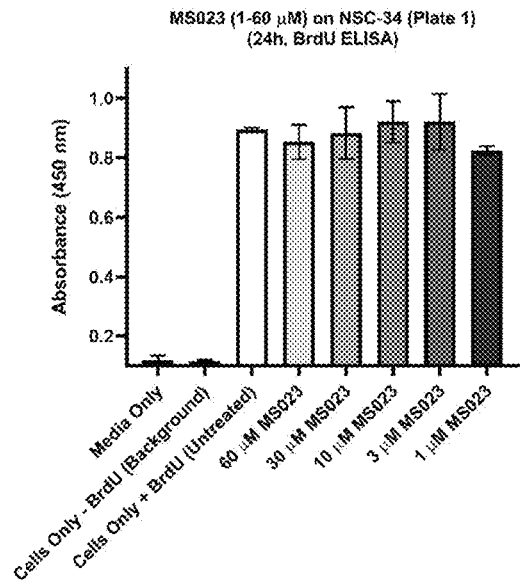
Figure 9C:
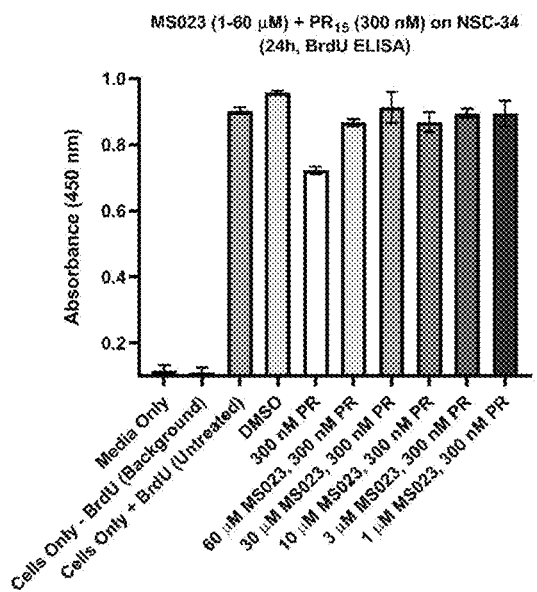
Figure 9D:
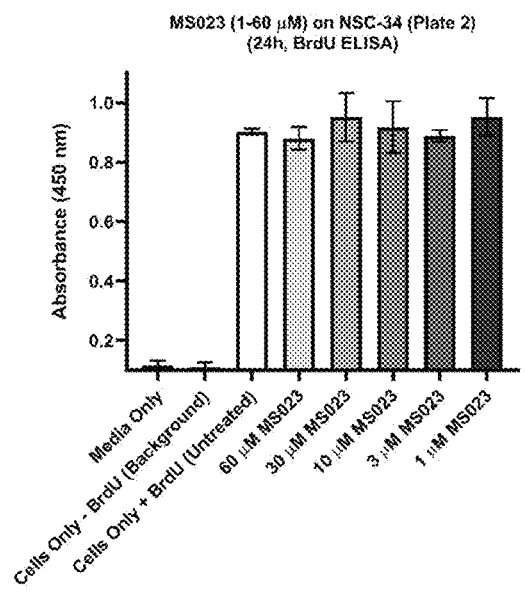

The present invention provides methods of inhibiting DRP-induced toxicity in cells (e.g., to abrogate toxicity produced by asymmetric methylation of the arginine substrates within the dipeptide repeats, such as GR and/or PR) by contacting the cell with an effective amount of a Type I PRMT inhibitor (e.g., an agent that inhibits at least one of PRMT1, PRMT3, PRMT4, PRMT6, or PRMT8, such as MS023, MS049, EPZ020411, GSK715, TP 064, and/or derivatives thereof), wherein cellular dysfunction or cell death is curtailed. Further provided herein are methods of treating neurodegenerative diseases associated with the expression of DRPs (e.g., ALS or FTD) by administering an effective amount of a Type I PRMT inhibitor, as well as the use of Type I PRMT inhibitors in the treating of neurodegenerative diseases, or for the manufacture of a medicament for use in the treating neurodegenerative diseases.

I. Definitions

The following abbreviations are used throughout the specifications and known to those skilled in the art: ALS (amyotrophic lateral sclerosis); FTD (frontotemporal dementia); C9ORF72 (chromosome 9 open reading frame 72); SOD1 (superoxide dismutase-1); and PRMT (protein arginine methyltransferase).

In the description that follows, and in documents incorporated by reference, a number of terms are used extensively. The following definitions are provided to facilitate understanding of the methods and compositions disclosed herein.

As used herein, "dipeptide repeat proteins" (DRPs) refer to peptides consisting of repeating units of two amino acids. Examples of DRPs include the DRPs which are formed when RNA transcribed from the mutated C9ORF72 gene (containing expanded GGGGCC repeats) is translated through a non-AUG initiated mechanism.

DRPs translated from all six reading frames in either the sense or antisense direction of the hexanucleotide repeat result in the expression of five DRPs: glycine-alanine (GA), glycine-arginine (GR), proline-alanine (PA), proline-arginine (PR) and glycine-proline (GP; GP is generated from both the sense and antisense reading frames).

DRPs have been shown to be "toxic" to cells, e.g., by interfering with the normal function of genes (e.g., the C9orf72 gene), as well as interfering with cellular proteins, thus leading to cell dysfunction, degeneration and death. Accordingly, the terms "toxic" and "toxicity" are used interchangeably and refer to the degree to which a substance (e.g., a DRP or a mixture of DRPs) can damage a cell (e.g., a neuronal cell) and/or the organism comprising the cell, such as a human, animal, or bacterium. Such toxic effects include, e.g., loss of cell function and/or cell death.

As used herein, the term "methyltransferases" refers to a class of transferase enzymes that are able to transfer a methyl group from a donor molecule to an acceptor molecule, e.g., an amino acid residue of a protein or a nucleic base of a DNA molecule. Methyltransferases typically use a reactive methyl group bound to sulfur in S-adenosyl methionine (SAM) as the methyl donor. An example of one type of methyltransferase includes the "protein arginine methyltransferases" (PRMTs). PRMTs catalyze the methylation of arginine residues (a common posttranslational modification of proteins). Dimethylation of arginine proceeds via the intermediate ω-NG-monomethylarginine and results in either symmetric ω-NG,N'G-dimethylarginine or asymmetric ω-NG,NG-dimethylarginine. PRMTs are classified into type I and type II enzymes according to their end products. Both classes catalyze the formation of monomethylated arginine. Type I PRMTs convert the intermediate ω-NG-monomethylarginine to asymmetric dimethylarginine, while Type II PRMTs convert the intermediate ω-NG-monomethylarginine to symmetric dimethylarginine. In mammals, Type I PRMTs include PRMT1, PRMT3, PRMT4, PRMT6, and PRMT8.

An "inhibitor" of PRMT (e.g., a Type I PRMT inhibitor) is a molecule that "inhibits" or "blocks" the activity of the PRMT (e.g., Type I PRMT). The terms "inhibits" or "blocks" are used interchangeably and encompass both partial and complete inhibition/blocking by at least about 5%, 10%, 15%, 20%, 30%, 40%, 50%, 60%, 70%, 80%, 90%, 95%, 99%, or 100%, as determined e.g., by methods described herein. Alternatively, inhibition/blocking by an inhibitor (e.g., a Type I PRMT inhibitor) results in an increase in cell activity and/or cell longevity by at least about 5%, 10%, 15%, 20%, 30%, 40%, 50%, 60%, 70%, 80%, 90%, 95%, 99%, or 100%, as determined e.g., by methods described herein. Inhibitors of PRMTs include, e.g., MS023, MS049, EPZ020411, GSK715, and/or TP 064.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. A therapeutically effective amount of the composition may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In reference to the decrease in the toxicity of a cell, an effective amount, e.g., comprises an amount sufficient to restore the rate of cell proliferation to equal that of a healthy, untreated cell, that is not proliferating aberrantly. In reference to the treatment of a neurodegenerative disease (e.g., ALS or FTD), an effective amount is an amount sufficient to prevent or delay symptoms associated with the disease (e.g., muscle weakness and/or cognitive impairment). An effective amount can be administered in one or more administrations. In one example, an "effective amount" is the amount of a Type I PRMT clinically proven to affect a significant improvement in the symptoms associated with the disease (e.g., ALS or FTD).

As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as an mg/kg dose, but rather as an absolute amount of the agent (e.g., the Type I PRMT).

The term "neuronal cell" refers to a specialized, impulse-conducting cell that is the functional unit of the nervous system, consisting of the cell body and its processes, the axon and dendrites. Neuronal cells include sensory neurons, motor neurons, and interneurons.

The term "neural stem cell," or "neural progenitor cell" or "neural precursor cell" refers to cells that can generate progeny that are either neuronal cells (such as neuron precursors or mature neurons) or glial cells (such as glial precursors, mature astrocytes, or mature oligodendrocytes). Typically, the cells express some of the phenotypic markers that are characteristic of the neural lineage.

As used herein, the term "subject" is a human or other animal, e.g., a human having a neurological disorder. In some embodiments, the subjects are mammals.

Examples of subjects can include, but are not limited to, humans, horses, monkeys, dogs, cats, mice, rats, cows, pigs, goats and sheep. In some embodiments, "subjects" are generally human patients diagnosed with ALS or FTD.

The terms "C9ORF72-linked ALS" and "C9ORF72-linked FTD" refer to forms of ALS and FTD, respectively, that afflict individuals who carry expanded hexanucleotide (GGGGCC) repeat mutations, e.g., the C9ORF72 mutation discussed above. In the general population (unaffected by ALS or FTD) open frame region 72 of chromosome 9 will typically exhibit a tract of GGGGCC hexanucleotide repeats between 3 and 10 and almost always fewer than 20 repeats.

Thus, an individual afflicted with ALS or FTD having greater than 20 hexanucleotide repeats, or greater than 30 hexanucleotide repeats, or more, in open frame region 72 of chromosome 9 may suffer from "C9ORF72-linked ALS" or "C9ORF72-linked FTD."

The term "treatment" or "treating" as used herein is intended to encompass preventing the onset, slowing the progression, reversing or otherwise ameliorating a neurological disorder such as a neurodegenerative and/or neuromuscular disorder.

The term "neurodegenerative disease," as used herein, refers to a condition characterized by progressive dysfunction, degeneration and death of specific populations of neurons. Examples of neurodegenerative diseases include, e.g., ALS and FTD, which include "C9ORF72-linked ALS" and "C9ORF72-linked FTD" which can be inherited in an autosomal dominant manner, with age-dependent penetrance.

As used herein and in the appended claims, the singular forms "a," "an," and "the," include plural referents unless the context clearly indicates otherwise. Thus, for example, reference to "a molecule" includes one or more of such molecules and reference to "the method" includes reference to equivalent steps and methods known to those of ordinary skill in the art that could be modified or substituted for the methods described herein.

The term "about" or "approximately" means within an acceptable error range for the particular value as determined by one of ordinary skill in the art, which will depend in part on how the value is measured or determined, e.g., the limitations of the measurement system, or the degree of precision required for a particular purpose. For example, "about" can mean within 1 or more than 1 standard deviations, as per the practice in the art. Alternatively, "about" can mean a range of up to 20%, preferably up to 10%, more preferably up to 5%, and more preferably still up to 1% of a given value. Where particular values are described in the application and claims, unless otherwise stated, the term "about" meaning within an acceptable error range for the particular value should be assumed.

II. Compositions

Further provided are compositions, e.g., pharmaceutical compositions, to be used in the methods of the present invention. Such compositions contain the Type I PRMT inhibitor formulated together with a pharmaceutically acceptable carrier. Type I PRMT inhibitors include, e.g., agents that inhibit PRMT1, PRMT3, PRMT4, PRMT6, and/or PRMT8, such as MS023, MS049, EPZ020411, GSK715, and/or TP 064.

One exemplary Type I PRMT inhibitor is a compound known as MS023, which has the following chemical formula:

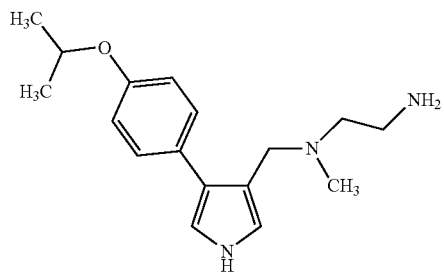 [SMILES: CC(C)Oc1ccc(-c2c[nH]cc2CN(C)CCN)cc1]

Another exemplary Type I PRMT inhibitor is a compound known as MS049, which has the following chemical formula:

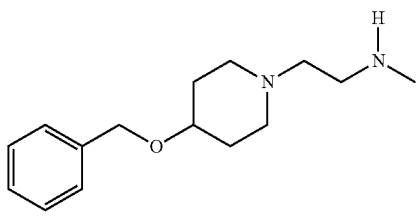 [SMILES: CNCCN1CCC(OCc2ccccc2)CC1]

Another exemplary Type I PRMT inhibitor is a compound known as EPZ020411, which has the following chemical formula:

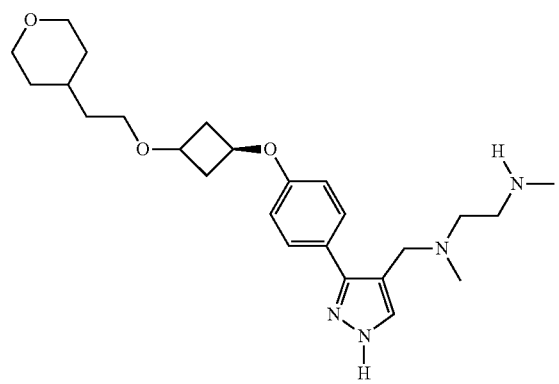

Another exemplary Type I PRMT inhibitor is a compound known as GSK715, which has the following chemical formula:

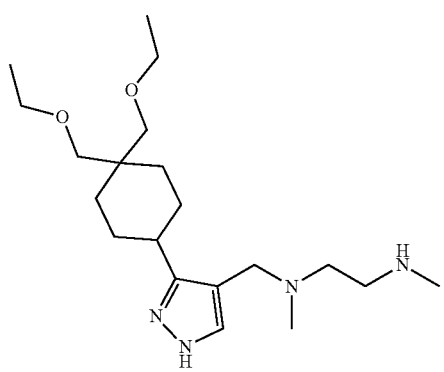 [SMILES: CCOCC1(COCC)CCC(c2n[nH]cc2CN(C)CCNC)CC1]

Another exemplary Type I PRMT inhibitor is a compound known as TP 064, which has the following chemical formula:

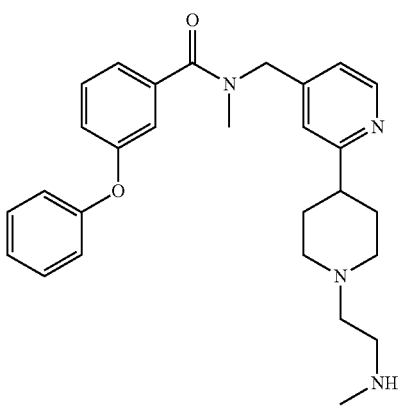 [SMILES: CNCCN1CCC(c2cc(CN(C)C(=O)c3cccc(Oc4ccccc4)c3)ccn2)CC1]

More generally, Type I PRMT inhibitors can also include, for example, compounds described in U.S. Patent Applications Pub. Nos. US2016/0137609 and US2019/0077795, both assigned to Epizyme, Inc. of Cambridge Mass. or US20100151506, assigned to University of South Carolina, the disclosures of which are herein incorporated by reference in their entireties.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent. Examples of pharmaceutically acceptable carriers are solvents, diluents, dispersion media, suspension aids, surface active agents, preservatives, solid binders, stabilizers, fillers, binding agents, lubricants, coatings, antibacterial and antifungal agents, isotonic and absorption delaying agents, and the like that are physiologically compatible. Various vehicles and carriers used in formulating pharmaceutical compositions and known techniques for the preparation thereof are disclosed in Remington's Pharmaceutical Sciences (A. Osol et al. eds., 15th ed. 1975). Pharmaceutically acceptable carriers may further comprise minor amounts of auxiliary substances such as wetting or emulsifying agents, preservatives or buffers, which enhance the shelf life or effectiveness of the pharmacological agent.

Pharmaceutically acceptable carriers also include pharmaceutically acceptable salts, where the term "pharmaceutically acceptable salts" includes salts of the active compounds which are prepared with relatively nontoxic acids or bases, depending on the particular substituents found on the compounds described herein. Pharmaceutically acceptable salts include, but are not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentismate, fumarate, gluconate, glucaronate, saccharate, formate, benzoate, glutamate, methanesulfonate, ethanesulfonate, benzenesulfonate, p-toluensulfonate, bicarbonate, malonate, mesylate, esylate, napsydisyfate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron sails. The present invention also includes quaternary ammonium salts of the compounds described herein, where the compounds have one or more tertiary amine moiety.

Such carriers enable the compounds of the invention to be formulated as tablets, pills, dragees, capsules, liquids, gels, syrups, slurries, suspensions and the like, for oral ingestion by a patient to be treated. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. In one embodiment, mannitol and magnesium stearate are used as pharmaceutically acceptable carriers.

In some preferred embodiments, the compound of the present invention is administered with an adjuvant. The term "adjuvant" can be a compound that lacks significant activity administered alone but can potentiate the activity of another therapeutic agent. In some embodiments, an adjuvant is selected from the group consisting of buffers, anti-microbial preserving agents, surfactants, antioxidants, tonic regulators, antiseptics, thickeners and viscosity improvers.

The pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. In one embodiment, the preferred mode of administration is oral delivery.

Various solid oral dosage forms can be used for administering compounds of the invention including such solid forms as tablets, gelcaps, capsules, caplets, granules, lozenges and bulk powders.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (I.e., the pharmacological agent) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Supplementary active compounds can also be incorporated into the compositions. In certain embodiments, the Type I PRMT inhibitor is co-formulated with and/or co-administered with one or more additional therapeutic agents that are useful for improving the pharmacokinetics of the pharmacological agent and/or treating degenerative diseases.

III. Methods

Provided herein are clinical methods for treating a neurodegenerative disease including administration of a Type I PRMT inhibitor by a variety of methods known in the art. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In one embodiment, an initial bolus dose followed by smaller maintenance doses is administered. It is especially advantageous to formulate the compositions in dosage unit form for ease of administration and uniformity of dosage.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Suitable treatment protocols for treating a neurodegenerative disease (e.g., ALS or FTD) in a human patient include, for example, administering to the patient an effective amount of a Type I PRMT inhibitor that results in a reduction, amelioration, palliation, lessening, delaying, and/or alleviation of one or more of the signs, symptoms, or causes of the disease (e.g., a decrease in muscle weakness), or any other desired alteration of a biological system. Alternatively, the Type I PRMT inhibitor is administered at a flat dose of about 0.01, 0.03, 0.1, 0.3, 1, or 3.0 µM, preferably about 1.0 µM or 3.0 µM.

In other embodiments, the dose of the Type I PRMT inhibitor is calculated per body weight, e.g., mg/kg body weight. In another embodiment, the dose of the Type I PRMT inhibitor is a flat-fixed dose. In another embodiment, the dose of the Type I PRMT inhibitor is varied over time. For example, the Type I PRMT inhibitor may be initially administered at a high dose and may be lowered over time. In another embodiment, the Type I PRMT inhibitor antibody is initially administered at a low dose and increased over time.

In another embodiment, the amount of the Type I PRMT inhibitor administered is constant for each dose. In another embodiment, the amount of inhibitor administered varies with each dose. For example, the maintenance (or follow-on) dose of the inhibitor can be higher or the same as the loading dose which is first administered. In another embodiment, the maintenance dose of the inhibitor can be lower or the same as the loading dose.

The following examples are merely illustrative and should not be construed as limiting the scope of this disclosure in any way as many variations and equivalents will become apparent to those skilled in the art upon reading the present disclosure.

The contents of all references, GenBank entries, patents and published patent applications cited throughout this application are expressly incorporated herein by reference.

The present invention is further illustrated by the following examples which should not be construed as further limiting. The contents of all figures and all references, patents, and published patent applications cited throughout this application are expressly incorporated herein by reference.

EXAMPLES

Materials and Methods

The following materials and methods were used in the examples described below.

WST-1 Assay: The WST-1 assay is a colorimetric assay that measures cell metabolism. Cells with a healthy metabolism contain mitochondrial dehydrogenase enzymes that remove hydrogen atoms from certain molecules, resulting in a release of energy that the cell can use to perform critical reactions. In the WST-1 assay, a water soluble tetrazolium salt substrate (known as WST-1) is applied, which readily enters cells and their mitochondria upon application. If cells are viable, their mitochondrial dehydrogenase enzymes will catalyze the reaction to convert this WST-1 substrate to a colored product called Formazan. The production of this colored Formazan product by viable cells can be quantified using a spectrophotometer (plate reader). Higher absorbance readings correspond to greater metabolic activity/cell viability.

LDH Assay: The LDH assay is a colorimetric assay that measures cell toxicity and death. When cells are exposed to cytotoxic compounds, they may undergo a type of cell death called necrosis, which first results in cell swelling and a loss in cell membrane integrity. When cells lose membrane integrity, an enzyme found in living cells called lactate dehydrogenase (LDH) is released into the solution surrounding the dying cell. A form of programmed cell death, apoptosis, as well as other forms of cell death also ultimately lead to a cell's membrane being destroyed, resulting in a large release of LDH into the extracellular space. Thus, LDH is an excellent marker not only for necrosis, but for all instances of cell death. In an LDH assay, a sample of the solution surrounding the cell is isolated, and transferred to a plate containing an LDH reaction mixture. This reaction mixture contains a tetrazolium salt intermediate and other reaction constituents that, when exposed to LDH, convert the tetrazolium salt into a colored Formazan product. This Formazan product can be quantified spectrophotometrically. Greater absorbance readings correspond to more cell death.

Caspase-3/CPP32 Assay: The caspase-3 assay is a fluorometric assay that measures apoptotic cell death. Apoptosis is a form of "programmed" cell death, in which a certain family of proteins inside the cell triggers a cascade of chemical reactions that result in the cell killing itself. One family of proteins involved in this process is the caspase protein family. Of the caspase proteins, caspase-2, 8, 9, and 10 are known as "initiators," those that trigger the death cascade, and caspase-3, 6, and 7 are known as "executioners," which carry out the actual killing of the cell. In a caspase-3 assay, cells treated with test compounds are lysed, and a substrate known as DEVD-AFC is added to the lysate. If active caspase-3 enzyme is present in the lysate, it will cleave AFC from the DEVD-AFC substrate, resulting in a fluorescent signal that can be quantified using a fluorescence microtiter plate reader. Thus, the apoptotic activity of cells treated with test compounds can be quantified. Greater fluorescence readings correspond to more apoptotic cell death.

BrdU ELISA: The BrdU ELISA is an ELISA detecting cell proliferation activity. BrdU is a pyrimidine analog that, when inside the cell, can be incorporated instead of thymidine into newly synthesized strands of DNA. Just as is indicated by thymidine incorporation into DNA, BrdU incorporation into cell DNA indicates DNA synthesis activity, which is required for cell proliferation. In the BrdU ELISA, cells are treated with test compounds as well as BrdU reagent, and then incubated for 24 hours before testing. During testing, an anti-BrdU antibody detects the incorporation of BrdU into cell DNA that occurred over the 24-hour period, as a surrogate for cell proliferation activity. This anti-BrdU antibody is then labelled with a secondary antibody tagged with a colored substrate, which can be quantified spectrophotometrically. Greater absorbance readings correspond to more cell proliferation activity.

PRMT Inhibitors: Type I and Type II PRMT inhibitors were tested in the examples as listed in Table 1. See also FIG. 33 which summarizes the IC50s for inhibition of dimethylation activity and EC50s for abrogation of toxicity caused by $GR_{15}$ (SEQ ID NO: 1) or $PR_{15}$ (SEQ ID NO: 2) challenge, and chemical structures for each compound tested.

TABLE 1

| Name(s) | Supplier | Molecular Formula | Molecular Weight (g) | Purity (HPLC) | Stated Function |
| --- | --- | --- | --- | --- | --- |
| GSK591 EPZ015866 GSK3203591 | Tocris Bioscience | $C_{22}H_{26}N_4O_2 \cdot 2HCl$ | 471.43 | ≥97% | Potent and selective PRMT5 inhibitor |
| MS023 | Tocris | $C_{17}H_{25}N_3O \cdot 2HCl$ | 369.33 | ≥98% | Potent and selective inhibitor of all Type 1 PRMTs |
| MS049 | Cayman | $C_{15}H_{24}N_2O \cdot 2HCl$ | 321.3 | ≥98% | Potent and selective inhibitor of PRMT4, less active against other Type I PRMTs. |
| EPZ020411 | Cayman Chemical | $C_{25}H_{38}N_4O_3$ | 442.6 | ≥98% | An inhibitor of protein arginine methyltranferase 6 that less potently targets PRMT1 and PRMT8 |
| GSK715 GSK3368715 EPZ019997 | MedChem Express | $C_{20}H_{38}N_4O_2$ | 366.54 | 99.49 | An orally active, reversible, and S-adenosyl-L-methionine (SAM) uncompetitive type I protein arginine methyltransferases (PRMTs) inhibitor |
| TP 064 | Tocris | $C_{28}H_{34}N_4O_2 \cdot \frac{1}{2}H_2O$ | 467.61 | ≥99.5% | Potent and selective PRMT4 inhibitor |

Synthetic Dipeptide Repeat Proteins (DRPs): DRP toxicity was induced by administration of 15 mer dipeptide repeat sequences of GR, PR, GP, or PA to cells.

TABLE 2

| Supplier | Sequence | SEQ ID NO | Purity (%) | Molecular Weight (g) | Solubilized in | [Stock] | Stored at (° C.) |
| --- | --- | --- | --- | --- | --- | --- | --- |
| GenicBio | $(GR)_{15}$ | 1 | 94.53 | 3216.57 | Sterile DMSO | 10 mM | 4 |
| GenicBio | $(PR)_{15}$ | 2 | 93.17 | 3817.53 | Sterile DMSO | 10 mM | 4 |

TABLE 2-continued

| Supplier | Sequence | SEQ ID NO | Purity (%) | Molecular Weight (g) | Solubilized in | [Stock] | Stored at (° C.) |
|---|---|---|---|---|---|---|---|
| GenicBio | (GP)$_{15}$ | 3 | 94.49 | 2330.56 | Sterile DMSO | 10 mM | 4 |
| GenicBio | (PA)$_{15}$ | 4 | 90.75 | 2540.91 | Sterile DMSO | 10 mM | 4 |

NSC-34 Cell Culture: NSC-34 cells (Cedarlane Laboratories, Burlington, ON, CA) were cultured in a complete medium consisting of High Glucose Dulbecco's Modified Eagle Medium (Millipore-Sigma, Burlington, Mass., USA) supplemented with 10% US-origin fetal bovine serum (Thermo-Fisher Scientific, Cambridge, Mass., USA), 1% 200 mM L-Glutamine solution (Thermo-Fisher Scientific, Cambridge, Mass., USA), and 1% 10,000 U/mL Penicillin-Streptomycin solution (Thermo-Fisher Scientific, Cambridge, Mass., USA). Prior to preparation of NSC-34 complete medium, L-Glutamine and Penicillin-Streptomycin solutions were aliquoted and stored at −20° C., and DMEM/High Glucose was stored at 4°. At each passage, cells were washed once with Dulbecco's Phosphate-Buffered Saline with Calcium and Magnesium (Thermo-Fisher Scientific, Cambridge, Mass., USA) and treated with 0.25% Trypsin-EDTA solution (Thermo-Fisher Scientific, Cambridge, Mass., USA) for 5 minutes at 37° C., 5% $CO_2$ for dissociation. Prepared complete medium, DPBS, and Trypsin were always heated in a 37° C. water bath before use, and stored at 4° C. between uses. Cell counts for plating were performed using a Hausser Scientific cell counting chamber (Thermo-Fisher Scientific, Cambridge, Mass., USA).

Preparation of Exogenous Dipeptide Repeat Protein Solutions: Synthesized proteins GR$_{15}$ (SEQ ID NO: 1) and PR$_{15}$ (SEQ ID NO: 2)(GenicBio Limited, Kowloon, Hong Kong, CN), and ADMe-GR$_{15}$ (SEQ ID NO: 1)(Eurogentec, Leige, BE) were purchased as lyophilized powders and stored at −20° C. in a desiccator prior to reconstitution. Proteins were reconstituted in sterile DMSO (Millipore-Sigma, Burlington, Mass., USA) to stock concentrations of 10 mM, and stored at 4° C.

Preparation of PRMT Inhibitor Solutions: Small-molecule PRMT inhibitors MS023 and GSK591 (Tocris Bioscience, Briston, UK), MS049 (an inert analog of MS023) and EPZ020411 (Cayman Chemical, Ann Arbor, Mich., USA), GSK3368715 (Medchem Express, Monmouth Junction, N.J., USA), and negative control MS094 (Millipore-Sigma, Burlington, Mass., USA) were purchased and stored at −20° C. prior to and following reconstitution. After reconstitution using the solvents specified in Table _____, stocks were aliquoted to 15-20 μL and immediately stored at −20° C.

TABLE 3

Small Molecule PRMT Inhibitor Details

| Drug Name(s) | Vendor Catalog # | Type of PRMT Inhibitor | Solvent Used to Reconstitute | Stock Concentration |
|---|---|---|---|---|
| GSK591 GSK3203591 EPZ015866 | 5777/10 | Type II (Symmetric) | DMSO | 10 mM |
| MS023 | 5713 | Type I (Asymmetric) | Water | 10 mM |
| MS094 | SML2548 | Inactive | DMSO | 10 mM |
| MS049 | 18348 | Type I (Asymmetric) | Water | 10 mM |
| EPZ020411 | 19160 | Type I (Asymmetric) | DMSO | 10 mM |
| GSK715 GSK3368715 EPZ019997 | HY-128717A | Type I (Asymmetric) | DMSO | 10 mM |

Plating NSC-34 and Dosing with DRPs and PRMT Inhibitors: NSC-34 cells were plated at a density of 3.77×10$^4$ cells per well in clear, flat-bottom, full volume, 96-well tissue culture-treated plates (Thermo-Fisher Scientific, Cambridge, Mass., USA). One row on the top and bottom of the plate, and two columns on either side of the plate, were left without cells and contained culture medium only to minimize experimental well volume evaporation. After plating, cells were incubated for 24h at 37° C., 5% $CO_2$ prior to DRP and/or PRMT inhibitor addition. At time of DRP/PRMT inhibitor addition, desired doses of DRP for challenge and inhibitor for treatment were achieved by diluting aliquots of each stock in warm culture medium. During experiments where both PRMT inhibitors and DRPs were used, PRMT inhibitors were always applied to wells first, and followed by DRP application. Vehicle controls were included as wells treated with equivalent DMSO concentrations to those that had been DRP-treated, drug treated, or both. Inhibitor toxicity controls were included as wells treated with the desired doses of drug for the experiment, but no DRP. DRP toxicity controls were included as wells only treated with the doses of DRP used for challenge. Once dosed, plates were incubated for 24h at 37° C., 5% $CO_2$ prior to running the WST-1 or LDH assay endpoints. Additional controls needed for each endpoint are specified in the "WST-1 Assay" and "LDH Assay" sections of these methods.

WST-1 Assay: Cells were plated and prepared using the steps described in the "Plating NSC-34 and Dosing with DRPs and PRMT Inhibitors" section of these methods. Other controls for this experiment included wells containing only cells in culture medium, and culture medium only. At time of testing, culture medium was removed from wells and replaced with a warmed, sterile-filtered solution consisting of DPBS with calcium and magnesium, and 4.5 g/L D-glucose (Millipore-Sigma, Burlington, Mass., USA). To wells containing 200 µL DPBS-glucose solution, 20 µL/well WST-1 reagent (Millipore-Sigma, Burlington, Mass.) was applied and plates were then incubated at 37° C., 5% $CO_2$ for 1h before plates were read at 450 nm on a SpectraMax M3 Microplate Reader (Molecular Devices, San Jose, Calif., USA). Experiments included three replicates per condition. Each experiment was repeated twice (executed three times total).

LDH Assay: Cells were plated and prepared using the steps described in the "Plating NSC-34 and Dosing with DRPs and PRMT Inhibitors" section of these methods. Other controls for this experiment included several sets of wells with only cells in culture medium (one triplicate designated for "untreated," one triplicate designated for "lysed" positive control), and wells with culture medium only. An additional control added only to the transfer plate at time of testing was 5 µL LDH only. Testing was performed using colorimetric LDH-Cytotoxicity Assay Kit II (Abcam, Cambridge, Mass., USA) per manufacturer's instructions. Final read at 450 nm was performed on a SpectraMax M3 Microplate Reader (Molecular Devices, San Jose, Calif., USA). Data analysis included calculation of % LDH release using the following equation:

$$\% \; LDH \; Release = \frac{\left(\begin{array}{c} A450 \; Test \; Condition- \\ A450 \; Untreated \; Control \end{array}\right)}{\left(\begin{array}{c} A450 \; Lysed \; Control- \\ A450 \; Untreated \; Control \end{array}\right)} * 100\%$$

Experiments included three replicates per condition. Each experiment was repeated twice (executed three times total).

Example 1: Comparison of MS023 (PRMT Type I Inhibitor) and GSK591 (PRMT Type II, Specifically PRMT5 Inhibitor) to Abrogate Dysmetabolism Induced by 3 µM $GR_{15}$ (SEQ ID NO: 1) in NSC-34 Motor-Neuron-Like Cells Measured by WST-1 Assay Cells were plated in culture medium in 2 96-well plates at a density of $3.7\times10^4$ cells per well, and incubated overnight at 37° C., 5% $CO_2$. The following day, immediately prior to addition of test compounds, existing culture medium was removed and replaced with staggered volumes of culture medium corresponding to the treatments each well would receive (to ensure the final volume in all wells was 200 µL after treatment). A 10 mM stock of MS023 was thawed to room temperature and diluted in warm culture medium to achieve final concentrations of 60, 30, 10, 3, and 1 µM in plate. Following the same protocol, a 10 mM stock of GSK591 was thawed to room temperature and diluted in warm culture medium to achieve final concentrations of 200, 100, 33, 10, and 3 µM in plate. Additionally, a 10 mM stock of $GR_{15}$ (SEQ ID NO: 1) was equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Untreated (Cells only in culture medium)
DMSO Control (Cells treated only with the amount of DMSO that
GR-treated cells were exposed to)
GR Only (Cells treated only with 3 µM $GR_{15}$) (SEQ ID NO: 1)
Cells treated with 3 µM $GR_{15}$ (SEQ ID NO: 1) and one of the following doses of MS023: 60 µM, 30 µM, 10 µM, 3 µM, 1 µM.
Cells treated with only one of the following doses of MS023: 60 µM, 30 µM, 10 µM, 3 µM, 1 µM.
Cells treated with 3 µM $GR_{15}$ (SEQ ID NO: 1) and one of the following doses of GSK591: 200 µM, 100 µM, 33 µM, 10 µM, 3 µM.
Cells treated with only one of the following doses of GSK591: 200 µM, 100 µM, 33 µM, 10 µM, 3 µM.

Plates were incubated for 24h at 37° C., 5% $CO_2$. Immediately before testing, culture medium was removed and replaced with 200 µL PBS-Glucose solution (4.5 g/L, sterile) that had been warmed from 4° C. in a 37° C. water bath for 10 minutes before use. WST-1 reagent aliquots were thawed from −20° C. and equilibrated to room temperature before use. 20 µL WST-1 reagent was added per well containing 200 µL PBS-Glucose. Plates were incubated with WST-1 at 37° C., 5% $CO_2$ for 1.25 hours, with absorbance readings (450 nm) taken on a Molecular Devices Plate Reader (SpectraMax M3) every 15 minutes. Data was exported from plate reader's SoftMax Pro 7.0 software into an excel file.

As shown in FIGS. 1A-1D, PRMT Type I inhibitor MS023 abrogated GR-induced dysmetabolism in NSC-34 motor-neuron-like cells at a dose of 3 µM. PRMT5 (a Type II PRMT) inhibitor GSK591 did not abrogate GR-induced dysmetabolism at any tested doses.

Example 2: MS023 (PRMT Type I Inhibitor) Abrogates Dysmetabolism Induced by 3 µM $GR_{15}$ (SEQ ID NO: 1) or 3 µM $PR_{15}$ (SEQ ID NO: 2) in NSC-34 Motor-Neuron-Like Cells Measured by WST-1 Assay Cells were plated and incubated overnight as in Example 1. The following day, immediately prior to addition of test compounds, existing culture medium was removed and replaced with staggered volumes of culture medium as in Example 1. A 10 mM stock of MS023 was thawed to room temperature and diluted as in Example 1. Additionally, a 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Untreated (Cells only in culture medium)
DMSO Control (Cells treated only with the amount of DMSO that GR- and PR-treated cells were exposed to)
GR Only (Cells treated only with 3 µM $GR_{15}$) (SEQ ID NO: 1)
Cells treated with 3 µM $GR_{15}$ (SEQ ID NO: 1) and one of the following doses of MS023: 60 µM, 30 µM, 10 µM, 3 µM, 1 µM.

PR Only (Cells treated only with 3 μM PR$_{15}$) (SEQ ID NO: 2)

Cells treated with 3 μM PR$_{15}$ (SEQ ID NO: 2) and one of the following doses of MS023: 60 μM, 30 μM, 10 μM, 3 μM, 1 μM.

Cells treated with only one of the following doses of MS023: 60 μM, 30 μM, 10 μM, 3 μM, 1 μM.

Plates were incubated for 24h at 37° C., 5% CO$_2$. Immediately before testing, culture medium was removed and replaced with 200 μL PBS-Glucose solution (4.5 g/L, sterile) that had been warmed from 4° C. in a 37° C. water bath for 10 minutes before use. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% CO$_2$ for 1 hour, with absorbance readings (450 nm) taken on a Molecular Devices Plate Reader (SpectraMax M3) every 15 minutes. Data was exported from plate reader's SoftMax Pro 7.0 software into an excel file.

As shown in FIGS. 2A-2D, 3 μM and 1 μM doses of MS023 (Type I PRMT inhibitor) completely abrogated dysmetabolism in NSC-34 induced by 3 μM doses of either GR$_{15}$ (SEQ ID NO: 1) or PR$_{15}$. (SEQ ID NO: 2) These doses also abrogated dysmetabolism completely in the previous experiment (see Example 1).

Example 3: Effect of Lower Dose Ranges (0.01-3 μM) of MS023 (Type I PRMT Inhibitor) on Abrogation of Dysmetabolism Induced by 3 μM Doses of GR$_{15}$ (SEQ ID NO: 1) or PR$_{15}$ (SEQ ID NO: 2) Measured by WST-1 Assay Cells were plated in culture medium as in Example 1. The following day, immediately prior to addition of test compounds, existing culture medium was removed and replaced with staggered volumes of culture medium as in Example 1. A 10 mM stock of MS023 was thawed to room temperature and diluted in warm culture medium to achieve final concentrations of 3, 1, 0.3, 0.1, 0.03, and 0.01 μM in plate. A 10 mM stock of GR$_{15}$ (SEQ ID NO: 1) and a 10 mM stock of PR$_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Untreated (Cells only in culture medium)
DMSO Control (Cells treated only with the amount of DMSO that GR- and PR-treated cells were exposed to)
GR Only (Cells treated only with 3 μM GR$_{15}$) (SEQ ID NO: 1)
Cells treated with 3 μM GR$_{15}$ (SEQ ID NO: 1) and one of the following doses of MS023: 3 μM, 1 μM, 0.3 μM, 0.1 μM, 0.03 μM, 0.01 μM.
PR Only (Cells treated only with 3 μM PR$_{15}$) (SEQ ID NO: 2)
Cells treated with 3 μM PR$_{15}$ (SEQ ID NO: 2) and one of the following doses of MS023: 3 μM, 1 μM, 0.3 μM, 0.1 μM, 0.03 μM, 0.01 PM.
Cells treated with only one of the following doses of MS023: 3 μM, 1 μM, 0.3 μM, 0.1 μM, 0.03 μM, 0.01 μM.

Plates were incubated for 24h at 37° C., 5% CO$_2$. Immediately before testing, culture medium was removed and replaced with 200 μL PBS-Glucose solution (4.5 g/L, sterile) that had been warmed from 4° C. in a 37° C. water bath for 10 minutes before use. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% CO$_2$ for 1 hour, with absorbance readings (450 nm) taken on a Molecular Devices Plate Reader (SpectraMax M3) every 15 minutes. Data was exported from plate reader's SoftMax Pro 7.0 software into an excel file.

As shown in FIGS. 3A-3D, MS023 abrogates 3 μM GR$_{15}$ (SEQ ID NO: 1) and PR$_{15}$-(SEQ ID NO: 2) induced dysmetabolism in a dose-dependent manner. Dose-dependent metabolic abrogate profiles slightly varied by dipeptide repeat protein: significant partial abrogate of metabolic activity in GR-treated cells is seen at MS023 doses as low as 0.1 μM, whereas in PR-treated cells, it was seen at MS023 doses as low as 0.3 μM. In other words, MS023 more potently abrogated GR-induced dysmetabolism in this assay.

Example 4: MS023 (1-60 μM) and Abrogation of Cytotoxicity Produced by GR$_{15}$ (SEQ ID NO: 1) and PR$_{15}$ (SEQ ID NO: 2) (300 nM) Measured by LDH Assay Cells were plated in culture medium as in Example 1. The following day, immediately prior to addition of test compounds, existing culture medium was removed and replaced with staggered volumes of culture medium as in Example 1. A 10 mM stock of MS023 was thawed to room temperature and diluted as in Example 1. A 10 mM stock of GR$_{15}$ (SEQ ID NO: 1) and a 10 mM stock of PR$_{15}$ (SEQ ID NO: 2) were equilibrated to room temperature and diluted in warm culture medium to achieve a final concentration of 300 nM in wells.

The following conditions were plated in triplicate. Samples were surrounded by border wells on the outside of the plate filled with sterile Phosphate-buffered saline to prevent evaporation of volume in experimental wells during incubation:

Background (Culture medium only)
Low control/"0% toxicity" (Cells only in culture medium)
DMSO Control (Cells treated only with the amount of DMSO that GR- and PR-treated cells were exposed to)
GR Only (Cells treated only with 300 nM GR$_{15}$) (SEQ ID NO: 1)
Cells treated with 300 nM GR$_{15}$ (SEQ ID NO: 1) and one of the following doses of MS023: 60 μM, 30 μM, 10 μM, 3 μM, 1 μM.
PR Only (Cells treated only with 300 nM PR$_{15}$) (SEQ ID NO: 2)
Cells treated with 300 nM PR$_{15}$ (SEQ ID NO: 2) and one of the following doses of MS023: 60 μM, 30 μM, 10 μM, 3 μM, 1 μM.
Cells treated with only one of the following doses of MS023: 60 μM, 30 μM, 10 μM, 3 μM, 1 μM.
High control/"100% toxicity" (Cells lysed with lysis buffer)
Positive control (5 μL LDH solution).

Plates were incubated for 24h at 37° C., 5% CO$_2$. Cells were tested and data were analyzed by LDH assay.

As shown in FIGS. 4A-4D, when applied to NSC-34 cells treated with a 300 nM dose of GR$_{15}$, (SEQ ID NO: 1) the two highest doses of MS023 (60, 30 μM) significantly amplified cytotoxicity in an LDH assay. This phenotype was not seen in NSC-34 cells treated with 300 nM PR$_{15}$, (SEQ ID NO: 2) where all doses of MS023 applied at least partially abrogated PR-induced cytotoxicity. These results suggest differences in the mechanisms of action among the two arginine-rich DRPs. This phenomenon was only observed at 300 nM and not 3 μM doses (data to be shown in Experiment 5) of each protein.

Example 5: MS023 (1-60 μM) and Abrogation of Cytotoxicity Produced by $GR_{15}$ (SEQ ID NO: 1) and $PR_{15}$ (SEQ ID NO: 2) (3 μM) Measured by LDH Assay Cells were plated in culture medium in 2 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS023 was thawed to room temperature and diluted as in Example 1. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:
  Background (Culture medium only)
  Low control/"0% toxicity" (Cells only in culture medium)
  DMSO Control (Cells treated only with the amount of DMSO that GR- and PR-treated cells were exposed to)
  GR Only (Cells treated only with 3 μM $GR_{15}$) (SEQ ID NO: 1)
  Cells treated with 3 μM $GR_{15}$ (SEQ ID NO: 1) and one of the following doses of MS023: 60 μM, 30 μM, 10 μM, 3 μM, 1 μM.
  PR Only (Cells treated only with 3 μM $PR_{15}$) (SEQ ID NO: 2)
  Cells treated with 300 nM $PR_{15}$ (SEQ ID NO: 2) and one of the following doses of MS023: 60 μM, 30 μM, 10 μM, 3 μM, 1 μM.
  Cells treated with only one of the following doses of MS023: 60 μM, 30 μM, 10 μM, 3 μM, 1 μM.
  High control/"100% toxicity" (Cells lysed with lysis buffer)
  Positive control (5 μL LDH solution).

Plates were incubated for 24h at 37° C., 5% $CO_2$. Cells were tested and data were analyzed by LDH assay.

As shown in FIGS. 5A-5D, MS023 partially abrogated GR-induced toxicity at all tested doses. MS023 partially abrogated PR-induced cytotoxicity at doses of 10, 30, and 60 μM, and fully abrogated PR-induced toxicity at doses of 1 and 3 μM. Differences in abrogate ability of MS023 in GR-treated cells and PR-treated cells (as seen in Example 4) further suggest slightly different mechanisms of action of arginine-rich DRPs GR and PR.

Example 6: MS023 (0.01-3 μM) and Abrogation of Cytotoxicity Produced by $GR_{15}$ (SEQ ID NO: 1) and $PR_{15}$ (SEQ ID NO: 2) (3 μM) Measured by LDH Assay Cells were plated in culture medium in 2 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS023 was thawed to room temperature and diluted in warm culture medium to achieve final concentrations of 0.01, 0.03, 0.1, 0.3, 1, and 3 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:
  Background (Culture medium only)
  Low control/"0% toxicity" (Cells only in culture medium)
  DMSO Control (Cells treated only with the amount of DMSO that GR- and PR-treated cells were exposed to)
  GR Only (Cells treated only with 3 μM $GR_{15}$) (SEQ ID NO: 1)
  Cells treated with 3 μM $GR_{15}$ (SEQ ID NO: 1) and one of the following doses of MS023: 3 μM, 1 μM, 0.3 μM, 0.1 μM, 0.03 μM. 0.01 μM.
  PR Only (Cells treated only with 3 μM $PR_{15}$) (SEQ ID NO: 2)
  Cells treated with 3 μM $PR_{15}$ (SEQ ID NO: 2) and one of the following doses of MS023: 3 μM, 1 μM, 0.3 μM, 0.1 μM, 0.03 μM. 0.01 μM.
  Cells treated with only one of the following doses of MS023: 3 μM, 1 μM, 0.3 μM, 0.1 μM, 0.03 μM. 0.01 μM.
  High control/"100% toxicity" (Cells lysed with lysis buffer)
  Positive control (5 μL LDH solution).

Plates were incubated for 24h at 37° C., 5% $CO_2$. Cells were tested and data were analyzed using the procedure detailed in LDH assay kit instructions.

As shown in FIGS. 6A-6D, MS023 potently, and dose-dependently abrogated both GR and PR-induced toxicity. MS023 partially abrogated GR-induced toxicity at doses of 0.01, 0.03, 0.1, and 0.3 μM, and completely abrogated GR-induced toxicity at doses of 0.3, 1, and 3 μM. MS023 partially abrogated PR-induced toxicity at doses of 0.01, 0.03, and 0.1 μM, and completely abrogated PR-induced toxicity at doses of 0.03, 0.1, 0.3, 1, and 3 μM. Consistent with previous examples, MS023 more potently abrogated PR-induced toxicity.

Example 7: MS023 (1-60 μM) and Abrogation of Apoptotic Activity Induced by $GR_{15}$ (SEQ ID NO: 1) and PRs (SEQ ID NO: 2) (300 nM) Measured by Caspase-3 Assay Cells were plated in culture medium in 2 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS023 was thawed to room temperature and diluted as in Example 1. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 300 nM in wells.

The following conditions were plated in triplicate. Samples were surrounded by border wells on the outside of the plate filled with sterile Phosphate-buffered saline to prevent evaporation of volume in experimental wells during incubation:

Background (Culture medium only)
Untreated/"Cells Only" (Cells in culture medium)
DMSO Control (Cells treated only with the amount of DMSO that GR- and PR-treated cells were exposed to)
GR Only (Cells treated only with 300 nM $GR_{15}$) (SEQ ID NO: 1)
Cells treated with 3 μM $GR_{15}$ (SEQ ID NO: 1) and one of the following doses of MS023: 60 μM, 30 μM, 10 μM, 3 μM, 1 μM.
PR Only (Cells treated only with 300 nM $PR_{15}$) (SEQ ID NO: 2)
Cells treated with 300 nM $PR_{15}$ (SEQ ID NO: 2) and one of the following doses of MS023: 60 μM, 30 μM, 10 μM, 3 μM, 1 μM.
Cells treated with only one of the following doses of MS023: 60 μM, 30 μM, 10 μM, 3 μM, 1 μM.
Positive controls (Cells treated with either 5 or 16 μM PAC-1 Caspase-3 activator)
Plates were incubated for 24h at 37° C., 5% $CO_2$. Cells were tested and data were analyzed using the procedure detailed in Caspase-3 assay kit instructions.

As shown in FIGS. 7A-7D, MS023 abrogated GR and PR-induced apoptotic activity dose-dependently. 60, 30, and 10 μM doses of MS023 partially abrogated, and 3 and 1 μM doses of MS023 fully abrogated 300 nM GR-induced apoptotic activity. All doses of MS023 fully abrogated PR-induced apoptotic activity.

Example 8: MS023 (0.01-3 μM) and Abrogation of Apoptotic Activity Induced by $GR_{15}$ (SEQ ID NO: 1) and $PR_{15}$ (SEQ ID NO: 2) (3 μM) Measured by Caspase-3 Assay Cells were plated in culture medium in 2 96-well plates at a density of $3.7\times10^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS023 was thawed to room temperature and diluted in warm culture medium to achieve final concentrations of 3, 1, 0.3, 0.1, 0.03, and 0.01 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:
Background (Culture medium only)
Untreated/"Cells Only" (Cells in culture medium)
DMSO Control (Cells treated only with the amount of DMSO that GR- and PR-treated cells were exposed to)
GR Only (Cells treated only with 3 μM $GR_{15}$) (SEQ ID NO: 1)
Cells treated with 3 μM $GR_{15}$ (SEQ ID NO: 1) and one of the following doses of MS023: 3 μM, 1 μM, 0.3 μM, 0.1 μM, 0.03 μM, 0.01 μM.
PR Only (Cells treated only with 3 μM $PR_{15}$) (SEQ ID NO: 2)
Cells treated with 3 μM $PR_{15}$ (SEQ ID NO: 2) and one of the following doses of MS023: 3 μM, 1 μM, 0.3 μM, 0.1 μM, 0.03 μM, 0.01 μM.
Cells treated with only one of the following doses of MS023: 3 μM, 1 μM, 0.3 μM, 0.1 μM, 0.03 μM, 0.01 μM.
Positive controls (Cells treated with either 5 or 16 μM PAC-1 Caspase-3 activator)
Plates were incubated for 24h at 37° C., 5% $CO_2$. Cells were tested and data were analyzed using the procedure detailed in Caspase-3 assay kit instructions.

As shown in FIGS. 8A-8D, MS023 dose-dependently abrogated GR and PR-induced apoptotic activity. In both GR and PR-treated cells, all doses of MS023 partially abrogated GR and PR-induced apoptotic activity, and a 3 μM dose of MS023 fully abrogated GR and PR-induced apoptotic activity.

Example 9: MS023 (1-60 μM) and Abrogation of Proliferation Inhibition Induced by $GR_{15}$ (SEQ ID NO: 1) and PRs (SEQ ID NO: 2) (300 nM) Measured by BrdU ELISA Cells were plated in culture medium in 2 96-well plates at a density of $3.7\times10^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS023 was thawed to room temperature and diluted as in Example 1. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 300 nM in wells.

The following conditions were plated in triplicate. Samples were surrounded by border wells on the outside of the plate filled with sterile Phosphate-buffered saline to prevent evaporation of volume in experimental wells during incubation:
Culture medium only
Background (Cells only in culture medium, without BrdU reagent)
Untreated (Cells only in culture medium, with BrdU reagent)
DMSO Control (Cells treated only with the amount of DMSO that GR- and PR-treated cells were exposed to), and BrdU reagent
GR Only (Cells treated with 300 nM $GR_{15}$, (SEQ ID NO: 1) and BrdU reagent)
Cells treated with 300 nM $GR_{15}$, (SEQ ID NO: 1) BrdU reagent and one of the following doses of MS023: 60 μM, 30 μM, 10 μM, 3 μM, 1 μM.
PR Only (Cells treated with 300 nM $PR_{15}$, (SEQ ID NO: 2) and BrdU reagent)
Cells treated with 300 nM $PR_{15}$, (SEQ ID NO: 2) BrdU reagent and one of the following doses of MS023: 60 μM, 30 μM, 10 μM, 3 μM, 1 μM.
Cells treated with BrdU reagent and one of the following doses of MS023: 60 μM, 30 μM, 10 μM, 3 μM, 1 μM.
Plates were incubated for 24h at 37° C., 5% $CO_2$. Cells were tested and data were analyzed using the procedure detailed in BrdU ELISA kit instructions.

As shown in FIGS. 9A-9D, MS023 abrogated GR and PR-induced proliferation inhibition, without inducing excessive proliferation, at all doses tested. All doses of MS023 partially abrogated GR-induced proliferation inhibition, with a dose of 3 μM MS023 fully rescuing GR-induced proliferation inhibition. All doses of MS023 fully abrogated PR-induced proliferation inhibition.

Example 10: Comparison of DRP-Induced Dysmetabolism Phenotypes in Neuronal and Non-Neuronal Cell Types Measured by WST-1 Assay Using Chinese Hamster Ovary (CHO) and Mouse Neuroblastoma-Spinal Cord Hybrid (NSC-34) Cells and Both Arginine-Rich: $GR_{15}$, (SEQ ID NO: 1) $PR_{15}$, (SEQ ID NO: 2) and Non-Arginine-Rich: $GP_{15}$, (SEQ ID NO: 3) $PA_{15}$, (SEQ ID NO: 4) DRPs (at 30 and 3 µM Doses)

Cells were plated in 200 µL of culture medium in 2 96-well plates. In plate 1, CHO cells were plated at a density of $1 \times 10^4$ cells/well, and in plate 2, NSC-34 cells were plated at a density of $2.5 \times 10^4$ cells per well, and incubated overnight at 37° C., 5% $CO_2$. Different densities were used for the two cell types because CHO cells had been established to grow 2.5 times faster than NSC-34 cells in previous assays. The following day, 10 mM stocks of $GR_{15}$, (SEQ ID NO: 1) $PR_{15}$, (SEQ ID NO: 2) $GP_{15}$, (SEQ ID NO: 3) and $PA_{15}$ (SEQ ID NO: 4) were equilibrated to room temperature and diluted in warm culture medium to achieve two concentrations of each protein: 600 µM (would be 30 µM in plate), and 60 µM (would be 3 µM in plate).

The following conditions were plated in triplicate. Samples were surrounded by border wells on the outside of the plate filled with sterile Phosphate-buffered saline to prevent evaporation of volume in experimental wells during incubation:
 Untreated (Cells only in culture medium)
 DMSO Controls (Cells treated only with the amount of DMSO that DRP-treated cells were exposed to)
  i. DMSO Control 1: 0.3% DMSO corresponding to 30 µM DRP dose
  ii. DMSO Control 2: 0.03% DMSO corresponding to 3 µM DRP dose
 Cells treated with 30 or 3 µM $GR_{15}$ (SEQ ID NO: 1)
 Cells treated with 30 or 3 µM $PR_{15}$ (SEQ ID NO: 2)
 Cells treated with 30 or 3 µM $PA_{15}$ (SEQ ID NO: 4)
 Cells treated with 30 or 3 µM GPIs (SEQ ID NO: 3)

Plates were incubated for 48h at 37° C., 5% $CO_2$. Immediately before testing, culture medium was removed and replaced with 200 µL PBS-Glucose solution (4.5 g/L, sterile) that had been warmed from 4° C. in a 37° C. water bath for 10 minutes before use. WST-1 reagent aliquots were thawed from −20° C. and equilibrated to room temperature before use. 20 µL WST-1 reagent was added per well containing 200 µL PBS-Glucose. Plates were incubated with WST-1 at 37° C., 5% $CO_2$ for 1 hour, with absorbance readings (450 nm) taken on a Molecular Devices Plate Reader (SpectraMax M3) every 15 minutes. Data was exported from plate reader's SoftMax Pro 7.0 software into an excel file.

As shown in FIGS. 10A-10D, DRP challenge resulted in impaired metabolic function in both non-neuronal CHO and motor-neuron-like NSC-34 cells. However, significantly greater reduction of metabolic activity in NSC-34 was observed when compared to CHO. These observations were exclusively observed in cells treated with arginine-rich DRPs $GR_{15}$ (SEQ ID NO: 1) and $PR_{is}$, (SEQ ID NO: 2) suggesting that motor-neuron-like NSC-34 are not only more sensitive to DRP challenge, but are specifically more sensitive to arginine-rich DRP challenge.

Example 11: Dose-Response Patterns of DRP-Induced Toxicity in NSC-34 Cells Determined by LDH Assay Cells were plated in culture medium in 2 96-well plates at a density of $5 \times 10^4$ cells per well, and incubated overnight at 37° C., 5% $CO_2$. The following day, 10 mM stocks of $GR_{15}$, (SEQ ID NO: 1) $PR_{15}$, (SEQ ID NO: 2) $GP_{15}$, (SEQ ID NO: 3) and $PA_{15}$ (SEQ ID NO: 4) were equilibrated to room temperature and diluted in warm culture medium to achieve the following concentrations of DRPs (at 10× concentration what would be achieved in plate): 30, 10, 3, 1, 0.3, 0.1 µM. 10 µL of each concentration would be added to 100 µL base media in plate to achieve final concentrations of 3, 1, 0.3, 0.1, 0.03, and 0.01 µM DRP.

The following conditions were plated in duplicate. Samples were surrounded by border wells on the outside of the plate filled with sterile Phosphate-buffered saline to prevent evaporation of volume in experimental wells during incubation:
 Background (Culture medium only)
 Low control/"0% toxicity" (Cells only in culture medium)
 DMSO Controls (Cells treated only with the amount of DMSO that DRP-treated cells were exposed to at each concentration)
  i. The DMSO controls tested were as follows, corresponding to DRP doses starting at the highest (3 µM to the lowest 0.01 µM), and were diluted in culture medium:
   1. 0.03% DMSO
   2. 0.01% DMSO
   3. 0.003% DMSO
   4. 0.001% DMSO
   5. 0.0003% DMSO
   6. 0.0001% DMSO
 Cells treated with $GR_{15}$ (SEQ ID NO: 1) at one of the following doses: 3 µM, 1 µM, 0.3 µM, 0.1 µM, 0.03 µM, 0.01 µM.
 Cells treated with $PR_{15}$ (SEQ ID NO: 2) at one of the following doses: 3 µM, 1 µM, 0.3 µM, 0.1 µM, 0.03 µM, 0.01 µM.
 Cells treated with $GP_{15}$ (SEQ ID NO: 3) at one of the following doses: 3 µM, 1 µM, 0.3 µM, 0.1 µM, 0.03 µM, 0.01 µM.
 Cells treated with $PA_{15}$ (SEQ ID NO: 4) at one of the following doses: 3 µM, 1 µM, 0.3 µM, 0.1 µM, 0.03 µM, 0.01 µM.
 High control/"100% toxicity" (Cells lysed with lysis buffer)
 Positive control (5 µL LDH solution).

Plates were incubated for 24h at 37° C., 5% $CO_2$. Cells were tested and data were analyzed using the procedure detailed in LDH assay kit instructions.

Figure 11:
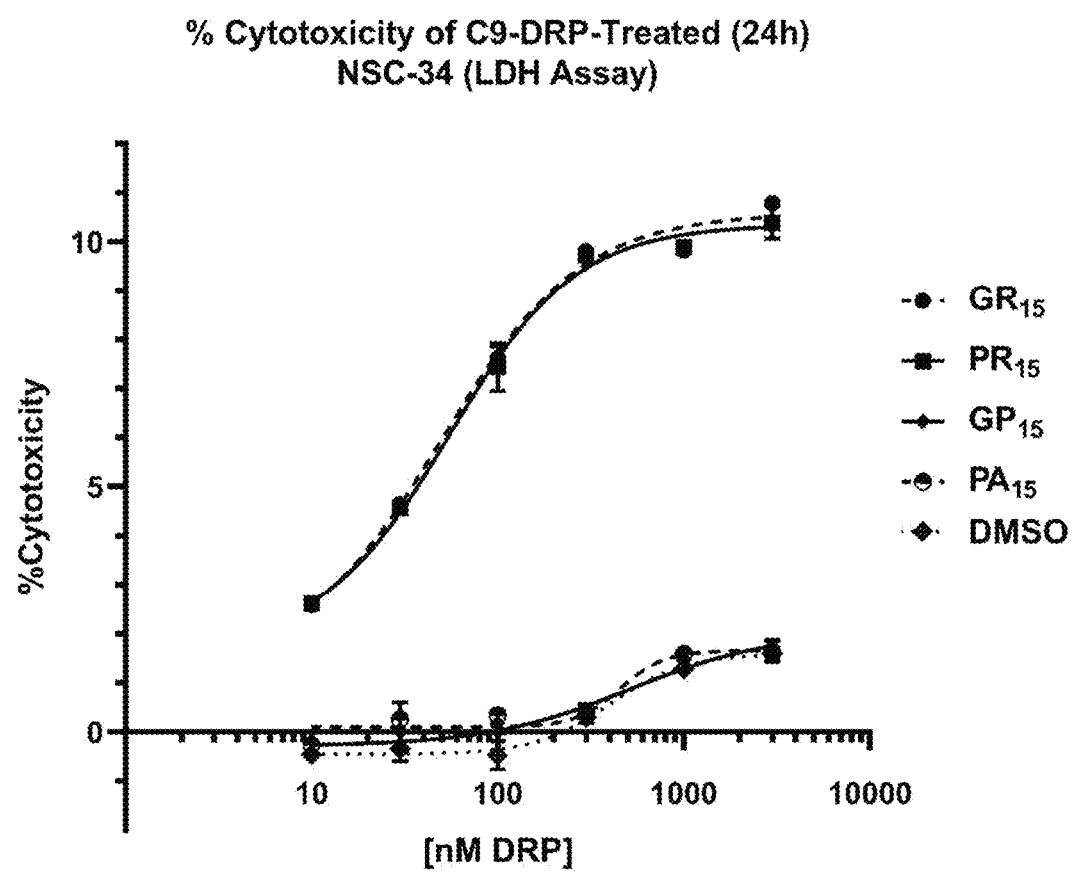
FIG. 11 is a graph showing the dose-response patterns of DRP-induced toxicity in NSC-34 cells determined by LDH assay.

As shown in FIG. 11, arginine-rich DRP ($GR_{15}$, (SEQ ID NO: 1) $PR_{15}$) (SEQ ID NO: 2) treatment produced significant, dose-dependent toxicity in NSC-34 cells when incubated for 24 hours, while non-arginine-rich DRP ($GP_{15}$, (SEQ ID NO: 3) $PA_{15}$) (SEQ ID NO: 4) treatment did not. $GR_{15}$ (SEQ ID NO: 1) and $PR_{15}$ (SEQ ID NO: 2) toxicity of approximately 10% was achieved using concentrations as low as 300 nM. $GR_{15}$ (SEQ ID NO: 1) and $PR_{15}$ (SEQ ID NO: 2) exhibited nearly identical dose-response profiles, with $GR_{15}$ (SEQ ID NO: 1) and $PR_{15}$ (SEQ ID NO: 2) yielding EC50's of 50 t 26 nM, and 56 t 20 nM, respectively.

Example 12: Dose-Response Patterns of DRP-Induced Apoptotic Activity in NSC-34 Cells Determined by Caspase-3 Assay Cells were plated in culture medium in 2 96-well plates at a density of $5 \times 10^4$ cells per well, and incubated overnight at 37° C., 5% $CO_2$. The following day, 10 mM stocks of $GR_{15}$, (SEQ ID NO: 1) $PR_{15}$, (SEQ ID NO: 2) $GP_{15}$, (SEQ ID NO: 3) and $PA_1$s (SEQ ID NO: 4) were equilibrated to room temperature and diluted in warm culture medium to achieve the following concentrations of DRPs (at 10× concentration what would be achieved in plate): 30, 10, 3, 1, 0.3, 0.1 µM. 10 µL of each concentration would be added to 100 µL base media in plate to achieve final concentrations of 3, 1, 0.3, 0.1, 0.03, and 0.01 µM DRP.

The following conditions were plated in triplicate. Samples were surrounded by border wells on the outside of the plate filled with sterile Phosphate-buffered saline to prevent evaporation of volume in experimental wells during incubation:

Background (Culture medium only)
Untreated/"Cells Only" (Cells in culture medium)
DMSO Controls (Cells treated only with the amount of DMSO that DRP-treated cells were exposed to at each concentration)
  i. The DMSO controls tested were as follows, corresponding to DRP doses starting at the highest (3 µM to the lowest 0.01 µM), and were diluted in culture medium:
    1. 0.03% DMSO
    2. 0.01% DMSO
    3. 0.003% DMSO
    4. 0.001% DMSO
    5. 0.0003% DMSO
    6. 0.0001% DMSO
Cells treated with $GR_{15}$ (SEQ ID NO: 1) at one of the following doses: 3 µM, 1 µM, 0.3 µM, 0.1 µM, 0.03 µM, 0.01 µM.
Cells treated with $PR_{15}$ (SEQ ID NO: 2) at one of the following doses: 3 µM, 1 µM, 0.3 µM, 0.1 µM, 0.03 µM, 0.01 µM.
Cells treated with $GP_{15}$ (SEQ ID NO: 3) at one of the following doses: 3 µM, 1 µM, 0.3 µM, 0.1 µM, 0.03 µM, 0.01 µM.
Cells treated with $PA_{15}$ (SEQ ID NO: 4) at one of the following doses: 3 µM, 1 µM, 0.3 µM, 0.1 µM, 0.03 µM, 0.01 µM.
Positive controls (Cells treated with either 5 or 16 µM PAC-1 Caspase-3 activator)

Plates were incubated for 24h at 37° C., 5% $CO_2$. Cells were tested and data were analyzed using the procedure detailed in Caspase-3 assay kit instructions.

Figure 12:
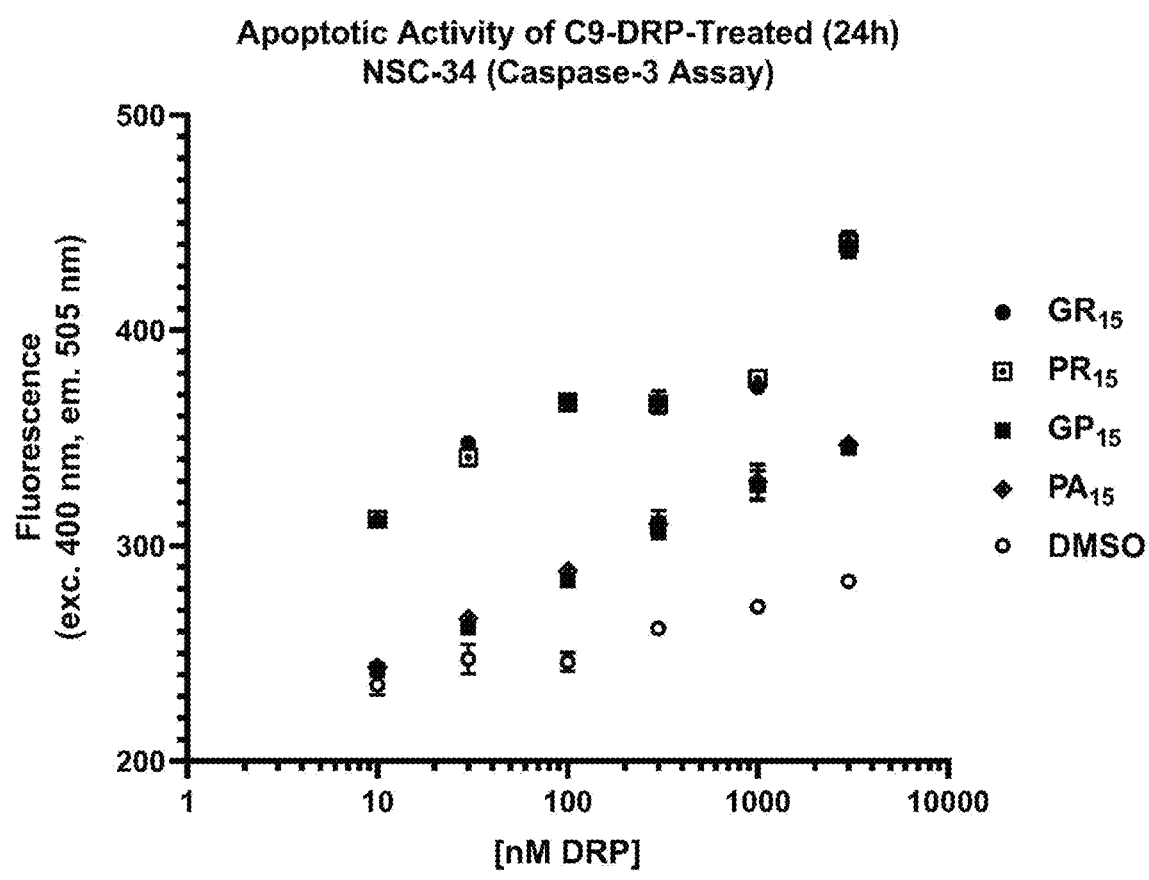
FIG. 12 is a graph showing the dose-response patterns of DRP-induced apoptotic activity in NSC-34 cells determined by Caspase-3 assay.

As shown in FIG. 12, all DRPs induced apoptotic activity in NSC-34 cells in a dose-dependent manner. Arginine-rich DRPs $GR_{15}$ (SEQ ID NO: 1) and $PR_{15}$ (SEQ ID NO: 2) clustered together, producing the most significant amount of apoptotic activity. Non-arginine-rich GPIs (SEQ ID NO: 3) and $PA_{15}$ (SEQ ID NO: 4) also clustered together, producing less robust levels of apoptotic activity when compared to DMSO-treated controls.

Example 13: Dose-Response Patterns of DRP-Induced Proliferation Inhibition in NSC-34 Cells Determined by BrdU ELISA Cells were plated in culture medium in 2 96-well plates at a density of $5 \times 10^4$ cells per well, and incubated overnight at 37° C., 5% $CO_2$. The following day, 10 mM stocks of $GR_{15}$, (SEQ ID NO: 1) $PR_{15}$, (SEQ ID NO: 2) $GP_{15}$, (SEQ ID NO: 3) and $PA_{15}$ (SEQ ID NO: 4) were equilibrated to room temperature and diluted in warm culture medium to achieve the following concentrations of DRPs (at 10× concentration what would be achieved in plate): 30, 10, 3, 1, 0.3, 0.1 µM. 10 µL of each concentration would be added to 100 µL base media in plate to achieve final concentrations of 3, 1, 0.3, 0.1, 0.03, and 0.01 µM DRP.

The following conditions were plated in triplicate. Samples were surrounded by border wells on the outside of the plate filled with sterile Phosphate-buffered saline to prevent evaporation of volume in experimental wells during incubation:

Culture medium only
Background (Cells only in culture medium, without BrdU reagent)
Untreated (Cells only in culture medium, with BrdU reagent)
DMSO Controls (Cells treated with BrdU reagent and the amount of DMSO that DRP-treated cells were exposed to at each concentration)
  i. The DMSO controls tested were as follows, corresponding to DRP doses starting at the highest (3 µM to the lowest 0.01 µM), and were diluted in culture medium:
    1. 0.03% DMSO
    2. 0.01% DMSO
    3. 0.003% DMSO
    4. 0.001% DMSO
    5. 0.0003% DMSO
    6. 0.0001% DMSO
Cells treated with BrdU reagent and $GR_{15}$ (SEQ ID NO: 1) at one of the following doses: 3 µM, 1 µM, 0.3 µM, 0.1 µM, 0.03 µM, 0.01 µM.
Cells treated with BrdU reagent and $PR_{15}$ (SEQ ID NO: 2) at one of the following doses: 3 µM, 1 µM, 0.3 µM, 0.1 µM, 0.03 µM, 0.01 µM.
Cells treated with BrdU reagent and $GP_{15}$ (SEQ ID NO: 3) at one of the following doses: 3 µM, 1 µM, 0.3 µM, 0.1 µM, 0.03 µM, 0.01 µM.
Cells treated with BrdU reagent and $PA_{15}$ (SEQ ID NO: 4) at one of the following doses: 3 µM, 1 µM, 0.3 µM, 0.1 µM, 0.03 µM, 0.01 µM.

Plates were incubated for 24h at 37° C., 5% $CO_2$. Cells were tested and data were analyzed using the procedure detailed in BrdU ELISA kit instructions.

Figure 13:
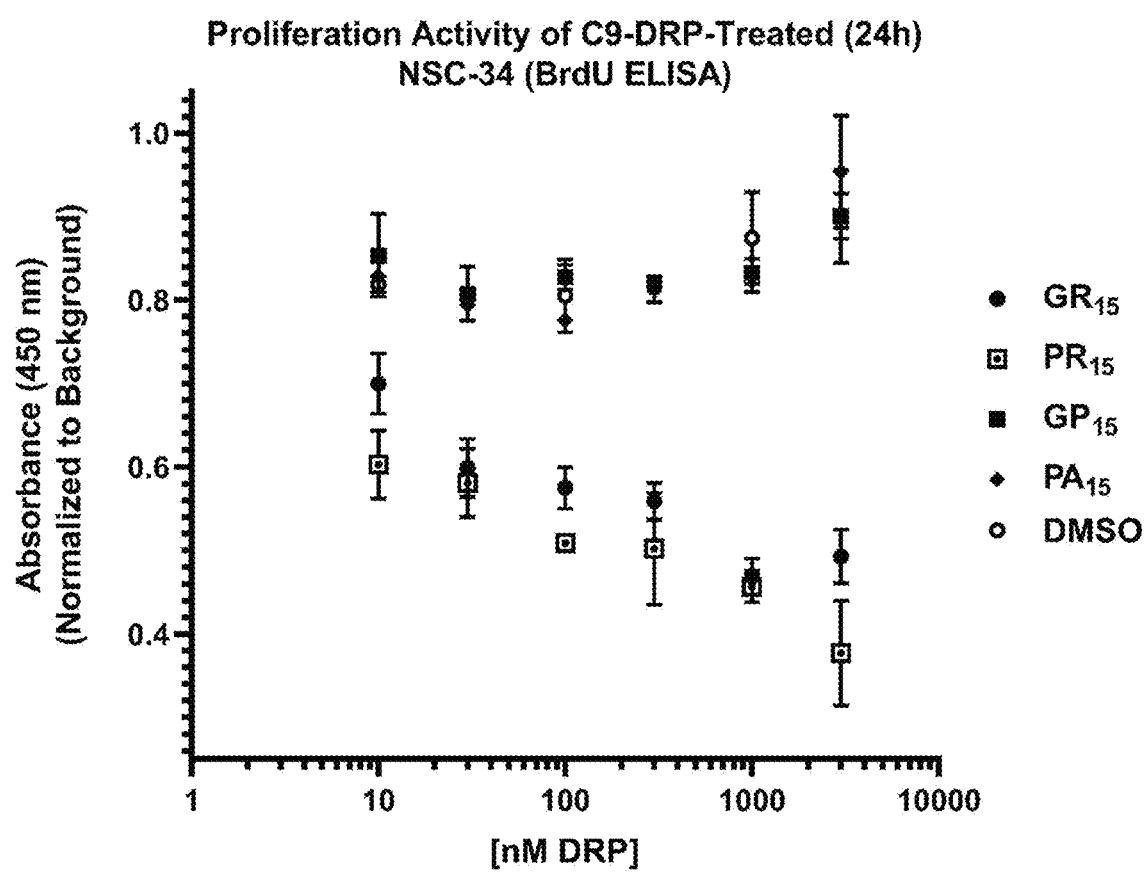
FIG. 13 is a graph showing the dose-response patterns of DRP-induced proliferation inhibition in NSC-34 cells determined by BrdU ELISA.

As shown in FIG. 13, non-arginine-rich DRPs GPIs (SEQ ID NO: 3) and $PA_{15}$ (SEQ ID NO: 4) did not significantly impact proliferation activity compared to DMSO-treated controls. Arginine-rich DRPs $GR_{15}$ (SEQ ID NO: 1) and $PR_{15}$ (SEQ ID NO: 2) both significantly suppressed proliferative activity in a dose-dependent manner, with $PR_{15}$ (SEQ ID NO: 2) being the strongest inhibitor.

Example 14: MS023 Decreases Asymmetrical Arginine Methylation of NSC-34 Cells On Day 0, NSC-34 Cells were plated in 48 wells of a 96 well plate, and CHO cells were plated in the other 48 wells of the same 96-well plate. NSC-34 cells were plated in DMEM/High glucose media. CHO cells were plated in Ham's F-12K (Kaighn's) Medium. Both cell lines were incubated overnight to reach approximately 50% confluency.

On Day 1, 24 wells of the NSC-34 cells and 24 wells of the CHO cells were treated with the following concentrations of MS023: 1 μM, 3 μM, 6 μM, 10 μM, 30 μM, and 60 μM. The cells were then incubated overnight.

On Day 2, 18 wells of the untreated NSC-34 cells and 18 wells of the untreated CHO cells were treated with the same concentrations of MS023 as those on Day 1. This left 6 wells of each cell line that never received MS023. Once MS023 was added, the cells were incubated overnight.

On Day 3, all media in the 96-well plate was removed and the cells were fixed with 3.7% Paraformaldehyde (PFA). Cells were then washed and permeabilized with 1×PBS/0.1% Triton X-100.

After removing the PBS/Triton wash, Odyssey Blocking Buffer (LI-COR, 927-40100) was applied to all wells and the plate sat at room temperature with moderate shaking for 90 minutes. After 90 minutes, the blocking buffer was removed and the cells were treated with a 1:500 dilution of the Anti-Asymmetric Di-Methyl Arginine Motif primary antibody (Cell Signaling Technology, #13522). Incubation with the primary antibody continued overnight at 4 degrees Celsius with no shaking.

On Day 4, the primary antibody solution was removed from the plate, and the cells were washed with 1×PBS/0.1% Tween 20. After washing, cells were given a secondary antibody mixture containing a 1:1000 dilution of IRDye 800 CW Anti-Rabbit antibody (LI-COR, 926-32211) and a 1:500 dilution of Cell Tag 700 Stain (LI-COR, 926-41090). The secondary antibody mixture remained on cells for 60 minutes with gentle shaking and protected from light.

After 60 minutes, the secondary antibody mixture was removed and the cells were again washed with 1×PBS/0.1% Tween 20. All wash buffer was then removed, and the plate was gently patted dry to remove excess solution. The plate was then read on the LI-COR Odyssey Classic Imaging System which provides results based on fluorescence. In this experiment, fluorescence occurred as a result of cellular, asymmetric arginine methylation. MS023 was given to cells for either 24 or 48 hours, with expectation for it to reduce cellular, asymmetric arginine methylation. Cell number per well was accounted for using the Cell Tag 700 Stain, which fluorescently labels total protein levels in a cell. To this effect, fluorescence from asymmetrical arginine methylation per well (800) was divided by fluorescence from the total protein level per well (700) to produce an outcome of 800/700.

Figure 14:
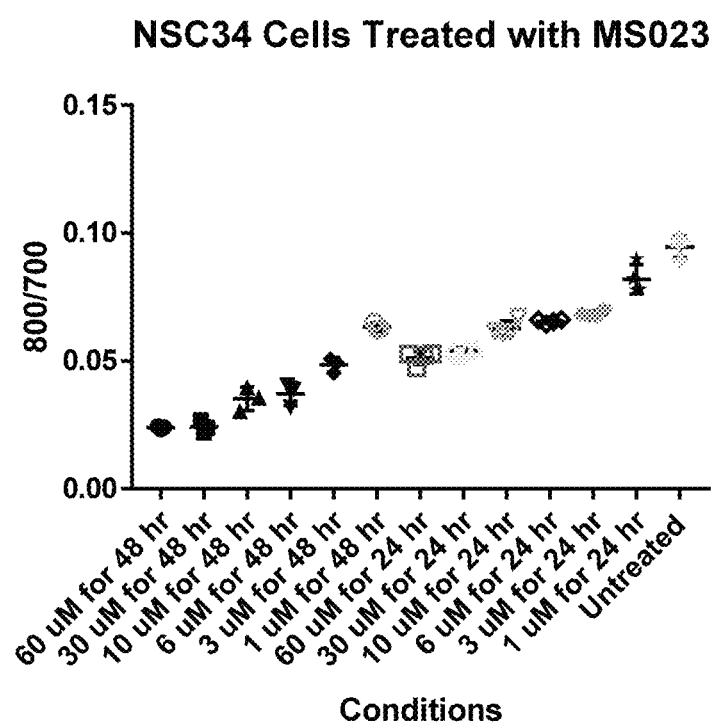
FIG. 14 is a graph showing MS023 decreases asymmetrical arginine methylation of NSC-34 cells.

As shown in FIG. 14, when compared to untreated cells, all conditions were significantly decreased in their 800/700 readout. With 24 hour treatment, MS023 decreased asymmetrical arginine methylation of NSC-34 cells by approximately 13% at 1 μM and 45% at 60 μM. With 48 hour treatment, MS023 decreased asymmetrical arginine methylation of NSC-34 cells by approximately, 33% at 1 μM and 75% at 60 PM.

Example 15: In-Vitro Arginine Methylation of Synthetic GR$_{15}$, (SEQ ID NO: 1)

To assess interaction between PRMT1 and GR$_{15}$, (SEQ ID NO: 1) an in-vitro methylation assay system was developed. This system consists of a mixture of recombinant PRMT1 enzyme, S-(5'-Adenosyl)-L-methionine iodide, (SAM) as a methyl donor, and potential substrate of PRMT1 activity. For this experiment, 11 tubes were prepared, each containing various amount of the following components:
Recombinant PRMT1 protein (Active Motif, Cat. 31411)
S-(5'-Adenosyl)-L-methionine iodide, (SAM) (Sigma-Aldrich Cat. A4377)
GR$_{15}$ (SEQ ID NO: 1)
PR$_{15}$ (SEQ ID NO: 2)
SOD1 from human erythrocytes (S9636-1KU)
These constituents were mixed in a 0.5 ml flat-capped tubes (Thermo Fisher Scientific, AB0350) according to Table 4 (all values are in microliters (μl)).

TABLE 4

| Tube | PRMT 1 | SAM | H4 | GR | PR | SOD1 | 10X PBS | H2O | Total |
|---|---|---|---|---|---|---|---|---|---|
| 1 |  | 2 | 2 |  |  |  | 3 | 23 | 30 |
| 2 | 1 | 2 | 2 |  |  |  | 3 | 22 | 30 |
| 3 | 2 | 2 | 2 |  |  |  | 3 | 21 | 30 |
| 4 | 3 | 2 | 2 |  |  |  | 3 | 20 | 30 |
| 5 | 4 | 2 | 2 |  |  |  | 3 | 19 | 30 |
| 6 | 5 | 2 | 2 |  |  |  | 3 | 18 | 30 |
| 7 | 6 | 2 | 2 |  |  |  | 3 | 17 | 30 |
| 8 |  |  | 2 |  |  |  | 3 | 25 | 30 |
| 9 | 2 | 2 | 4 |  |  |  | 3 | 19 | 30 |
| 10 | 2 | 2 |  | 2 |  |  | 3 | 21 | 30 |
| 11 | 2 | 2 |  |  | 20 |  | 3 | 3 | 30 |

Once all tubes were prepared, each tube was gently tapped to ensure mixture, and the tubes were placed in an incubator at 37 degrees Celsius for 2 hours. After 2 hours, the reaction mixture was stopped with the addition of 10 μl of NuPage LDS Sample Buffer (Thermo Fisher Scientific, NP0007). The tubes were gently tapped to ensure mixture, and then boiled for 5 minutes in a 95 degrees Celsius water bath. Samples were then run in a 4-12% Bis-Tris Gel (Thermo Fisher Scientific, NP0322BOX) for SDS-PAGE.

The gel was then transferred using the iBlot apparatus and an iBlot 2 Nitrocellulose Mini Stack (Thermo Fisher Scientific, IB23002). After transfer, the membrane was placed in Superblock Blocking Buffer (Thermo Fisher Scientific, 37515) and blocked overnight at 4 degrees Celsius. The following day, the blocking buffer was removed, and a primary antibody solution of anti-Histone 4 H4R3me2a at 1:500 (Active Motif, Cat. 39006) and Anti-C9ORF72/C9RANT (poly-GR) Antibody at 1:1000 (Millipore, mABN778) in Superblock/0.2% Tween 20 was applied to the membrane for 60 minutes at room temperature with gentle shaking. Primary antibody solution was removed, and the membrane was washed with 1×PBS/0.1% Tween 20. A secondary antibody solution containing a 1:10,000 dilution of IRDye 800 CW Anti-Rabbit antibody and a 1:10,000 dilution of IRDye 680 RD Anti-Rat antibody (LI-COR, 925-68076) in Superblock/0.2% Tween 20 was applied to the membrane for 60 minutes at room temperature with gentle shaking. The secondary antibody was removed, and the membrane was washed with 1×PBS/0.1% Tween 20. Following wash steps, the membrane was read on the LI-COR Odyssey Classic Imaging System.

Figure 15A:
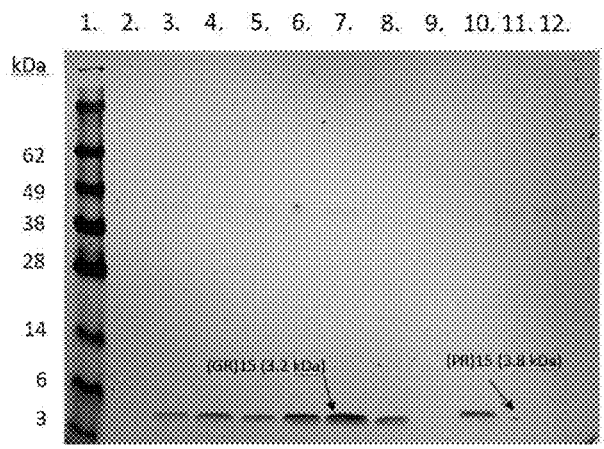
FIGS. 15A and 15B present quantitative image analysis of in-vitro arginine methylation of synthetic $GR_{15}$. (SEQ ID NO: 1)
Figure 15B:
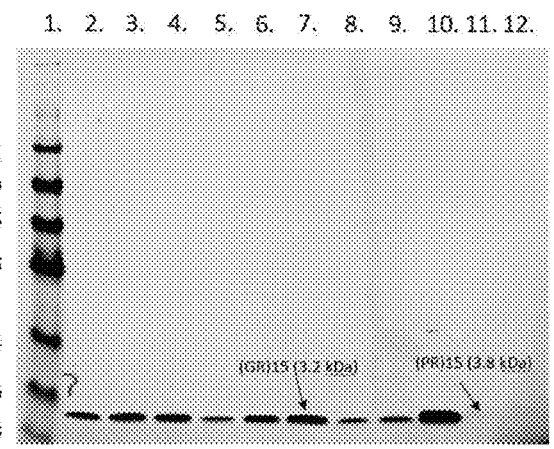
Figure 16A:
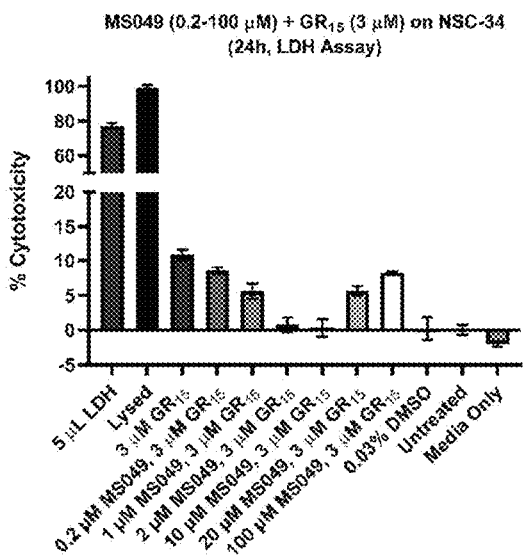
FIGS. 16A-16D are graphs comparing the activity of MS049 (0.2-100 μM) to abrogate cytoxicity produced by $GR_{15}$ (SEQ ID NO: 1) (3 μM) (FIGS. 16A and 16B) and $PR_{15}$ (SEQ ID NO: 2) (3 μM) (FIGS. 16C and 16D) measured by LDH assay.
Figure 16B:
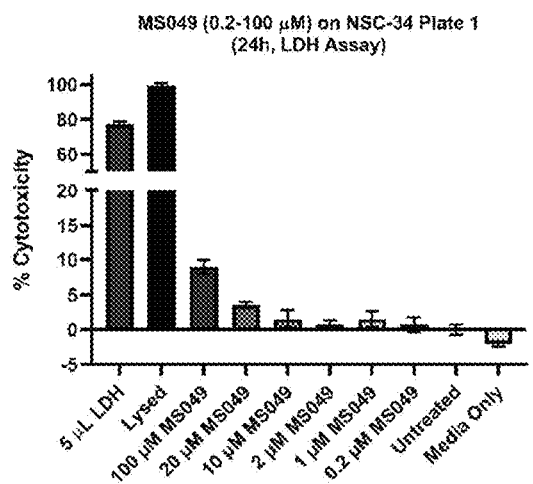
Figure 16C:
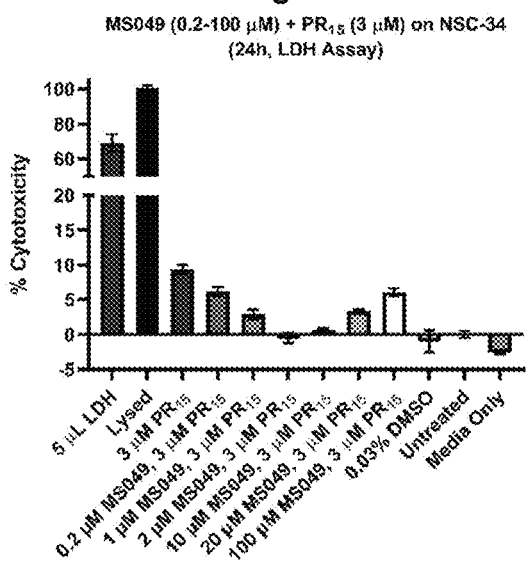
Figure 16D:
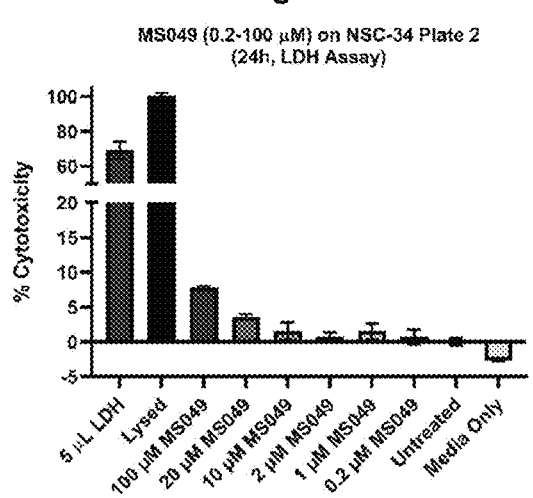

As shown in FIGS. 15A and 15B, GR$_{15}$ (SEQ ID NO: 1) is asymmetrically methylated by PRMT1, and is detected by the Histone 4 anti-H4R3me2a antibody. This antibody was raised against the region of the Histone 4 protein that contains a Glycine-Arginine pair. When either PRMT1 or the methyl donor SAM is removed from the reaction mixture, asymmetrical methylation of GR$_{15}$ (SEQ ID NO: 1)does not proceed (FIG. 15A lanes 2 and 9). FIG. 15B demonstrates that GR$_{15}$ (SEQ ID NO: 1)was present in every well and therefore its methylation is dependent on its interaction with PRMT1.

Example 16: MS049 (0.2-100 μM) and Abrogation of Cytotoxicity Produced by GR$_{15}$ (SEQ ID NO: 1) and PR$_{15}$ (SEQ ID NO: 2) (3 μM) Measured by LDH Assay Cells were plated in culture medium in 2 96-well plates at a density of 3.7×10$^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS049 was thawed to room temperature and diluted in warm culture medium to achieve final concentrations of 0.2, 1, 2, 10, 20, and 100 µM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Background (Culture medium only)
Low control/"0% toxicity" (Cells only in culture medium)
DMSO Control (Cells treated only with the amount of DMSO that GR- and PR-treated cells were exposed to)
GR Only (Cells treated only with 3 µM $GR_{15}$) (SEQ ID NO: 1)
Cells treated with 3 µM $GR_{15}$ (SEQ ID NO: 1) and one of the following doses of MS049: 100 µM, 20 µM, 10 µM, 2 µM, 1 µM. 0.2 PM.
PR Only (Cells treated only with 3 µM $PR_{15}$) (SEQ ID NO: 2)
Cells treated with 3 µM $PR_{15}$ (SEQ ID NO: 2) and one of the following doses of MS049: 100 µM, 20 µM, 10 µM, 2 µM, 1 µM. 0.2 µM.
Cells treated with only one of the following doses of MS049: 100 µM, 20 µM, 10 µM, 2 µM, 1 µM. 0.2 µM.
High control/"100% toxicity" (Cells lysed with lysis buffer)
Positive control (5 µL LDH solution).

Plates were incubated for 24h at 37° C., 5% $CO_2$. Cells were tested and data were analyzed using the procedure detailed in LDH assay kit instructions.

As shown in FIGS. 16A-16D, MS049 dose-dependently abrogated both GR and PR-induced toxicity. MS049 partially abrogated GR and PR-induced toxicity at doses of 0.2, 1, 2, 20 and 100 µM, and completely abrogated GR and PR-induced toxicity at doses of 2 and 10 µM. MS049 did cause significant toxicity independently of GR and PR treatment at doses of 100 and 20 µM, but not at other doses tested.

Example 17: MS049 Decreases Asymmetrical Arginine Methylation of NSC-34 Cells

On Day 0, NSC-34 Cells were plated in 48 wells of a 96 well plate, and CHO cells were plated in the other 48 wells of the same 96-well plate. NSC-34 cells were plated in DMEM/High glucose media. CHO cells were plated in Ham's F-12K (Kaighn's) Medium. Both cell lines were incubated overnight to reach approximately 50% confluency.

On Day 1, 24 wells of the NSC-34 cells and 24 wells of the CHO cells were treated with the following concentrations of MS049: 0.2 µM, 1 µM, 2 µM, 10 µM, 20 µM, and 100 µM. The cells were then incubated overnight.

On Day 2, 18 wells of the untreated NSC-34 cells and 18 wells of the untreated CHO cells were treated with the same concentrations of MS049 as those on Day 1. This left 6 wells of each cell line that never received MS049. Once MS049 was added, the cells were incubated overnight.

On Day 3, all media in the 96-well plate was removed and the cells were fixed with 3.7% Paraformaldehyde (PFA). Cells were then washed and permeabilized with 1×PBS/0.1% Triton X-100.

After removing the PBS/Triton wash, Odyssey Blocking Buffer (LI-COR, 927-40100) was applied to all wells and the plate sat at room temperature with moderate shaking for 90 minutes. After 90 minutes, the blocking buffer was removed and the cells were treated with a 1:500 dilution of the Anti-Asymmetric Di-Methyl Arginine Motif primary antibody (Cell Signaling Technology, #13522). Incubation with the primary antibody continued overnight at 4 degrees Celsius with no shaking.

On Day 4, the primary antibody solution was removed from the plate, and the cells were washed with 1×PBS/0.1% Tween 20. After washing, cells were given a secondary antibody mixture containing a 1:1000 dilution of IRDye 800 CW Anti-Rabbit antibody (LI-COR, 926-32211) and a 1:500 dilution of Cell Tag 700 Stain (LI-COR, 926-41090). The secondary antibody mixture remained on cells for 60 minutes with gentle shaking and protected from light.

After 60 minutes, the secondary antibody mixture was removed and the cells were again washed with 1×PBS/0.1% Tween 20. All wash buffer was then removed, and the plate was gently patted dry to remove excess solution. The plate was then read on the LI-COR Odyssey Classic Imaging System which provides results based on fluorescence. In this experiment, fluorescence occurred as a result of cellular, asymmetric arginine methylation. MS049 was given to cells for either 24 or 48 hours, with expectation for it to reduce cellular, asymmetric arginine methylation. Cell number per well was accounted for using the Cell Tag 700 Stain, which fluorescently labels total protein levels in a cell. To this effect, fluorescence from asymmetrical arginine methylation per well (800) was divided by fluorescence from the total protein level per well (700) to produce an outcome of 800/700.

Figure 17:
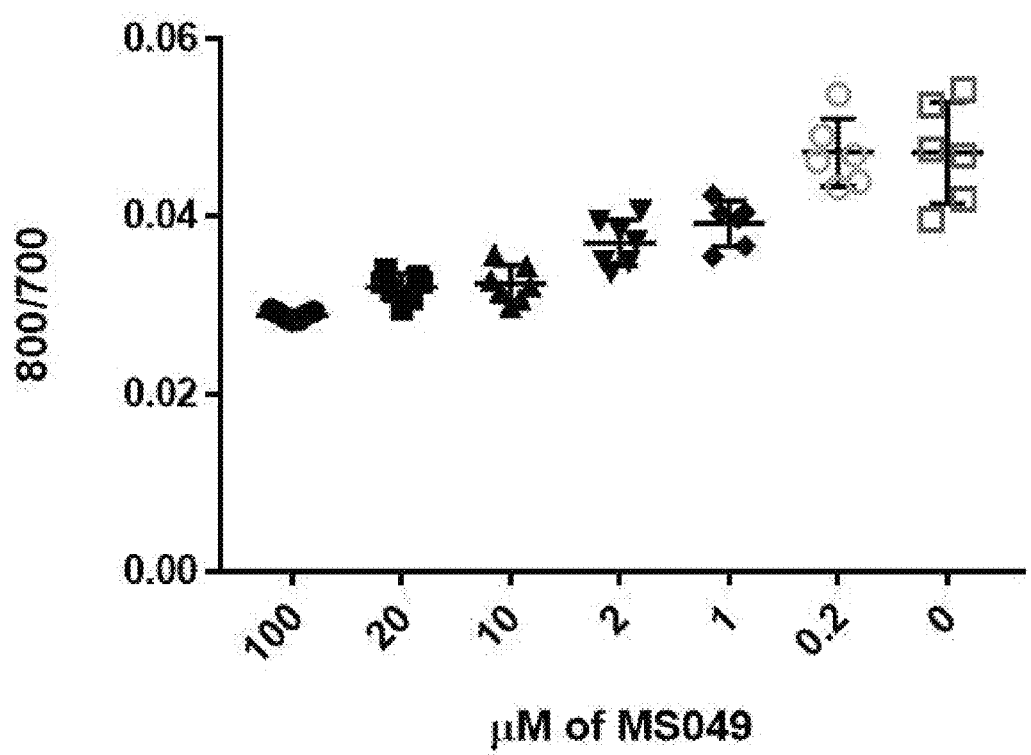
FIG. 17 is a graph showing MS049 decreases asymmetrical arginine methylation of NSC-34 cells.
Figure 18A:
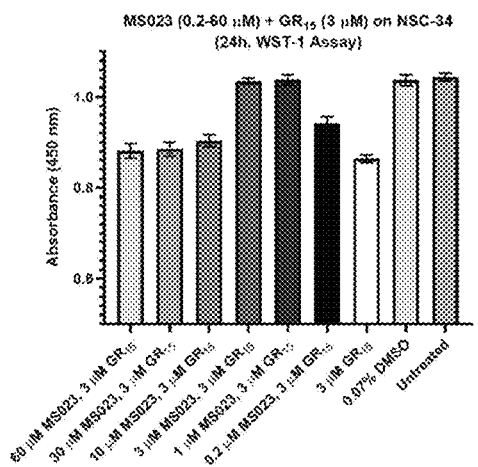
FIGS. 18A-18F are graphs comparing the activity of MS023 (0.2-60 μM) to abrogate dysmetabolism produced by $GR_{15}$ (SEQ ID NO: 1) (3 μM) (FIGS. 18A and 18B) and $PR_{15}$ (SEQ ID NO: 2) (3 μM) (FIGS. 18C and 18D) measured by WST-1 assay with negative control MS094 (0.2-60 μM) (FIGS. 18E and 18F).
Figure 18B:
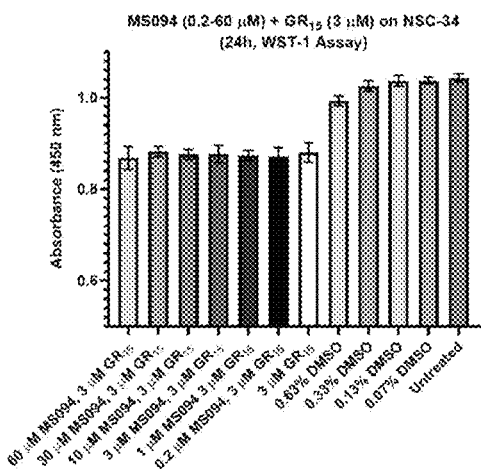
Figure 18C:
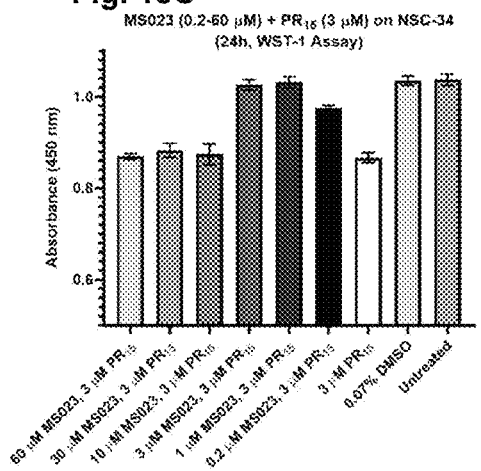
Figure 18D:
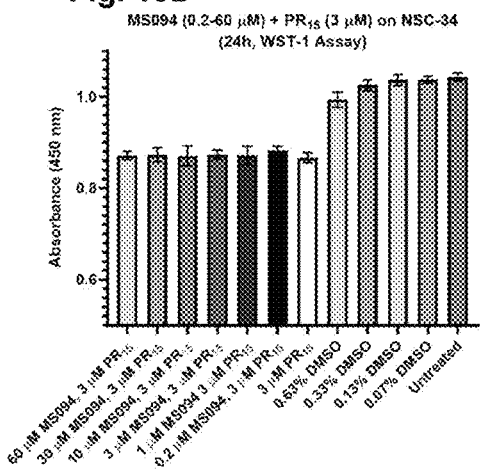
Figure 18E:
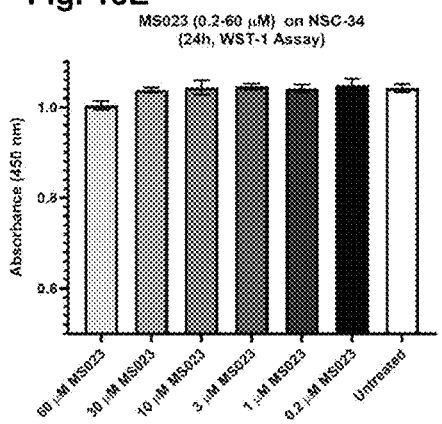
Figure 18F:
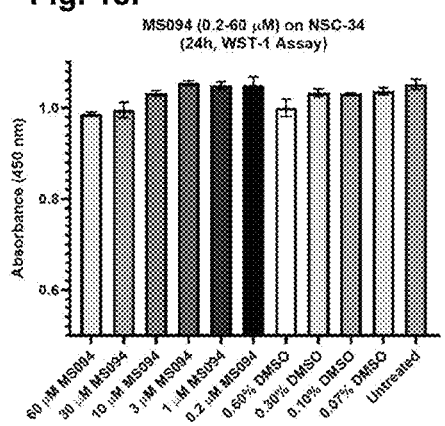
Figure 19A:
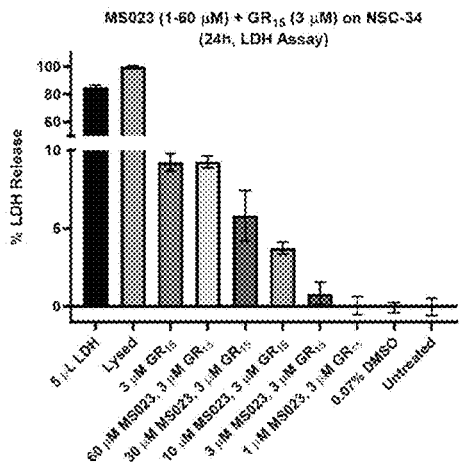
FIGS. 19A-19F are graphs comparing the activity of MS023 (0.2-60 PM) to abrogate cytotoxicity produced by $GR_{15}$ (SEQ ID NO: 1) (3 μM) (FIGS. 19A and 19B) and $PR_{15}$ (SEQ ID NO: 2) (3 μM) (FIGS. 19C and 19D) measured by LDH assay with negative control MS094 (0.2-60 μM) (FIGS. 19E and 19F).
Figure 19B:
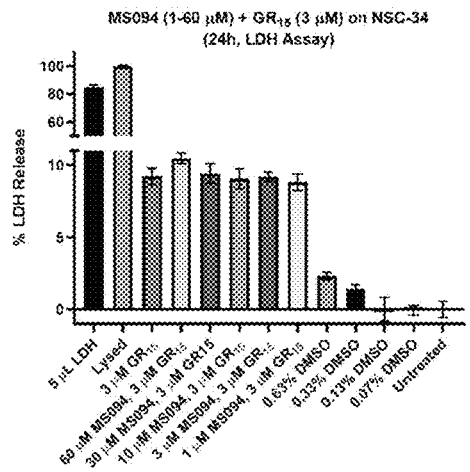
Figure 19C:
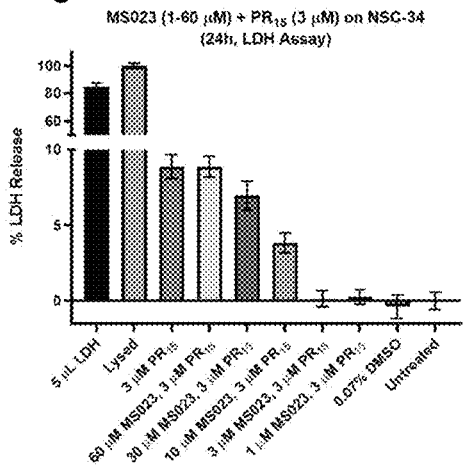
Figure 19D:
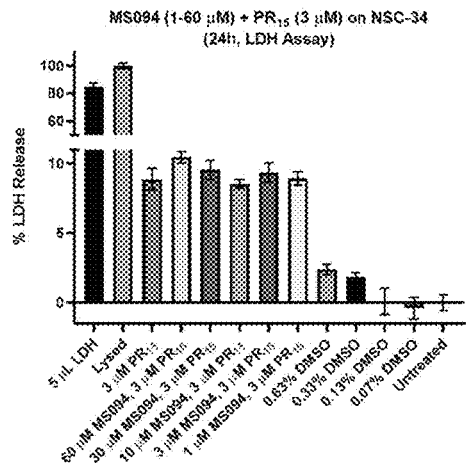
Figure 19E:
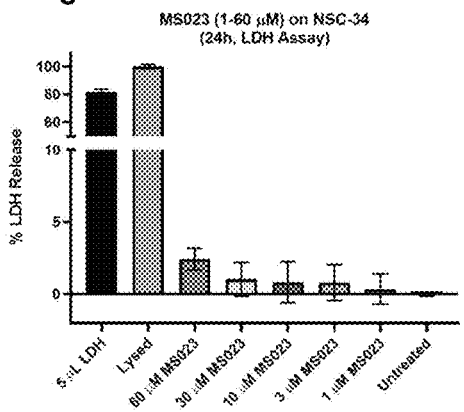
Figure 19F:
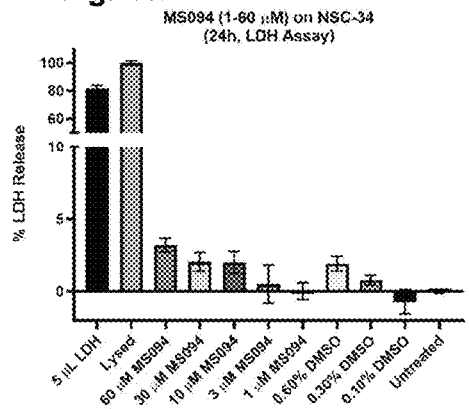
Figure 20A:
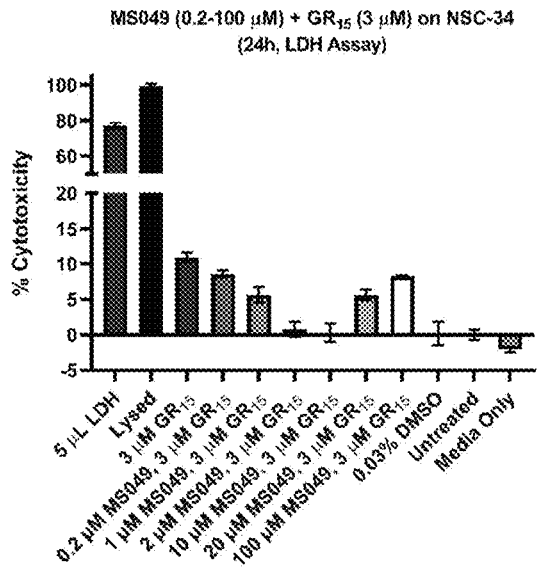
FIGS. 20A-20D are graphs comparing the activity of MS049 (0.2-100 PM) to abrogate cytotoxicity produced by $GR_{15}$ (SEQ ID NO: 1) (3 μM) (FIGS. 20A and 20B) and $PR_{15}$ (SEQ ID NO: 2) (3 μM) (FIGS. 20C and 20D) measured by LDH assay.
Figure 20B:
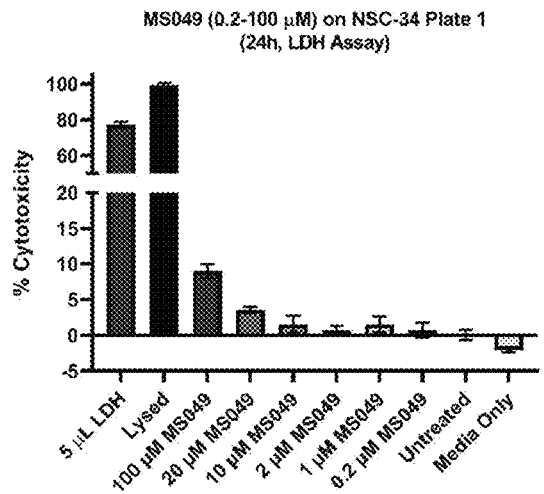
Figure 20C:
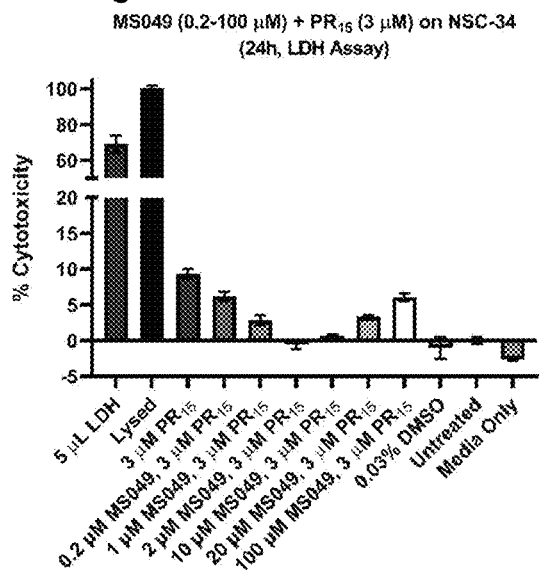
Figure 20D:
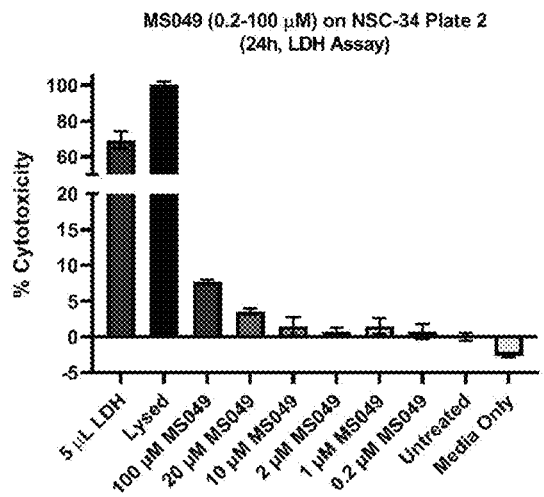
Figure 21A:
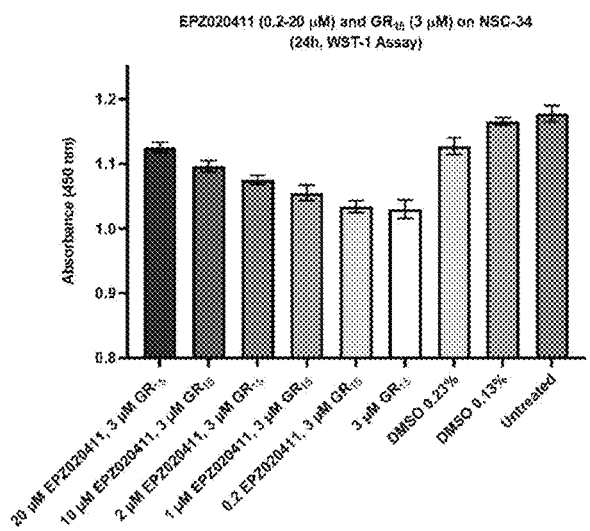
FIGS. 21A-21D are graphs comparing the activity of EPZ020411 (0.2-20 μM) to abrogate dysmetabolism produced by $GR_{15}$ (SEQ ID NO: 1) (3 μM) (FIGS. 21A and 21B) and $PR_{15}$ (SEQ ID NO: 2) (3 μM) (FIGS. 21C and 21D) measured by WST-1 assay.
Figure 21B:
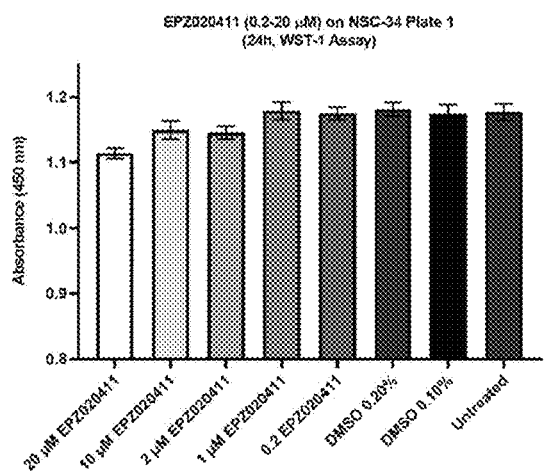
Figure 21C:
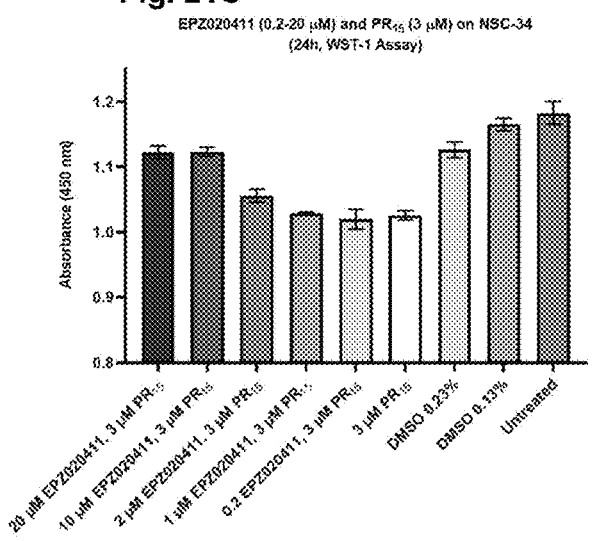
Figure 21D:
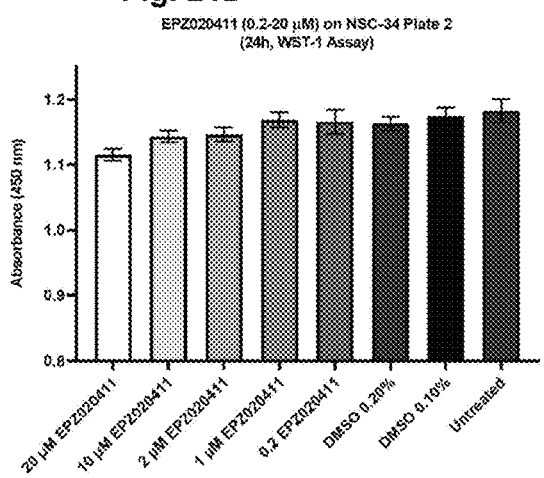
Figure 22A:
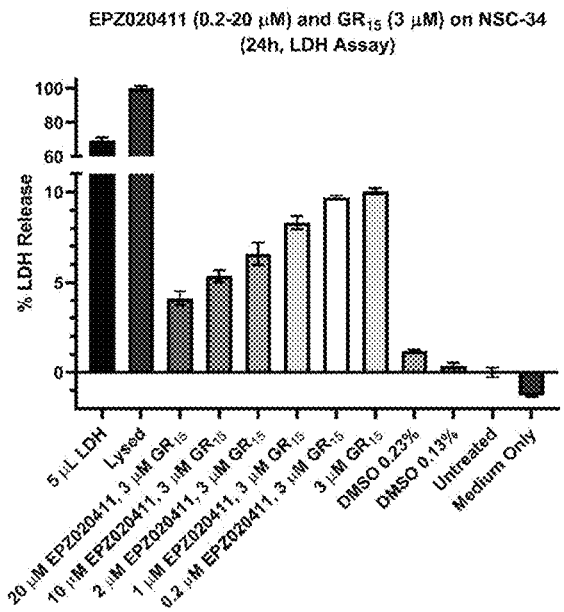
FIGS. 22A-22D are graphs comparing the activity of EPZ020411 (0.2-20 PM) to abrogate cytotoxicity produced by $GR_{15}$ (SEQ ID NO: 1) (3 μM) (FIGS. 22A and 22B) and $PR_{15}$ (SEQ ID NO: 2) (3 μM) (FIGS. 22C and 22D) measured by LDH assay.
Figure 22B:
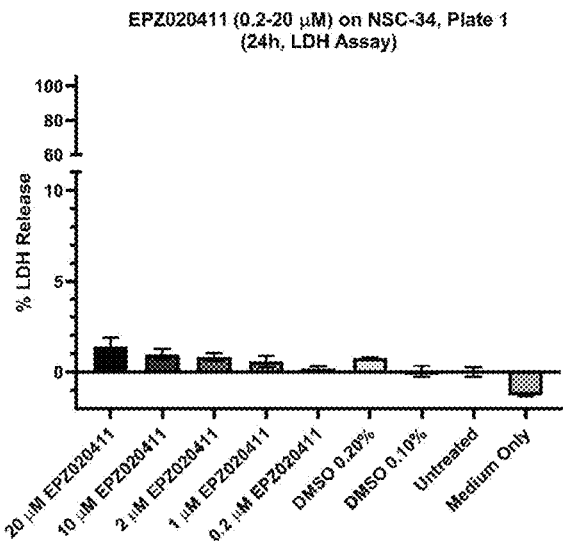
Figure 22C:
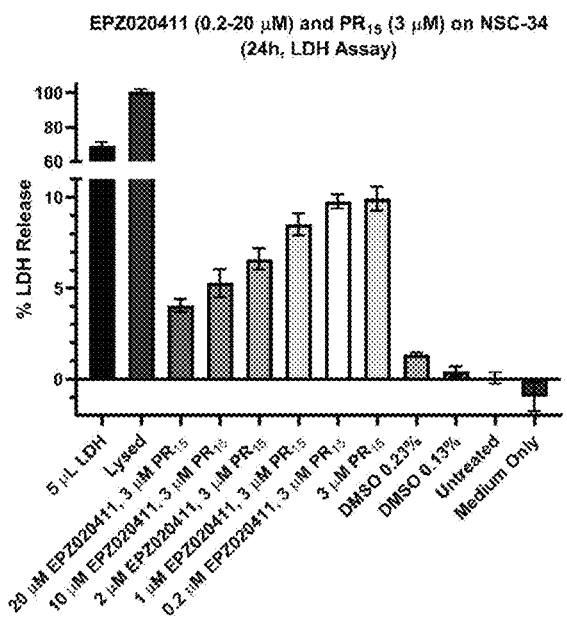
Figure 22D:
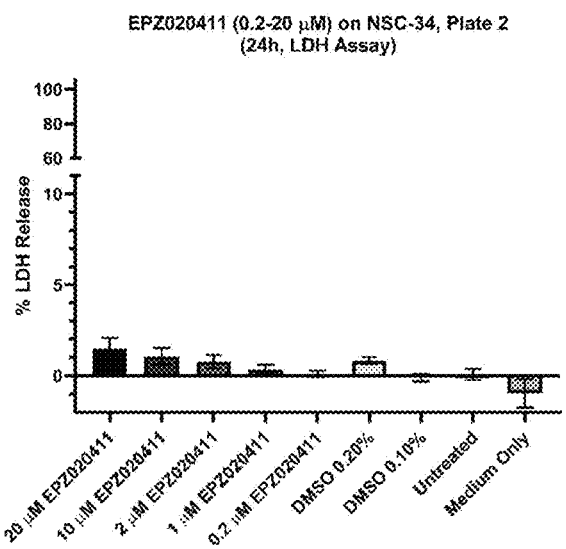
Figure 23A:
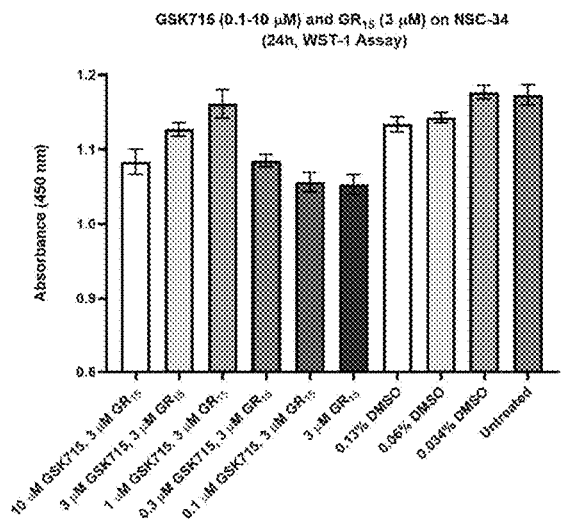
FIGS. 23A-23F are graphs comparing the activity of GSK3368715 (0.1-10 PM) to abrogated dysmetabolism produced by $GR_{15}$ (SEQ ID NO: 1) (3 μM) (FIGS. 23A and 23B) and $PR_{15}$ (SEQ ID NO: 2) (3 μM) (FIGS. 23C and 23D) measured by WST-1 assay with 0.10% DMSO controls (FIGS. 23E and 23F).
Figure 23B:
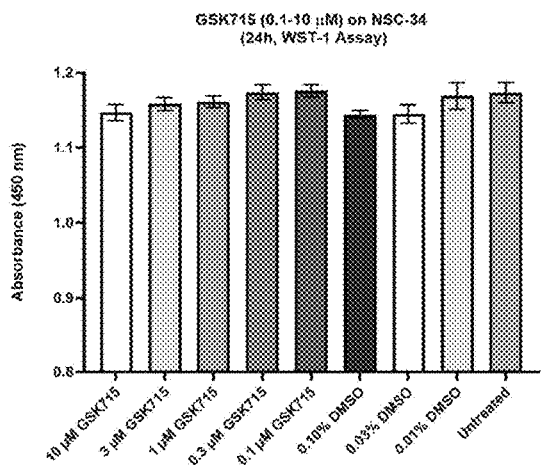
Figure 23C:
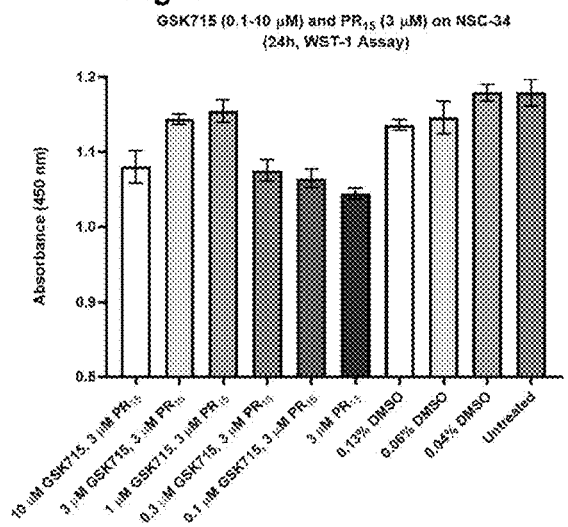
Figure 23D:
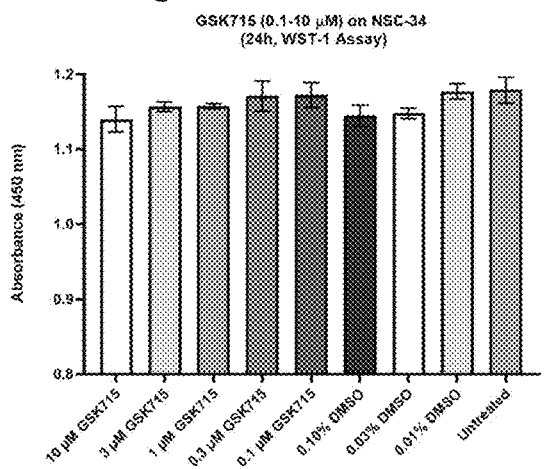
Figure 23E:
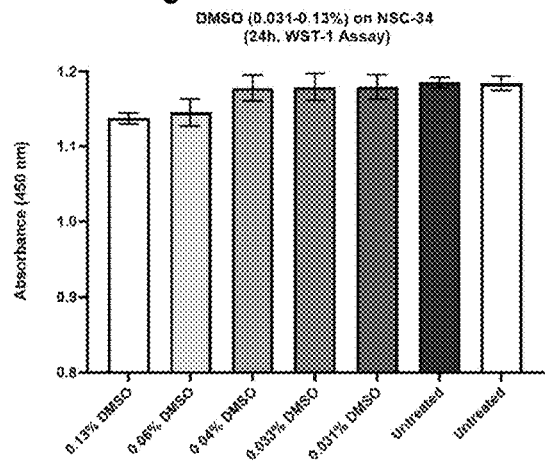
Figure 23F:
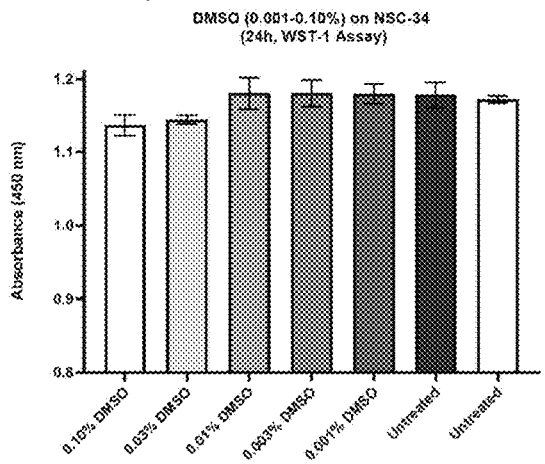
Figure 24A:
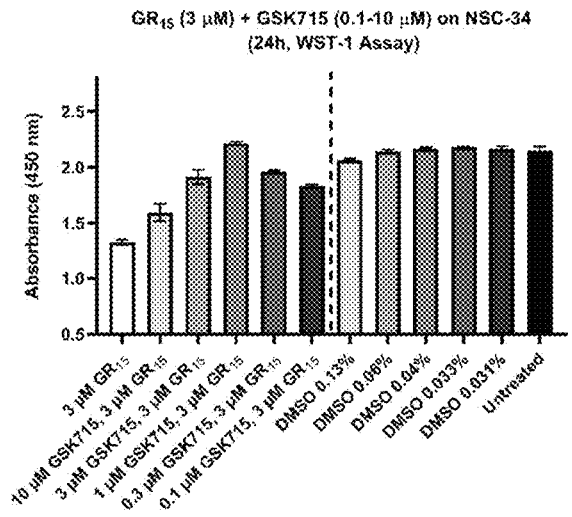
FIGS. 24A-24D are graphs comparing the activity of GSK3368715 (0.1-10 PM) (FIGS. 24A and 24B) and MS023 (0.1-10 μM) (FIGS. 24C and 24D) to abrogate dysmetabolism produced by $GR_{15}$ (SEQ ID NO: 1) (3 μM) measured by WST-1 assay.
Figure 24B:
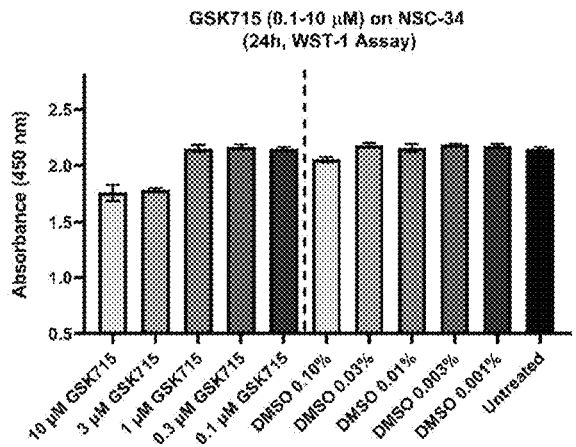
Figure 24C:
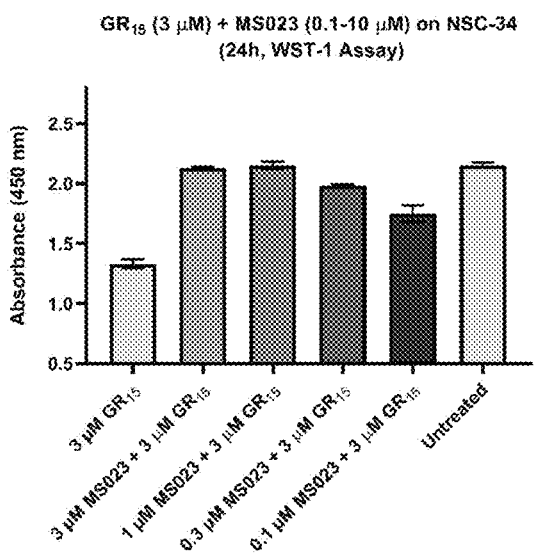
Figure 24D:
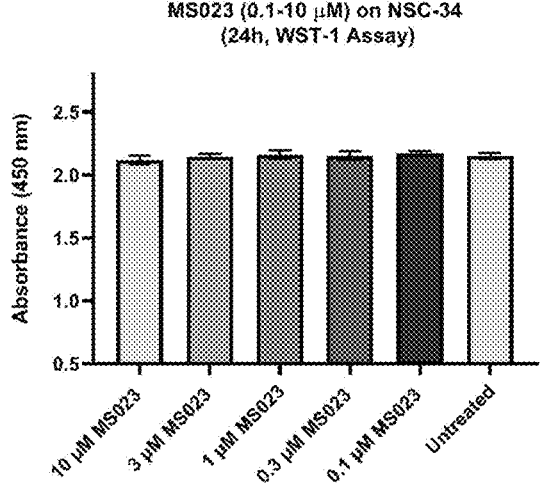
Figure 25A:
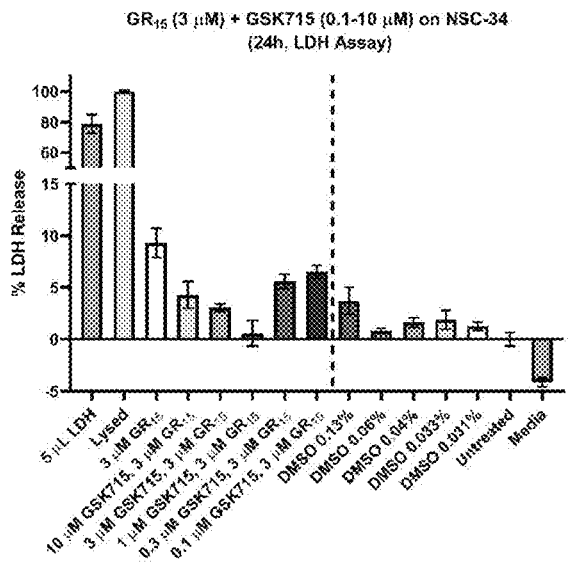
FIGS. 25A-25D are graphs comparing the activity of GSK3368715 (0.1-10 PM) to abrogate cytotoxicity produced by $GR_{15}$ (SEQ ID NO: 1) (3 μM) (FIGS. 25A and 25B) and $PR_{15}$ (SEQ ID NO: 2) (3 μM) (FIGS. 25C and 25D) measured by LDH assay.
Figure 25B:
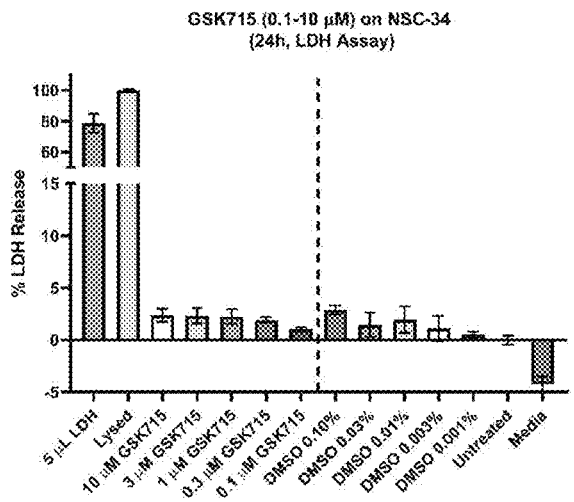
Figure 25C:
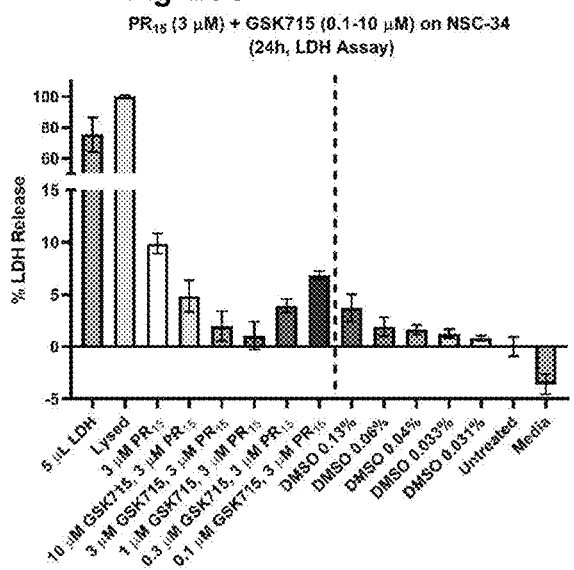
Figure 25D:
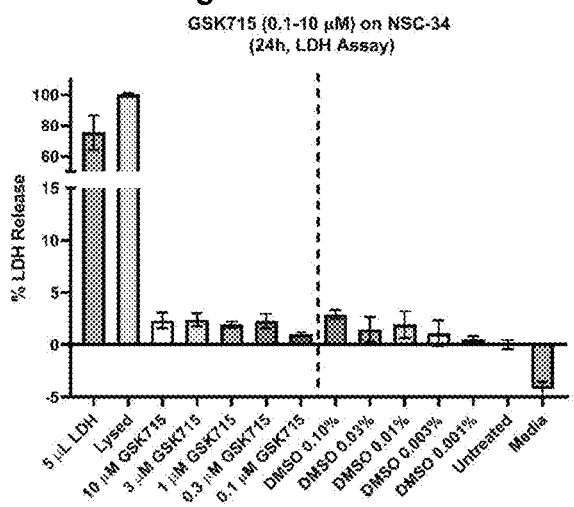
Figure 26A:
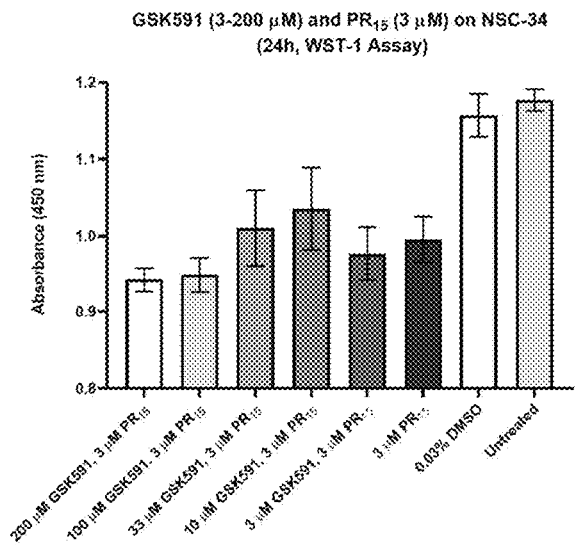
FIGS. 26A-26D are graphs comparing the activity of GSK591 (3-200 μM) (FIGS. 26A and 26B) and MS023 (0.1-60 μM) (FIGS. 26C and 26D) to abrogate dysmetabolism produced by $PR_{15}$ (SEQ ID NO: 2) (3 μM) measured by WST-1 assay.
Figure 26B:
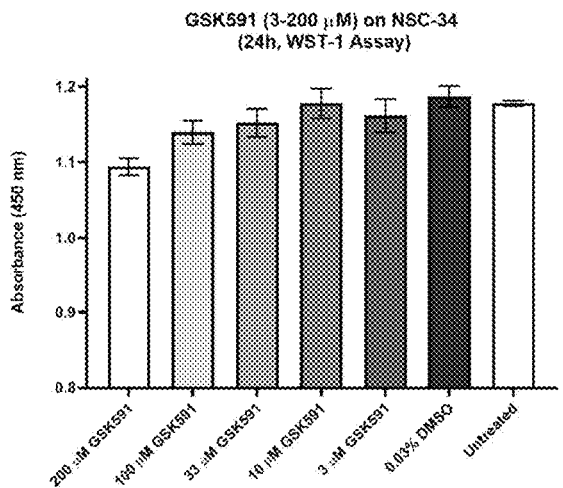
Figure 26C:
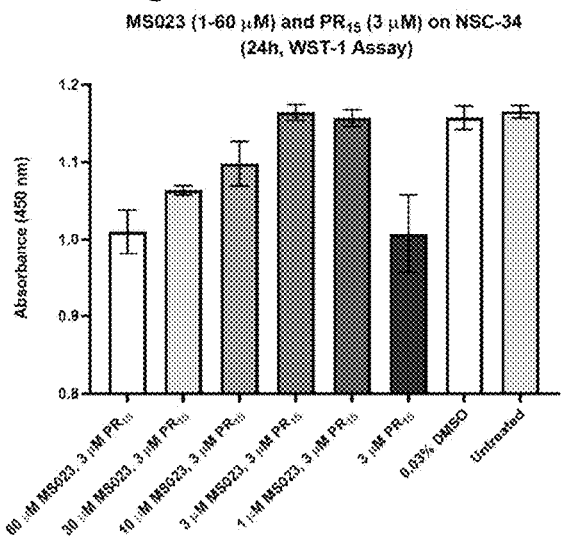
Figure 26D:
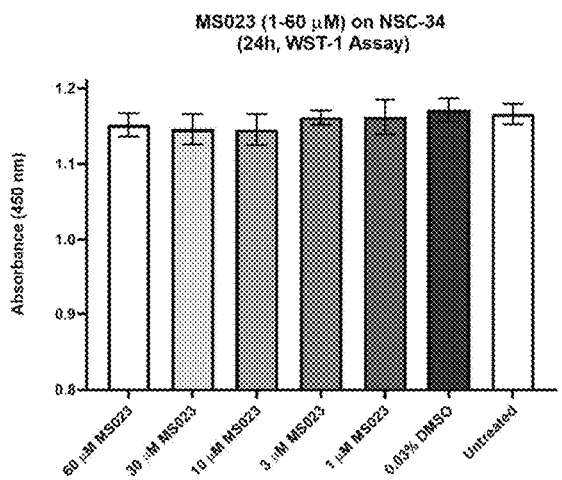
Figure 27A:
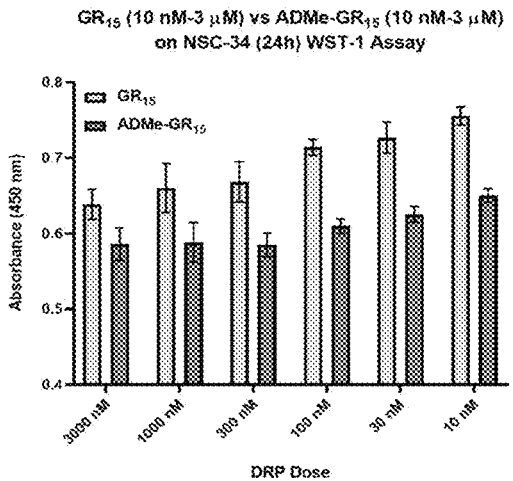
FIGS. 27A-27E are graphs comparing the dose-response patterns of dysmetabolism produced by $GR_{is}$ (SEQ ID NO: 1) and Asymmetrically Dimethylated (ADMe)-$GR_{15}$ (SEQ ID NO: 1) measured by WST-1 assay.
Figure 27B:
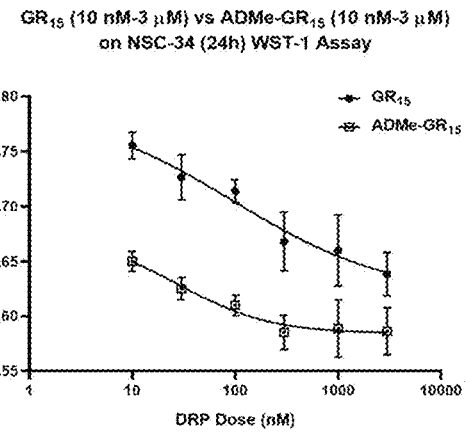
Figure 27C:
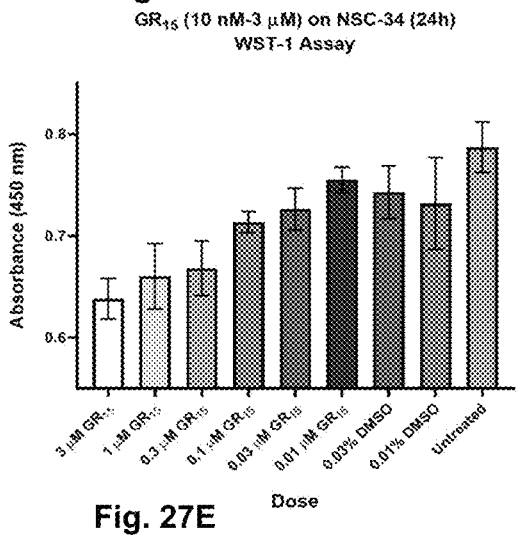
Figure 27D:
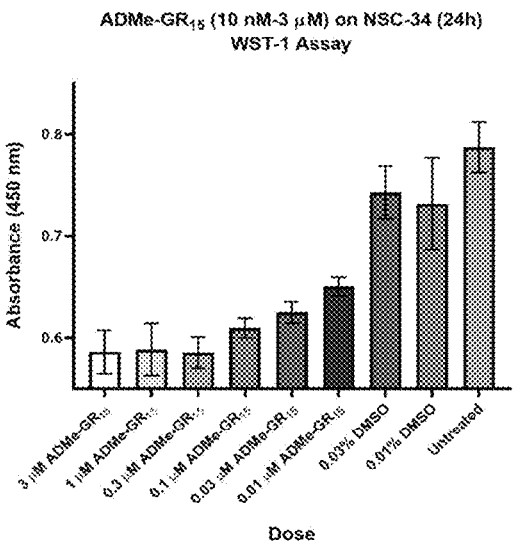
Figure 27E:
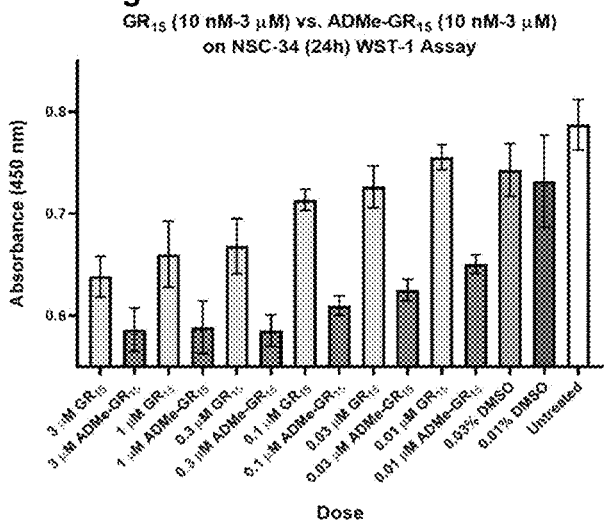
Figure 28A:
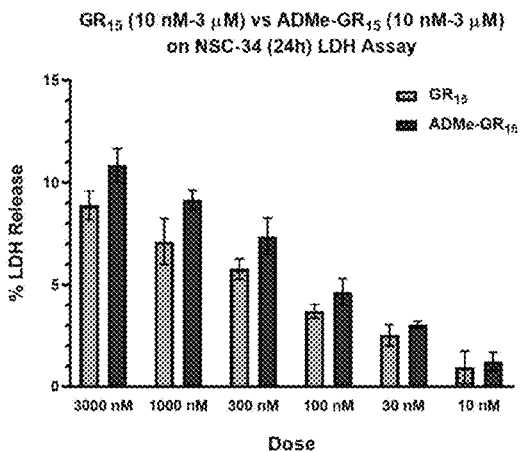
FIGS. 28A-28E are graphs comparing the dose-response patterns of cytotoxicity produced by $GR_{is}$ (SEQ ID NO: 1) and Asymmetrically Dimethylated (ADMe)-$GR_{is}$ (SEQ ID NO: 1) measured by LDH assay.
Figure 28B:
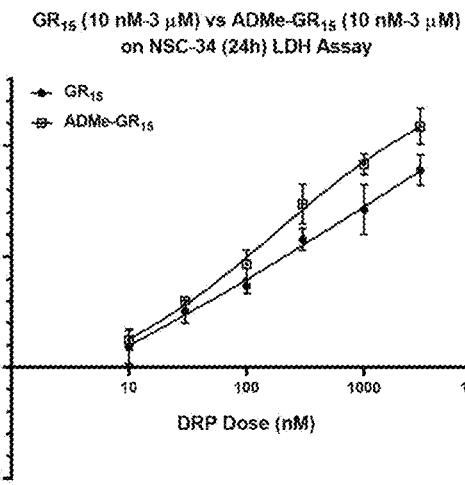
Figure 28C:
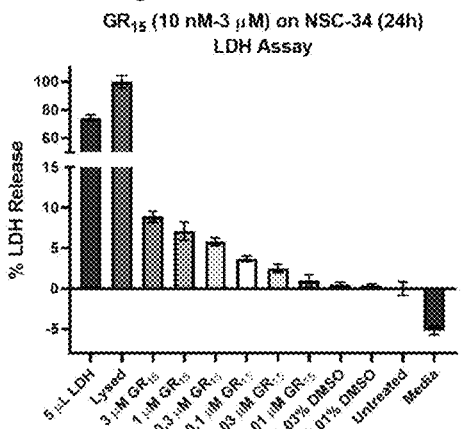
Figure 28D:
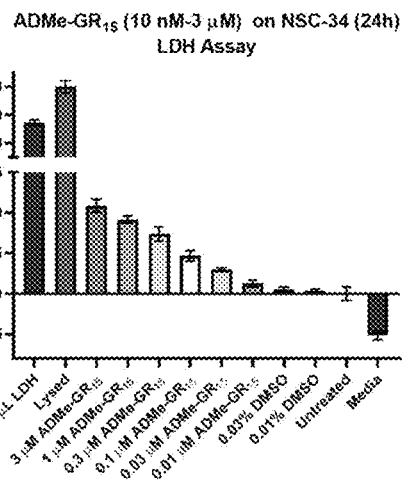
Figure 28E:
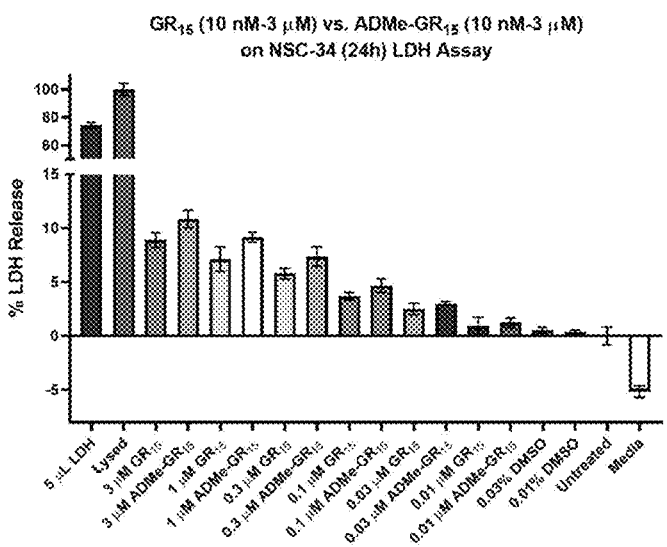
Figure 29A:
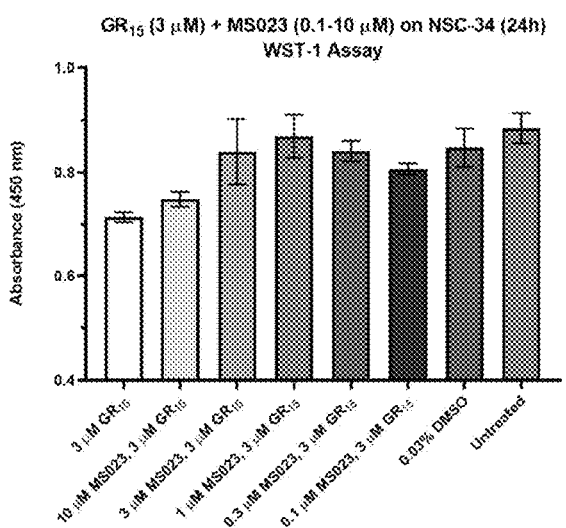
FIGS. 29A-29D, 30A-30D, and 31A-31D are graphs comparing the activity of MS023 (0.1-10 μM) to abrogate dysmetabolism produced by $GR_{15}$ (SEQ ID NO: 1) and ADMe-$GR_{15}$ (SEQ ID NO: 1) (3 μM) measured by WST-1 assay and repeated separately on three different dates.
Figure 29B:
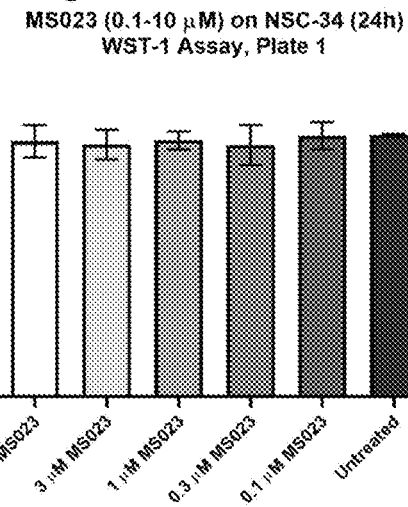
Figure 29C:
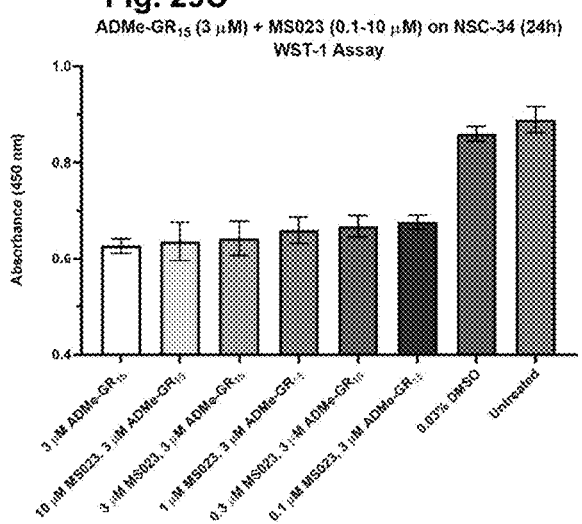
Figure 29D:
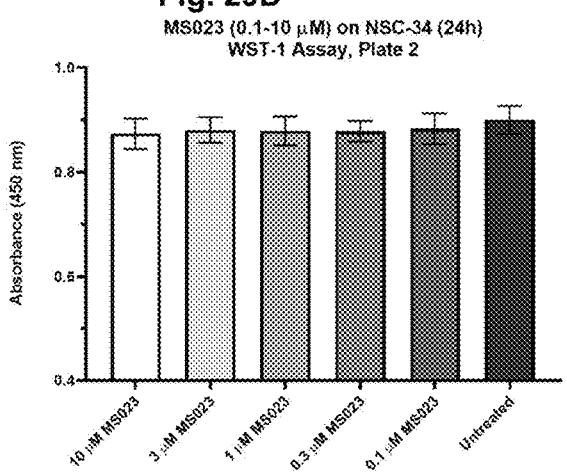
Figure 30A:
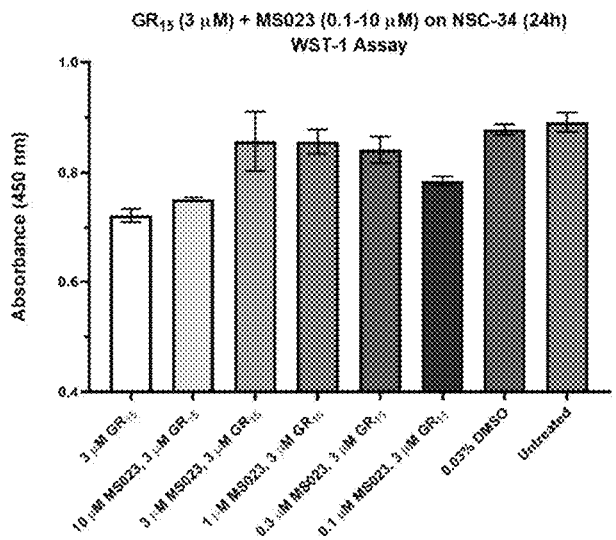
Figure 30B:
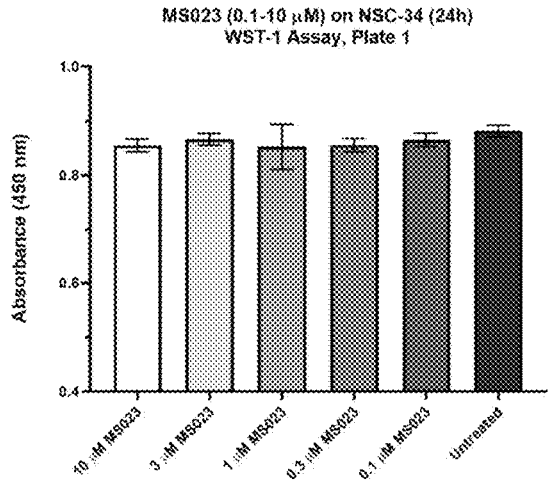
Figure 30C:
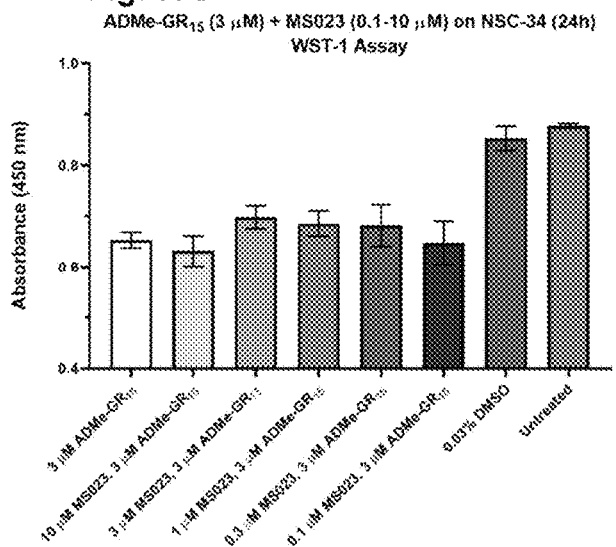
Figure 30D:
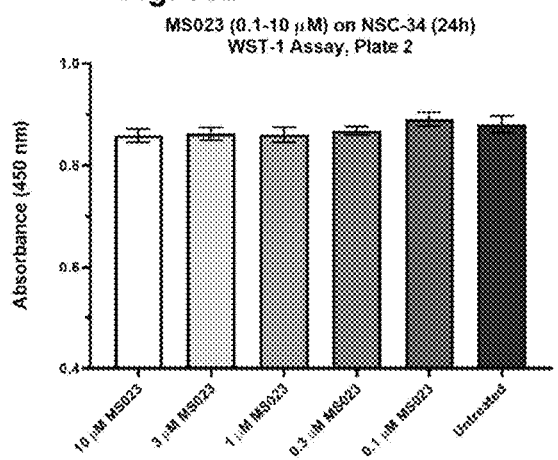
Figure 31A:
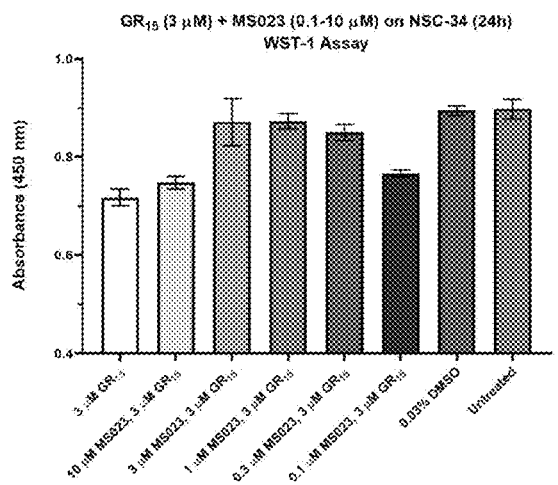
Figure 31B:
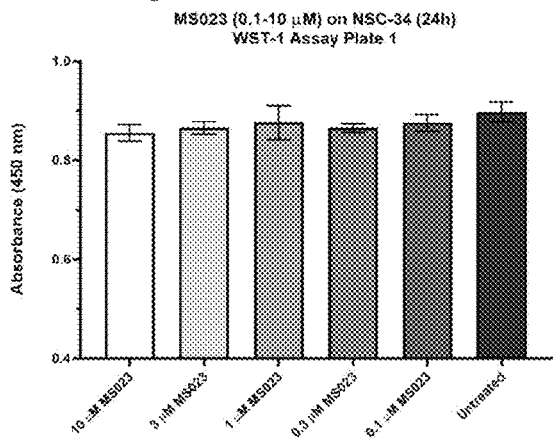
Figure 31C:
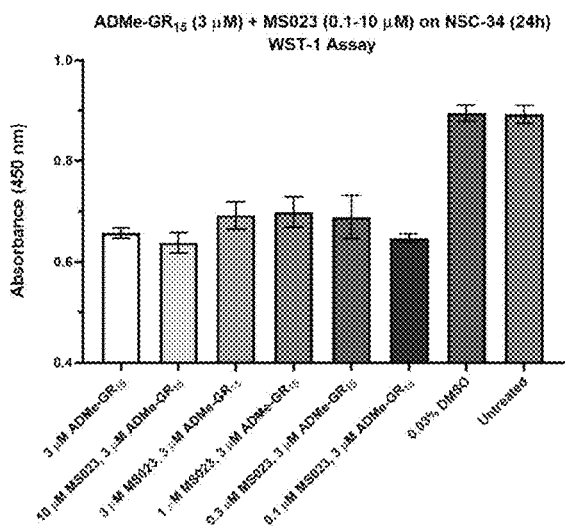
Figure 31D:
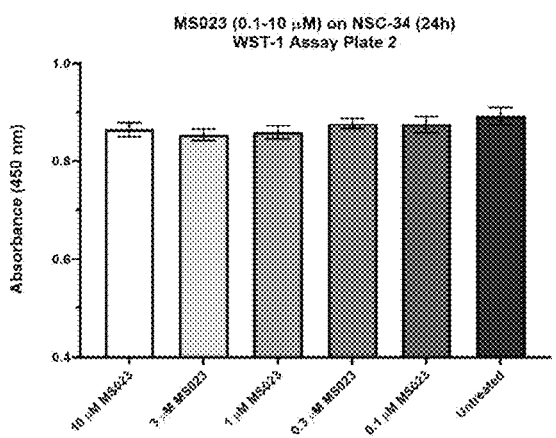
Figure 32A:
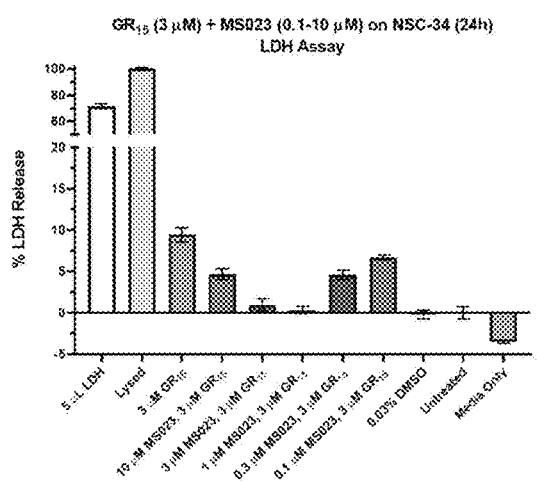
FIGS. 32A-32D are graphs comparing the activity of MS023 (0.1-10 μM) to abrogate cytotoxicity produced by $GR_{15}$ (SEQ ID NO: 1) (3 μM) (FIGS. 32A and 32B) and ADMe-$GR_{15}$ (SEQ ID NO: 1) (3 μM) (FIGS. 32C and 32D) measured by LDH assay.
Figure 32B:
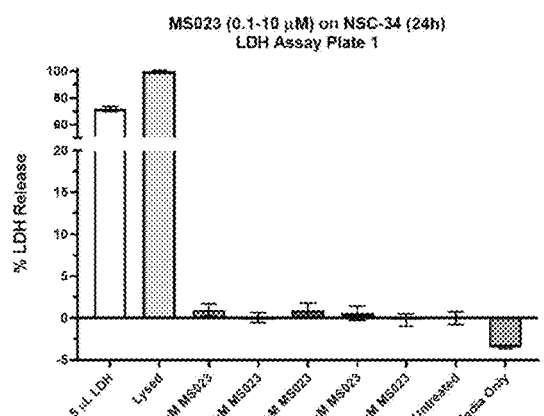
Figure 32C:
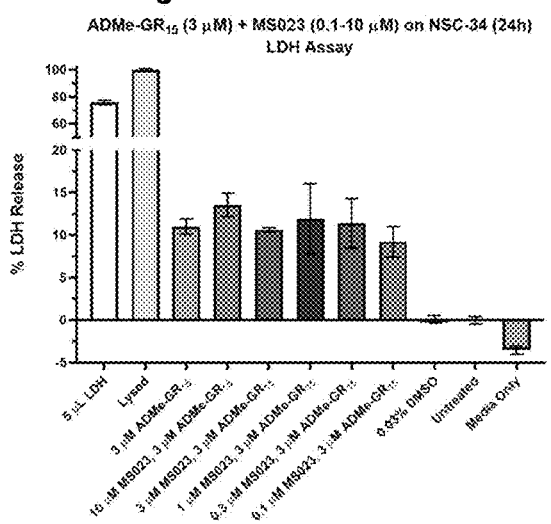
Figure 32D:
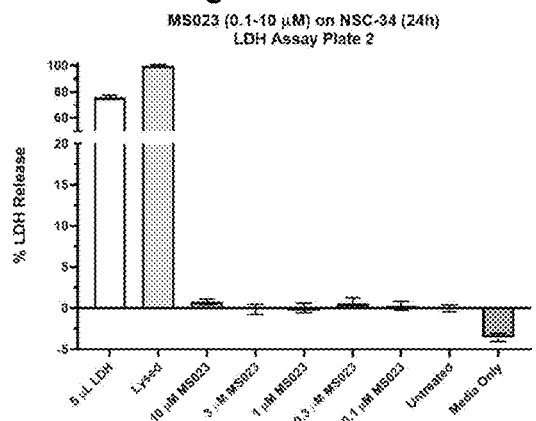

As shown in FIG. 17, when compared to untreated cells, all conditions were significantly decreased in their 800/700 readout. With 24 hour treatment, MS049 decreased asymmetrical arginine methylation of NSC-34 cells by approximately 17% at 1 µM and 39% at 100 µM.

Example 18: MS023 (0.2-60 µM) and Negative Control MS094 (0.2-60 µM) and Abrogation of Dysmetabolism Produced by $GR_{15}$ (SEQ ID NO: 1) and $PR_{15}$ (SEQ ID NO: 2) (3 µM) Measured by WST-1 Assay Cells were plated in culture medium in 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. 10 mM stocks of MS023 and MS094 were thawed to room temperature and diluted in warm culture medium to achieve final concentrations of 0.2, 1, 3, 10, 30, and 60 µM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Controls (Cells treated either equivalent DMSO to MS094-treated wells, equivalent DMSO to MS094 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 µM $GR_{15}$) (SEQ ID NO: 1)
Cells treated with 3 µM $GR_{15}$ (SEQ ID NO: 1) and one of the following doses of MS023: 60 µM, 30 µM, 10 µM, 3 µM, 1 µM, 0.2 µM.
Cells treated with 3 µM $GR_{15}$ (SEQ ID NO: 1) and one of the following doses of negative control MS094: 60 µM, 30 µM, 10 µM, 3 µM, 1 µM, 0.2 µM.
PR Only (Cells treated only with 3 µM $PR_{15}$) (SEQ ID NO: 2)
Cells treated with 3 µM $PR_{15}$ (SEQ ID NO: 2) and one of the following doses of MS023: 60 µM, 30 µM, 10 µM, 3 µM, 1 µM, 0.2 µM.
Cells treated with 3 µM $PR_{15}$ (SEQ ID NO: 2) and one of the following doses of negative control MS094: 60 µM, 30 µM, 10 µM, 3 µM, 1 µM, 0.2 µM.
Cells treated with only one of the following doses of MS023: 60 µM, 30 µM, 10 µM, 3 µM, 1 µM, 0.2 µM.
Cells treated with only one of the following doses of negative control MS094: 60 µM, 30 µM, 10 µM, 3 µM, 1 µM., 0.2 µM.

Plates were incubated for 24h at 37° C., 5% $CO_2$. Immediately before testing, culture medium was removed and replaced with 200 µL PBS-Glucose solution (4.5 g/L, sterile) that had been warmed from 4° in a 37° C. water bath. WST-1 reagent aliquots were thawed from −20° C. and equilibrated to room temperature before use. 20 µL WST-1 reagent was added per well containing 200 µL PBS-Glucose. Plates were incubated with WST-1 at 37° C., 5% $CO_2$ for 1h before one absorbance reading at 450 nm being taken on a Molecular Devices SpectraMax M3 µlate reader. Data was exported from plate reader's SoftMax Pro 7.0 software into an excel file.

As shown in FIGS. 18A-18F, MS023 dose-dependently abrogated both GR and PR-induced dysmetabolism. 3 µM and 1 µM doses of MS023 completely abrogated dysmetabolism induced by 3 µM $GR_{15}$ (SEQ ID NO: 1) or $PR_{15}$ (SEQ ID NO: 2) challenge. No doses of negative control MS094 abrogated dysmetabolism induced by $GR_{15}$ (SEQ ID NO: 1) or $PR_{15}$ (SEQ ID NO: 2) challenge. The two highest doses of negative control MS094 tested, 30 and 60 µM, produced dysmetabolism as compared to untreated controls, however this is likely attributed to DMSO-related toxicity, which is also visible in the DMSO controls corresponding to those doses (0.30% and 0.60% DMSO).

Example 19: MS023 (0.2-60 µM) and Negative Control MS094 (0.2-60 µM) and Abrogation of Cytotoxicity Produced by $GR_{15}$ (SEQ ID NO: 1) and $PR_{15}$ (SEQ ID NO: 2) (3 µM) Measured by LDH Assay Cells were plated in culture medium in 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. 10 mM stocks of MS023 and MS094 were thawed to room temperature and diluted in warm culture medium to achieve final concentrations of 0.2, 1, 3, 10, 30, and 60 µM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Controls (Cells treated either equivalent DMSO to MS094-treated wells, equivalent DMSO to MS094 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 µM $GR_{15}$) (SEQ ID NO: 1)
Cells treated with 3 µM $GR_{15}$ (SEQ ID NO: 1) and one of the following doses of MS023: 60 µM, 30 µM, 10 µM, 3 µM, 1 µM, 0.2 µM.
Cells treated with 3 µM $GR_{15}$ (SEQ ID NO: 1) and one of the following doses of negative control MS094: 60 µM, 30 µM, 10 µM, 3 µM, 1 µM, 0.2 µM.
PR Only (Cells treated only with 3 µM $PR_{15}$) (SEQ ID NO: 2)
Cells treated with 3 µM $PR_{15}$ (SEQ ID NO: 2) and one of the following doses of MS023: 60 µM, 30 µM, 10 µM, 3 µM, 1 µM, 0.2 µM.
Cells treated with 3 µM $PR_{15}$ (SEQ ID NO: 2) and one of the following doses of negative control MS094: 60 µM, 30 µM, 10 µM, 3 µM, 1 µM, 0.2 µM.
Cells treated with only one of the following doses of MS023: 60 µM, 30 µM, 10 µM, 3 µM, 1 µM, 0.2 µM.
Cells treated with only one of the following doses of negative control MS094: 60 µM, 30 µM, 10 µM, 3 µM, 1 µM, 0.2 µM.
High control/"100% toxicity" (Cells lysed with lysis buffer)
Positive control (5 µL LDH solution)

Plates were incubated for 24h at 37° C., 5% $CO_2$. Cells were tested and data were analyzed using the procedure detailed in LDH assay kit instructions.

As shown in FIGS. 19A-19F, MS023 dose-dependently abrogated both GR and PR-induced cytotoxicity (measured as % LDH release). 3 µM and 1 µM doses of MS023 completely abrogated cytotoxicity induced by 3 µM $GR_{15}$ (SEQ ID NO: 1) or $PR_{15}$ (SEQ ID NO: 2) challenge. No doses of negative control MS094 abrogated cytotoxicity induced by $GR_{15}$ (SEQ ID NO: 1) or $PR_{15}$ (SEQ ID NO: 2) challenge. The highest dose of MS023, 60 µM, did produce significant cytotoxicity, however, this was not one of the doses shown to completely abrogate cytotoxicity induced by $GR_{15}$ (SEQ ID NO: 1) or $PR_{15}$ (SEQ ID NO: 2) challenge. The three highest doses of negative control MS094 tested, 10, 30 and 60 µM, produced cytotoxicity as compared to untreated controls, however at the highest 2 doses this is likely attributed to DMSO-related toxicity, which is also visible in the DMSO controls corresponding to those doses (0.30%, and 0.60% DMSO).

Example 20: MS049 (0.2-100 µM) and Abrogation of Cytotoxicity Produced by $GR_{15}$ (SEQ ID NO: 1) and $PR_{15}$ (SEQ ID NO: 2) (3 µM) Measured by LDH Assay Cells were plated in culture medium in 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. A 10 mM stock of MS049 was thawed to room temperature and diluted in warm culture medium to achieve final concentrations of 0.2, 1, 2, 10, 20, and 100 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated only with the amount of DMSO that GR- and PR-treated cells were exposed to)
GR Only (Cells treated only with 3 μM $GR_{15}$) (SEQ ID NO: 1)
Cells treated with 3 μM $GR_{15}$ (SEQ ID NO: 1) and one of the following doses of MS049: 100 μM, 20 μM, 10 μM, 2 μM, 1 μM, 0.2 μM.
PR Only (Cells treated only with 3 μM $PR_{15}$) (SEQ ID NO: 2)
Cells treated with 3 μM $PR_{15}$ (SEQ ID NO: 2) and one of the following doses of MS049: 100 μM, 20 μM, 10 μM, 2 μM, 1 μM, 0.2 μM.
Cells treated with only one of the following doses of MS049: 100 μM, 20 μM, 10 μM, 2 μM, 1 μM, 0.2 μM.
High control/"100% toxicity" (Cells lysed with lysis buffer)
Positive control (5 μL LDH solution)

Cells were tested and data were analyzed using the procedure detailed in LDH assay kit instructions.

As shown in FIGS. 20A-20D, MS049 dose-dependently abrogated both $GR_{15}$ (SEQ ID NO: 1) and $PR_{15}$-(SEQ ID NO: 2) induced cytotoxicity. MS049 partially abrogated $GR_{15}$ (SEQ ID NO: 1) and $PR_{15}$-(SEQ ID NO: 2) induced cytotoxicity at doses of 1 and 20 μM, and completely abrogated $GR_{15}$ (SEQ ID NO: 1) and $PR_{15}$-(SEQ ID NO: 2) induced cytotoxicity at doses of 2 and 10 μM. MS049 did cause significant cytotoxicity independently of GR and PR challenge at doses of 100 and 20 μM, but not at other doses tested.

Example 21: EPZ020411 (0.2-20 μM) and Abrogation of Dysmetabolism Produced by $GR_{15}$ (SEQ ID NO: 1) and $PR_{15}$ (SEQ ID NO: 2) (3 μM) Measured by WST-1 Assay Cells were plated in culture medium in 96-well plates at a density of $3.7 \times 10^4$ cells per well and incubated overnight at 37° C., 5% $CO_2$. The following day, immediately prior to addition of test compounds, existing culture medium was removed and replaced with staggered volumes of culture medium as in Example 1. A 10 mM stock of EPZ020411 was thawed to room temperature and diluted in warm culture medium to achieve final concentrations of 0.2, 1, 2, 10, and 20 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with either equivalent DMSO to EPZ020411-treated wells, equivalent DMSO to EPZ020411 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 μM $GR_{15}$) (SEQ ID NO: 1)
Cells treated with 3 μM $GR_{15}$ (SEQ ID NO: 1) and one of the following doses of EPZ020411: 20 μM, 10 μM, 2 μM, 1 μM, 0.2 μM.
PR Only (Cells treated only with 3 μM $PR_{15}$) (SEQ ID NO: 2)
Cells treated with 3 μM $PR_{15}$ (SEQ ID NO: 2) and one of the following doses of EPZ020411: 20 μM, 10 μM, 2 μM, 1 μM, 0.2 μM.
Cells treated with only one of the following doses of EPZ020411: 20 μM, 10 μM, 2 μM, 1 μM, 0.2 μM.

Plates were incubated for 24h at 37° C., 5% $CO_2$. Immediately before testing, culture medium was removed and replaced with 200 μL PBS-Glucose solution (4.5 g/L, sterile) that had been warmed from 4° in a 37° C. water bath. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% $CO_2$ for 1h before one absorbance reading at 450 nm being taken on a Molecular Devices SpectraMax M3 μlate reader. Data was exported from plate reader's SoftMax Pro 7.0 software into an excel file.

As shown in FIGS. 21A-21D, EPZ020411 dose-dependently abrogated both $GR_{15}$ (SEQ ID NO: 1) and $PR_{15}$-(SEQ ID NO: 2) induced dysmetabolism. EPZ020411 partially abrogated $GR_{15}$ (SEQ ID NO: 1) induced dysmetabolism at doses of 2, 10, and 20 μM, with the greatest abrogation at 20 μM. Additionally, it completely abrogated $PR_{15}$-(SEQ ID NO: 2) induced dysmetabolism at doses of 10 and 20 μM. EPZ020411 did cause significant dysmetabolism independently of GR and PR challenge at doses of 10 and 20 μM, but not at other doses tested. This cannot be attributed to DMSO-induced dysmetabolism, as corresponding DMSO controls (0.10%, 0.20% DMSO) did not induce dysmetabolism.

Example 22: EPZ020411 (0.2-20 μM) and Abrogation of Cytotoxicity Produced by $GR_{15}$ (SEQ ID NO: 1) and $PR_{15}$ (SEQ ID NO: 2) (3 μM) Measured by LDH Assay Cells were plated in culture medium in 96-well plates at a density of $3.7 \times 10^4$ cells per well and incubated overnight at 37° C., 5% $CO_2$. The following day, immediately prior to addition of test compounds, existing culture medium was removed and replaced with staggered volumes of culture medium as in Example 1. A 10 mM stock of EPZ020411 was thawed to room temperature and diluted in warm culture medium to achieve final concentrations of 0.2, 1, 2, 10, and 20 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with either equivalent DMSO to EPZ020411-treated wells, equivalent DMSO to EPZ020411 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 μM $GR_{15}$) (SEQ ID NO: 1)
Cells treated with 3 μM $GR_{15}$ (SEQ ID NO: 1) and one of the following doses of EPZ020411: 20 μM, 10 μM, 2 μM, 1 μM, 0.2 μM.
PR Only (Cells treated only with 3 μM $PR_{15}$) (SEQ ID NO: 2)
Cells treated with 3 μM $PR_{15}$ (SEQ ID NO: 2) and one of the following doses of EPZ020411: 20 μM, 10 μM, 2 μM, 1 μM, 0.2 μM.
Cells treated with only one of the following doses of EPZ020411: 20 μM, 10 μM, 2 μM, 1 μM, 0.2 μM.
High control/"100% toxicity" (Cells lysed with lysis buffer)
Positive control (5 μL LDH solution)

Plates were incubated for 24h at 37° C., 5% $CO_2$. Cells were tested and data were analyzed using the procedure detailed in LDH assay kit instructions.

As shown in FIGS. 22A-22D, EPZ020411 dose-dependently abrogated both $GR_{15}$ (SEQ ID NO: 1) and $PR_{15}$-(SEQ ID NO: 2) induced cytotoxicity. EPZ020411 partially abrogated $GR_{15}$ (SEQ ID NO: 1) and $PR_{15}$-(SEQ ID NO: 2) induced cytotoxicity at all doses but 0.2 μM, with the greatest effect at a dose of 20 μM. EPZ020411 did cause significant cytotoxicity independently of GR and PR challenge at doses of 10 and 20 μM, but not at other doses tested. This cannot be fully attributed to DMSO-induced cytotoxicity, as only the DMSO control corresponding to the highest EPZ020411 dose (0.20% DMSO) produced slight cytotoxicity.

Example 23: GSK3368715 (0.1-10 μM) and Abrogation of Dysmetabolism Produced by $GR_{15}$ (SEQ ID NO: 1) and $PR_{15}$ (SEQ ID NO: 2) (3 μM) Measured by WST-1 Assay Cells were plated in culture medium in 96-well plates at a density of 3.7×10⁴ cells per well and incubated overnight at 37° C., 5% $CO_2$. The following day, immediately prior to addition of test compounds, existing culture medium was removed and replaced with staggered volumes of culture medium as in Example 1. A 10 mM stock of GSK3368715 was thawed to room temperature and diluted in warm culture medium to achieve final concentrations of 0.1, 0.3, 1, 3, and 10 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with either equivalent DMSO to GSK3368715-treated wells, equivalent DMSO to GSK3368715 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 μM $GR_{15}$) (SEQ ID NO: 1)
Cells treated with 3 μM $GR_{15}$ (SEQ ID NO: 1) and one of the following doses of GSK3368715: 10 μM, 3 μM, 1 μM, 0.3 μM, 0.1 μM.
PR Only (Cells treated only with 3 μM $PR_{15}$) (SEQ ID NO: 2)
Cells treated with 3 μM $PR_{15}$ (SEQ ID NO: 2) and one of the following doses of GSK3368715: 10 μM, 3 μM, 1 μM, 0.3 μM, 0.1 μM.
Cells treated with only one of the following doses of GSK3368715: 10 μM, 3 μM, 1 μM, 0.3 μM, 0.1 μM.

Plates were incubated for 24h at 37° C., 5% $CO_2$. Immediately before testing, culture medium was removed and replaced with 200 μL PBS-Glucose solution (4.5 g/L, sterile) that had been warmed from 4° in a 37° C. water bath. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% $CO_2$ for 1h before one absorbance reading at 450 nm being taken on a Molecular Devices SpectraMax M3 plate reader. Data was exported from plate reader's SoftMax Pro 7.0 software into an excel file.

As shown in FIGS. 23A-23F, GSK3368715 dose-dependently abrogated both $GR_{15}$ (SEQ ID NO: 1) and $PR_{15}$-(SEQ ID NO: 2) induced dysmetabolism. GSK3368715 completely abrogated $GR_{15}$ (SEQ ID NO: 1) and $PR_{15}$-(SEQ ID NO: 2) induced dysmetabolism at doses of 1 and 3 μM when compared to corresponding DMSO-treated controls (0.06%, 0.034% DMSO). The highest dose of GSK3368715 tested, 10 μM, induced low levels of dysmetabolism independently of GR15 (SEQ ID NO: 1) and PR15 (SEQ ID NO: 2) challenge, however this can likely be attributed to solvent effects, as corresponding 0.10% DMSO controls displayed similar levels of dysmetabolism.

Example 24: MS023 (0.1-10 μM) and GSK3368715 (0.1-10 μM) and Abrogation of Dysmetabolism Produced by $GR_{15}$ (SEQ ID NO: 1) (3 μM) Measured by WST-1 Assay Cells were plated in culture medium in 96-well plates at a density of 3.7×10⁴ cells per well and incubated overnight at 37° C., 5% $CO_2$. The following day, immediately prior to addition of test compounds, existing culture medium was removed and replaced with staggered volumes of culture medium as in Example 1. 10 mM stocks of MS023 and GSK3368715 were thawed to room temperature and diluted in warm culture medium to achieve final concentrations of 0.1, 0.3, 1, 3, and 10 μM in plate. A 10 mM stock of $GR_{15}$ (SEQ ID NO: 1)was equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with either equivalent DMSO to GSK3368715-treated wells, equivalent DMSO to GSK3368715 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 μM $GR_{15}$) (SEQ ID NO: 1)
Cells treated with 3 μM $GR_{15}$ (SEQ ID NO: 1) and one of the following doses of MS023: 10 μM, 3 μM, 1 μM, 0.3 μM, 0.1 μM.
Cells treated with 3 μM $GR_{15}$ (SEQ ID NO: 1) and one of the following doses of GSK3368715: 10 μM, 3 μM, 1 μM, 0.3 μM, 0.1 μM.
Cells treated with only one of the following doses of MS023: 10 μM, 3 μM, 1 μM, 0.3 μM, 0.1 μM.
Cells treated with only one of the following doses of GSK3368715: 10 μM, 3 μM, 1 μM, 0.3 μM, 0.1 μM.

Plates were incubated for 24h at 37° C., 5% $CO_2$. Immediately before testing, culture medium was removed and replaced with 200 μL PBS-Glucose solution (4.5 g/L, sterile) that had been warmed from 4° in a 37° C. water bath. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% $CO_2$ for 1h before one absorbance reading at 450 nm being taken on a Molecular Devices SpectraMax M3 μlate reader. Data was exported from plate reader's SoftMax Pro 7.0 software into an excel file.

As shown in FIGS. 24A-24D, GSK3368715 dose-dependently abrogated both $GR_{15}$ (SEQ ID NO: 1) and $PR_{15}$-(SEQ ID NO: 2) induced dysmetabolism in a similar pattern to MS023. Both MS023 and GSK3368715 completely abrogated $GR_{15}$ (SEQ ID NO: 1) and $PR_{15}$-(SEQ ID NO: 2) induced dysmetabolism at doses of 1 and 3 PM. The highest doses of GSK3368715 tested, 10 and 3 μM, induced dysmetabolism independently of GR15 (SEQ ID NO: 1) and PR15 (SEQ ID NO: 2) challenge. No doses of MS023 tested induced dysmetabolism independently of $GR_{15}$-(SEQ ID NO: 1) $PR_{15}$ (SEQ ID NO: 2) challenge.

Example 25: GSK3368715 (0.1-10 μM) and Abrogation of Cytotoxicity Produced by $GR_{15}$ (SEQ ID NO: 1) and $PR_{15}$ (SEQ ID NO: 2) (3 μM) Measured by LDH Assay Cells were plated in culture medium in 96-well plates at a density of $3.7 \times 10^4$ cells per well and incubated overnight at 37° C., 5% $CO_2$. The following day, immediately prior to addition of test compounds, existing culture medium was removed and replaced with staggered volumes of culture medium as in Example 1. A 10 mM stock of GSK3368715 was thawed to room temperature and diluted in warm culture medium to achieve final concentrations of 0.1, 0.3, 1, 3, and 10 μM in plate. A 10 mM stock of $GR_{15}$ (SEQ ID NO: 1) and a 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with either equivalent DMSO to GSK3368715-treated wells, equivalent DMSO to GSK3368715 and $GR_{15}$ (SEQ ID NO: 1) or $PR_{15}$-(SEQ ID NO: 2) treated wells, or equivalent DMSO to $GR_{15}$ (SEQ ID NO: 1) or $PR_{15}$-(SEQ ID NO: 2) treated wells)
GR Only (Cells treated only with 3 μM $GR_{15}$) (SEQ ID NO: 1)
Cells treated with 3 μM $GR_{15}$ (SEQ ID NO: 1) and one of the following doses of GSK3368715: 10 μM, 3 μM, 1 μM, 0.3 μM, 0.1 μM.
PR Only (Cells treated only with 3 μM $PR_{15}$) (SEQ ID NO: 2)
Cells treated with 3 μM $PR_{15}$ (SEQ ID NO: 2) and one of the following doses of GSK3368715: 10 μM, 3 μM, 1 μM, 0.3 μM, 0.1 μM.
Cells treated with only one of the following doses of GSK3368715: 10 μM, 3 μM, 1 μM, 0.3 μM, 0.1 μM.
High control/"100% toxicity" (Cells lysed with lysis buffer)
Positive control (5 μL LDH solution)

Plates were incubated for 24h at 37° C., 5% $CO_2$. Cells were tested and data were analyzed using the procedure detailed in LDH assay kit instructions.

As shown in FIGS. 25A-25D, GSK3368715 dose-dependently abrogated both $GR_{15}$ (SEQ ID NO: 1) and $PR_{15}$-(SEQ ID NO: 2) induced cytotoxicity. GSK3368715 completely abrogated $GR_{15}$ (SEQ ID NO: 1) and $PR_{15}$-(SEQ ID NO: 2) induced cytotoxicity at a dose of 1 μM. Additionally, it nearly completely abrogated $PR_{15}$-(SEQ ID NO: 2) induced cytotoxicity at a dose of 3 μM. All doses of GSK3368715 induced low levels of cytotoxicity independently of GR15 (SEQ ID NO: 1) and PR15 (SEQ ID NO: 2) challenge, however this can likely be attributed to solvent effects, as all corresponding DMSO controls displayed similar, dose-dependent levels of cytotoxicity.

Example 26: Symmetric PRMT Inhibitor GSK591 (3-200 μM) and Asymmetric PRMT Inhibitor MS023 (1-60 μM) and Abrogation of Dysmetabolism Produced by $PR_{15}$ (SEQ ID NO: 2) (3 μM) Measured by WST-1 Assay Cells were plated in culture medium in 96-well plates at a density of $3.7 \times 10^4$ cells per well, and incubated overnight at 37° C., 5% $CO_2$. The following day, immediately prior to addition of test compounds, existing culture medium was removed and replaced with staggered volumes of culture medium as in Example 1. 10 mM stocks of GSK591 and MS023 were thawed to room temperature and diluted in warm culture medium to achieve final concentrations of 3, 10, 33, 100, and 200 μM (GSK591) and 1, 3, 10, 30, and 60 μM (MS023) in plate. A 10 mM stock of $PR_{15}$ (SEQ ID NO: 2) were equilibrated to room temperature and diluted in warm culture medium to achieve a final concentration of 3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Controls (Cells treated equivalent DMSO to $GR_{15}$ (SEQ ID NO: 1) or $PR_{15}$-(SEQ ID NO: 2) treated wells)

PR Only (Cells treated only with 3 μM PR$_{15}$) (SEQ ID NO: 2)

Cells treated with 3 μM PR$_{15}$ (SEQ ID NO: 2) and one of the following doses of MS023: 60 μM, 30 μM, 10 μM, 3 μM, 1 μM.

Cells treated with 3 μM PR$_{15}$ (SEQ ID NO: 2) and one of the following doses of GSK591: 200 μM, 100 μM, 33 μM, 10 μM, 3 μM.

Cells treated with only one of the following doses of MS023: 60 μM, 30 μM, 10 μM, 3 μM, 1 μM.

Cells treated with only one of the following doses of GSK591: 200 μM, 100 μM, 33 μM, 10 μM, 3 μM.

Plates were incubated for 24h at 37° C., 5% CO$_2$. Immediately before testing, culture medium was removed and replaced with 200 μL PBS-Glucose solution (4.5 g/L, sterile) that had been warmed from 4° in a 37° C. water bath. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% CO$_2$ for 1h before one absorbance reading at 450 nm being taken on a Molecular Devices SpectraMax M3 μlate reader. Data was exported from plate reader's SoftMax Pro 7.0 software into an excel file.

As shown in FIGS. 26A-26D, MS023 dose-dependently abrogated both GR and PR-induced dysmetabolism. 3 μM and 1 μM doses of MS023 completely abrogated dysmetabolism induced by 3 μM PR$_{15}$ (SEQ ID NO: 2) challenge. No doses of GSK591 abrogated dysmetabolism induced by PR$_{15}$ (SEQ ID NO: 2) challenge. The three highest doses of GSK591 tested, 33, 100, and 200 μM, produced dysmetabolism independently of PR$_{15}$ (SEQ ID NO: 2) challenge as compared to untreated controls. No doses of MS023 tested produced dysmetabolism independently of PR$_{15}$ (SEQ ID NO: 2) challenge.

Example 27: Dose-Response Patterns of Dysmetabolism Produced by GR$_{15}$ (SEQ ID NO: 1) and Asymmetrically Dimethylated (ADMe)-GR$_{15}$ (SEQ ID NO: 1) Measured by WST-1 Assay Cells were plated in culture medium in 96-well plates at a density of 3.7×10$^4$ cells per well, and incubated overnight at 37° C., 5% CO$_2$. The following day, 10 mM stocks of GR$_{15}$ (SEQ ID NO: 1) and ADMe-GR$_{15}$ (SEQ ID NO: 1) were equilibrated to room temperature and diluted in warm culture medium to achieve a final concentration range of 10 nM-3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Controls (Cells treated equivalent DMSO to GR$_{15}$ (SEQ ID NO: 1) or ADMe-GR$_{15}$-(SEQ ID NO: 1) treated wells)
Cells treated with one of the following doses of GR$_{is}$: (SEQ ID NO: 1) 10 nM, 30 nM, 100 nM, 300 nM, 1 μM, 3 μM
Cells treated with one of the following doses of ADMe-GR$_{15}$: (SEQ ID NO: 1) 10 nM, 30 nM, 100 nM, 300 nM, 1 μM, 3 μM Plates were incubated for 24h at 37° C., 5% CO$_2$. Immediately before testing, culture medium was removed and replaced with 200 μL PBS-Glucose solution (4.5 g/L, sterile) that had been warmed from 4° in a 37° C. water bath. WST-1 reagent aliquots were thawed from −20° C. and equilibrated to room temperature before use. 20 μL WST-1 reagent was added per well containing 200 μL PBS-Glucose. Plates were incubated with WST-1 at 37° C., 5% CO$_2$ for 1h before one absorbance reading at 450 nm being taken on a Molecular Devices SpectraMax M3 μlate reader. Data was exported from plate reader's SoftMax Pro 7.0 software into an excel file.

As shown in FIGS. 27A-27E, both GR$_{15}$ (SEQ ID NO: 1) and ADMe-GR$_{15}$ (SEQ ID NO: 1) challenge induced dose-dependent dysmetabolism in NSC-34 after 24h, with ADMe-GR$_{15}$ (SEQ ID NO: 1) consistently producing more dysmetabolism than non-methylated GR$_{15}$. (SEQ ID NO: 1)

Example 28: Dose-Response Patterns of Cytotoxicity Produced by GR$_{15}$ (SEQ ID NO: 1) and Asymmetrically Dimethylated (ADMe)-GR$_{15}$ (SEQ ID NO: 1) Measured by LDH Assay Cells were plated in culture medium in 96-well plates at a density of 3.7×10$^4$ cells per well, and incubated overnight at 37° C., 5% CO$_2$. The following day, 10 mM stocks of GR$_{15}$ (SEQ ID NO: 1) and ADMe-GR$_{15}$ (SEQ ID NO: 1) were equilibrated to room temperature and diluted in warm culture medium to achieve a final concentration range of 10 nM-3 μM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Controls (Cells treated equivalent DMSO to GR$_{15}$ (SEQ ID NO: 1) or ADMe-GR$_{15}$-(SEQ ID NO: 1) treated wells)
Cells treated with one of the following doses of GR$_{15}$: (SEQ ID NO: 1) 10 nM, 30 nM, 100 nM, 300 nM, 1 μM, 3 μM
Cells treated with one of the following doses of ADMe-GR$_{15}$: (SEQ ID NO: 1) 10 nM, 30 nM, 100 nM, 300 nM, 1 μM, 3 μM
High control/"100% toxicity" (Cells lysed with lysis buffer)
Positive control (5 μL LDH solution)

Plates were incubated for 24h at 37° C., 5% CO$_2$. Cells were tested and data were analyzed using the procedure detailed in LDH assay kit instructions.

As shown in FIGS. 28A-28E, both GR$_{15}$ (SEQ ID NO: 1) and ADMe-GR$_{15}$ (SEQ ID NO: 1) challenge induced dose-dependent cytotoxicity in NSC-34 after 24h, with ADMe-GR$_{15}$ (SEQ ID NO: 1) consistently producing more cytotoxicity than non-methylated GR$_{15}$. (SEQ ID NO: 1)

Example 29: MS023 (0.1-10 μM) and Abrogation of Dysmetabolism Produced by GR$_{15}$ (SEQ ID NO: 1) and ADMe-GR$_{15}$ (SEQ ID NO: 1) (3 μM) Measured by WST-1 Assay Cells were plated in culture medium in 96-well plates at a density of 3.7×10$^4$ cells per well and incubated overnight at 37° C., 5% CO$_2$. The following day, immediately prior to addition of test compounds, existing culture medium was removed and replaced with staggered volumes of culture medium as in Example 1. A 10 mM stock of MS023 was thawed to room temperature and diluted in warm culture medium to achieve final concentrations of 0.1, 0.3, 1, 3, and 10 µM in plate. A 10 mM stock of $GR_{15}$ (SEQ ID NO: 1) and a 10 mM stock of ADMe-$GR_{15}$ (SEQ ID NO: 1) were equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with DMSO equivalent to that of $GR_{15}$ (SEQ ID NO: 1) or $PR_{15}$-(SEQ ID NO: 2) treated wells)
GR Only (Cells treated only with 3 µM $GR_{15}$) (SEQ ID NO: 1)
Cells treated with 3 µM $GR_{15}$ (SEQ ID NO: 1) and one of the following doses of MS023: 10 µM, 3 µM, 1 µM, 0.3 µM, 0.1 µM.
ADMe-GR Only (Cells treated only with 3 µM ADMe-$GR_{15}$) (SEQ ID NO: 1)
Cells treated with 3 µM ADMe-$GR_{15}$ (SEQ ID NO: 1) and one of the following doses of MS023: 10 µM, 3 µM, 1 µM, 0.3 µM, 0.1 µM.
Cells treated with only one of the following doses of MS023: 10 µM, 3 µM, 1 µM, 0.3 µM, 0.1 µM.

Plates were incubated for 24h at 37° C., 5% $CO_2$. Immediately before testing, culture medium was removed and replaced with 200 µL PBS-Glucose solution (4.5 g/L, sterile) that had been warmed from 4° in a 37° C. water bath. WST-1 reagent aliquots were thawed from −20° C. and equilibrated to room temperature before use. 20 µL WST-1 reagent was added per well containing 200 µL PBS-Glucose. Plates were incubated with WST-1 at 37° C., 5% $CO_2$ for 1h before one absorbance reading at 450 nm being taken on a Molecular Devices SpectraMax M3 plate reader. Data was exported from plate reader's SoftMax Pro 7.0 software into an excel file.

FIGS. 29A-29D, 30A-30D, and 31A-31D represent repeats of the experiment detailed above performed separately on three different dates. As shown in these figures, MS023 consistently dose-dependently abrogated dysmetabolism induced by $GR_{15}$ (SEQ ID NO: 1) challenge, but did not abrogate dysmetabolism induced by ADMe-$GR_{15}$ (SEQ ID NO: 1) challenge.

Example 30: MS023 (0.1-10 µM) and Abrogation of Cytotoxicity Produced by $GR_{15}$ (SEQ ID NO: 1) and ADMe-$GR_{15}$ (SEQ ID NO: 1) (3 µM) Measured by LDH Assay Cells were plated in culture medium in 96-well plates at a density of $3.7 \times 10^4$ cells per well and incubated overnight at 37° C., 5% $CO_2$. The following day, immediately prior to addition of test compounds, existing culture medium was removed and replaced with staggered volumes of culture medium as in Example 1. A 10 mM stock of MS023 was thawed to room temperature and diluted in warm culture medium to achieve final concentrations of 0.1, 0.3, 1, 3, and 10 µM in plate. A 10 mM stock of $GR_{15}$ (SEQ ID NO: 1) and a 10 mM stock of ADMe-$GR_{15}$ (SEQ ID NO: 1) were equilibrated to room temperature and diluted in warm culture medium to achieve a final concentration of 3 µM in wells.

The following conditions were plated in triplicate. Samples were surrounded by border wells on the outside of the plate filled with sterile Phosphate-buffered saline to prevent evaporation of volume in experimental wells during incubation:

Background (Culture medium only only)
Untreated (Cells only in culture medium)
DMSO Control (Cells treated with DMSO equivalent to that of $GR_{15}$ (SEQ ID NO: 1) or $PR_{15}$-(SEQ ID NO: 2) treated wells)
GR Only (Cells treated only with 3 µM $GR_{15}$) (SEQ ID NO: 1)
Cells treated with 3 µM $GR_{15}$ (SEQ ID NO: 1) and one of the following doses of MS023: 10 µM, 3 µM, 1 µM, 0.3 µM, 0.1 µM.
ADMe-GR Only (Cells treated only with 3 µM ADMe-$GR_{15}$) (SEQ ID NO: 1)
Cells treated with 3 µM ADMe-$GR_{15}$ (SEQ ID NO: 1) and one of the following doses of MS023: 10 µM, 3 µM, 1 µM, 0.3 µM, 0.1 µM.
Cells treated with only one of the following doses of MS023: 10 µM, 3 µM, 1 µM, 0.3 µM, 0.1 µM.
High control/"100% toxicity" (Cells lysed with lysis buffer)
Positive control (5 µL LDH solution)

Plates were incubated for 24h at 37° C., 5% $CO_2$. Cells were tested and data were analyzed using the procedure detailed in LDH assay kit instructions.

As shown in FIGS. 32A-32D, MS023 consistently dose-dependently abrogated cytotoxicity induced by $GR_{15}$ (SEQ ID NO: 1) challenge, but did not abrogate cytotoxicity induced by ADMe-$GR_{15}$ (SEQ ID NO: 1) challenge.

Figure 34:
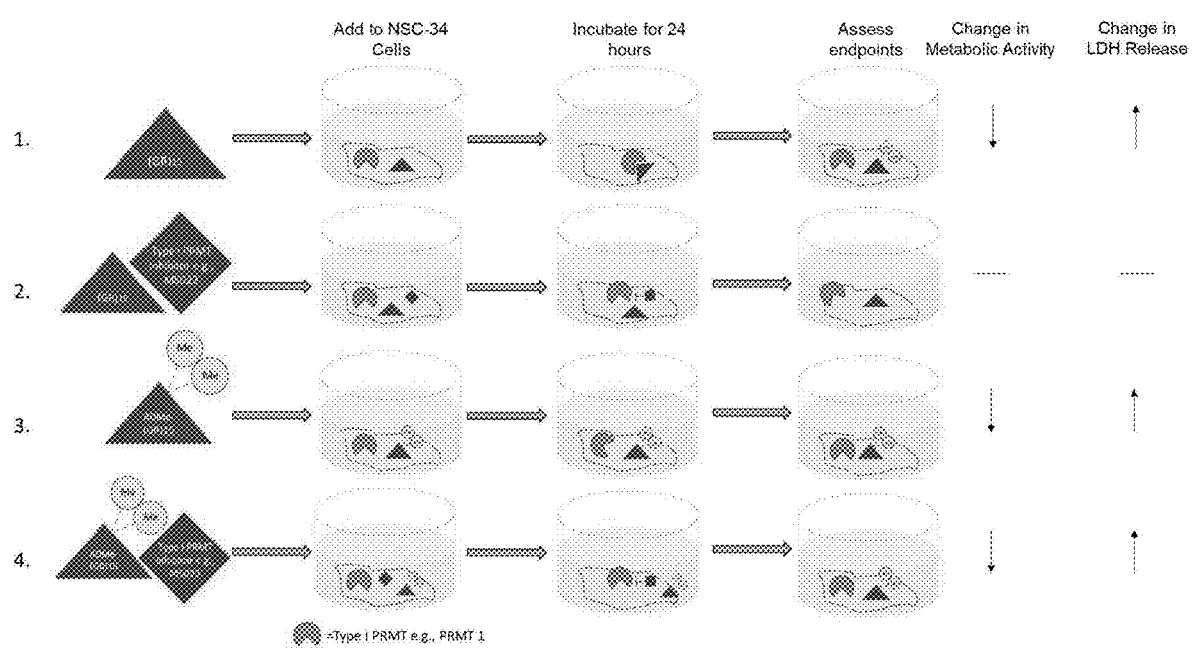
FIG. 34 is a schematic showing the outcomes of the assays described herein.

Example 31: Mechanism of toxicity As shown in the above examples, the toxicity associated with $GR_{15}$ (SEQ ID NO: 1) and $PR_{15}$ (SEQ ID NO: 2) is associated with their ability to be asymmetrically dimethylated after 24 hours of incubation (line 1 of FIG. 33). When a Type I PRMT inhibitor (such as MS023) is added, the toxicity is abrogated, though the exact mechanism by which it happens remains unclear (line 2 of FIG. 33). When challenging cells with $GR_{15}$ (SEQ ID NO: 1) that has been asymmetrically dimethylated, the toxic effects are still present (line 3 of FIG. 33). However when MS023 was added during the ADMe-$GR_{15}$ (SEQ ID NO: 1) challenge, abrogation of toxicity was not observed. Therefore, because $GR_{15}$ (SEQ ID NO: 1)was already dimethylated, the PRMT inhibition had no influence on the effects seen (line 4 of FIG. 34). Taken together, the results suggest that the asymmetric dimethylation of $GR_{15}$ (SEQ ID NO: 1) is the driving mechanism of toxicity.

The methods, compositions and embodiments of the present disclosure are not intended to be exhaustive or to limit the disclosure to the precise forms described herein. Rather, the compositions and examples are chosen so that others skilled in the art can appreciate and understand the principles and practices of the present disclosure. However, it should be understood that many variations and modifications may be made while remaining within the spirit and scope of the disclosure. Unless technically impossible, any feature or element described in connection with one embodiment can be interchangeably used with, or additively combined with, any of the other features or elements of each and every other embodiment and all such permeations are encompassed by the present disclosure.

All publications, patents, and patent applications in this specification are indicative of the level of ordinary skill in the art to which this technology pertains. All publications, patents, and patent applications are herein incorporated by reference to the same extent as if each individual publication or patent application was specifically and individually described herein.

What is claimed is:

1. A method of treating C9ORF72-linked Amyotrophic Lateral Sclerosis (ALS) or C9ORF72-linked frontotemporal dementia (FTD) in a subject, comprising administering an effective amount of a Type I PRMT inhibitor.

2. The method of claim 1, wherein the disease is associated with the expression of dipeptide repeat proteins (DRPs).

3. The method of claim 2, wherein the DRPs are generated by expansion of a hexanucleotide (GGGGCC) repeat in C9ORF72.

4. The method of claim 1, wherein the DRPs comprise arginine (R).

5. The method of claim 1, wherein the DRPs have been asymmetrically dimethylated.

6. The method of claim 1, wherein the inhibitor is selected from the group consisting of:

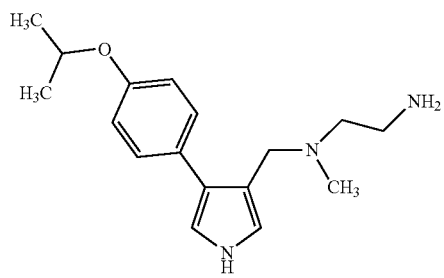 [SMILES: CC(C)Oc1ccc(-c2c[nH]cc2CN(C)CCN)cc1]

or pharmaceutically acceptable salts thereof;

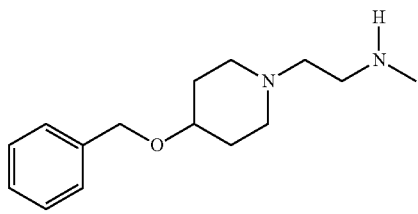 [SMILES: CNCCN1CCC(OCc2ccccc2)CC1]

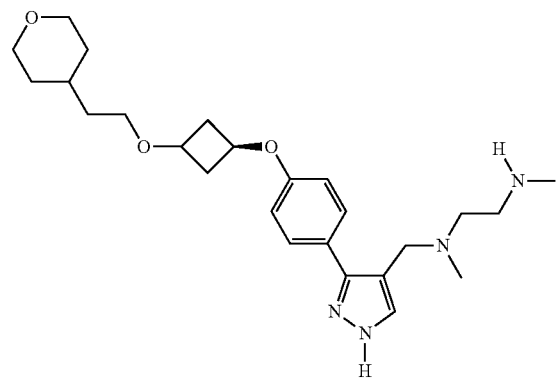

or pharmaceutically acceptable salts thereof;

or pharmaceutically acceptable salts; and

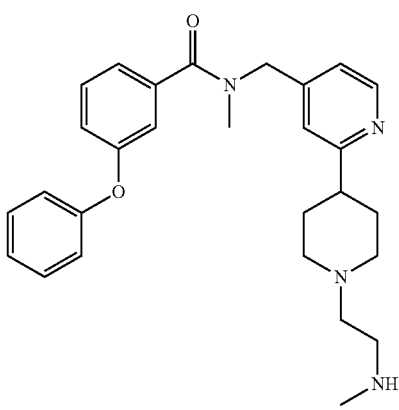 [SMILES: CNCCN1CCC(c2cc(CN(C)C(=O)c3cccc(Oc4ccccc4)c3)ccn2)CC1]

or pharmaceutically acceptable salts thereof.

* * * * *

```
                          SEQUENCE LISTING

<160> NUMBER OF SEQ ID NOS: 4

<210> SEQ ID NO 1
<211> LENGTH: 30
<212> TYPE: PRT
<213> ORGANISM: Artificial Sequence
<220> FEATURE:
<223> OTHER INFORMATION: Synthetic

<400> SEQUENCE: 1

Gly Arg Gly Arg Gly Arg Gly Arg Gly Arg Gly Arg Gly Arg Gly Arg
1               5                   10                  15

Gly Arg Gly Arg Gly Arg Gly Arg Gly Arg Gly Arg Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic

<400> SEQUENCE: 2

Pro Arg Pro Arg Pro Arg Pro Arg Pro Arg Pro Arg Pro Arg Pro Arg
1               5                   10                  15

Pro Arg Pro Arg Pro Arg Pro Arg Pro Arg Pro Arg Pro Arg
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic

<400> SEQUENCE: 3

Gly Pro Gly Pro Gly Pro Gly Pro Gly Pro Gly Pro Gly Pro Gly Pro
1               5                   10                  15

Gly Pro Gly Pro Gly Pro Gly Pro Gly Pro Gly Pro Gly Pro
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic

<400> SEQUENCE: 4

Pro Ala Pro Ala Pro Ala Pro Ala Pro Ala Pro Ala Pro Ala Pro Ala
1               5                   10                  15

Pro Ala Pro Ala Pro Ala Pro Ala Pro Ala Pro Ala
            20                  25                  30
```